US006921825B2

(12) United States Patent
Baraldi et al.

(10) Patent No.: US 6,921,825 B2
(45) Date of Patent: Jul. 26, 2005

(54) ADENOSINE $A_3$ RECEPTOR MODULATORS

(75) Inventors: Pier Giovanni Baraldi, Ferrara (IT); Pier Andrea Borea, Ferrara (IT)

(73) Assignee: King Pharmaceuticuals Research & Development, Inc., Cary, NC (US)

( * ) Notice: Subject to any disclaimer, the term of this patent is extended or adjusted under 35 U.S.C. 154(b) by 0 days.

(21) Appl. No.: 10/134,219

(22) Filed: Apr. 26, 2002

(65) Prior Publication Data

US 2003/0144266 A1 Jul. 31, 2003

Related U.S. Application Data

(63) Continuation-in-part of application No. 09/379,300, filed on Aug. 23, 1999, now Pat. No. 6,407,236, which is a continuation-in-part of application No. 09/154,435, filed on Sep. 16, 1998, now Pat. No. 6,448,253.

(51) Int. Cl.$^7$ .............................................. C07D 487/14
(52) U.S. Cl. ..................................................... 544/251
(58) Field of Search ........................... 544/251; 514/267

(56) References Cited

U.S. PATENT DOCUMENTS

| | | | | |
|---|---|---|---|---|
| 3,625,214 A | 12/1971 | Higuchi | ...................... | 128/260 |
| 4,789,734 A | 12/1988 | Pierschbacher | .............. | 530/395 |
| 4,906,474 A | 3/1990 | Langer et al. | ............... | 424/428 |
| 4,925,673 A | 5/1990 | Steiner et al. | ............... | 424/455 |
| 5,688,774 A | 11/1997 | Jacobson et al. | .............. | 514/46 |
| 5,780,481 A | 7/1998 | Jacobson et al. | ........... | 514/293 |
| 6,066,642 A | 5/2000 | Jacobson et al. | ........... | 514/267 |
| 6,117,878 A | 9/2000 | Linden | ........................ | 514/263 |
| 6,326,390 B1 * | 12/2001 | Leung et al. | ................ | 514/383 |
| 6,407,236 B1 | 6/2002 | Baraldi et al. | .............. | 544/251 |
| 6,448,253 B1 | 9/2002 | Baraldi et al. | .............. | 514/267 |

FOREIGN PATENT DOCUMENTS

| WO | WO 95/01356 | 1/1995 |
|---|---|---|
| WO | WO 96/38728 | 12/1996 |
| WO | WO 97/05138 | 2/1997 |
| WO | WO 00/15231 | 3/2000 |

OTHER PUBLICATIONS

Fishman, P. et al, Anticancer Drugs, 2002, 13(5), 437–43, Medline abstract PMID 12045454.*
Muller, C.E. and Stein, B., Current Pharmaceutical Design, 1996, 2, 501–530.*
Muller, C.E., Curr. Top. Med. Chem., 2003, 3(4), 445–462, Medline abstract PMID.*
Fishman, P. et al, Curr. Top. Med. Chem., 2003, 3(4), 463–9, Medline abstract PMID 12570762.*
B. Adcock, et al., "2–Amino–2–Imidazolines and 2–Amino–2–Oxalines," J. Chem. Soc. 1961 pp. 5120–5127.
M. Abbracchio, et al., "G–Protein–Dependent Activation of Phospholipase C by Adenosine A3 Receptors in Rat Brain," Mol. Pharmacol,. Dec., 1995; vol. 48, No. 6, pp. 1038–1045.

H. Ali, et al., "Sustained Activation of Phospholipase D via Adenosine A3 Receptors is Associated with Enhancement of Antigen–and Ca2+–Ionophore–Induced Secretion in a Rat Mast Cell Line," J. Pharmacol. Exp. Ther., Feb., 1996, vol. 276, No. 2, pp. 837–845.
P. Baraldi, et al., "Synthesis of the Tritium Labeled SCH 58261, A New Non–Xanthine A2A Adenosine Receptor Antagonist," J. of Labeled Com. & Radiopharm. 1996, vol. 37, No. 8, pp. 725–732.
P. Baraldi, et al., "Synthesis of 1H–Pyrazolo[4,3–D] Pyrimidine–7(6H)–Ones and Pyrazolo–5–Carboxamides and Interaction with Benzodiazepine and Adenosine A1 Receptors in Rat Cerebral Cortex," Arzneim. Forsch. Drug Res., 1988, vol. 38, No. 11, pp. 1262–1265.
P. Baraldi, et al., "Synthesis and Biological Activity of a New Series of N6–Arylcarbamoyl, 2–(AR)Alkynyl–N6–Arylcarbamoyl, and N6–Carboxamido Derivatives of Adenosine–5'–N–Ethyluronamide as A1 and A3 Adenosine Receptor Agonists," J. Med. Chem. Aug. 13, 1998, vol. 41, No. 17, pp. 3174–3185.
P. Baraldi, et al., "Synthesis of New Pyrazolo[4,3–e] 1,2, 4–Triazolo [1,5–c] Pyrimidine Displaying Potent and Selective Activity as A2A Adenosine Receptor Antagonists," Bioorg. Med. Chem. Lett. 1994, vol. 4, No. 21, pp. 2539–2544.
P. Baraldi, et al., "Novel N6–(Substituted–Phenylcarbamoyl) Adenosine–5'–Uronamides as Potent Agonists for A3 Adenosine Receptors," J. Med. Chem., Feb. 2, 1996, vol. 39, No. 3, pp. 802–806.
P. Baraldi, et al., "Pyrazolo[4,3–e]–1,2,4–Triazolo[1,5–c] Pyrimidine Derivatives: Potent and Selective A2A Adenosine Antagonists," J. Med. Chem., Mar. 1, 1996 vol. 39, No. 5, pp. 1164–1171.

(Continued)

Primary Examiner—Thomas C. McKenzie
(74) Attorney, Agent, or Firm—Edwards & Angell, LLP; David G. Conlin, Esq.; Gregory B. Butler, Esq.

(57) ABSTRACT

The compounds of the following formula:

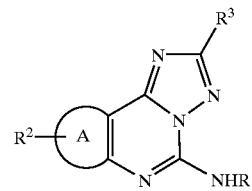

wherein R, $R^2$, $R^3$ and A have the meanings given in the specification, are endowed with selective $A_3$ adenosine receptor antagonist activity. These compounds can be used in a pharmaceutical composition to treat disorders caused by excessive activation of the $A_3$ receptor, or can be used in a diagnostic application to determine the relative binding of other compounds to the $A_3$ receptor. The compounds can be labeled, for example with fluorescent or radiolabels, and the labels used in vivo or in vitro to determine the presence of tumor cells which possess a high concentration of adenosine $A_3$ receptors.

8 Claims, 5 Drawing Sheets

OTHER PUBLICATIONS

P. Baraldi, et al., "Design Synthesis, and Biological Evaluation of a Second Generation of Pyrazolo[4,3–e]–1,2,4–Triazolo[1,5–c] Pyrimidines as Potent and Selective A2A Adenosine Receptor Antagonists," J. Med. Chem., Jun. 4, 1998, vol. 41, NO 12, pp. 2126–2133.

P. Baraldi, et al., "Current Developments of A2A Adenosine Receptor Antagonists," Curr. Med. Chem., 1995, vol. 2, pp. 707–722.

P. Barladi, et al., "1,2,3–Triazolo[5,4–e]1,2,4–Triazolo[1,5–c] Pyrimidine Deritivies: A New Class of A2A Adenosine Receptor Antagonists," IL Farmaco, 1996, vol. 51, No. 4, pp. 297–300.

P. Baraldi, et al., "1H–Pyrazolo[4,3–d] Pyrimidine–7(6H)–One and 5H–Pyrazolo[4,3–d] 1,2,3–Triazin–4(3H)–One Derivatives and Synthesis and In Vitro Biological Activity at Adenosine A1 and A2A Receptors," Arzneimittelforschung. Apr. 1996, vol. 46, No. 4, pp. 365–368.

P. Baraldi, et al., "Synthesis of 3–Substituted–7–Alkoxy–5H–Pyrazolo[4,3–d]–1,2,3–Triazin–4–(3H)–Ones," Dec. 1994, vol. 12, pp. 1437–1440.

P. Baraldi, et al., "Synthesis and Preliminary Biological Evaluation of [3H]–MRE 3008–F20: The First High Affinity Radioligand Antagonist for the Human A3 Adenosine Receptors," Bioorg. & Med. Chem. Letters, 2000, vol. 10, pp. 209–211.

M. Bradford, "A Rapid and Sensitive Method for the Quantitation of Microgram Quantities of Protein Utilizing the Principle of Protein–Dye Binding," Anal. Biochem., May 7, 1976, vol. 72, pp. 248–254.

R. Bruns, et al., "Adenosine Receptors in Brain Membranes: Binding of N6–Cyclohexyl [3H] Adenosine and 1,3–Diethyl–8–[3H] Phenylxanthine," Proc., Natl. Acad. Sci. USA, Sep. 1980, vol. 77, No. 9, pp. 5547–5551.

Y. Cheng, et al., "Relationship Between the Inhibition Constant (KI) and the Concentration of Inhibitor Which Causes 50 Per Cent Inhibition (I50) of an Enzymatic Reaction," Biochem. Pharm., Dec. 1, 1973, vol. 22, No. 23, pp. 3099–3108.

C. Cheng, et al., Potential Purine Antagonists. VI. Synthesis of 1–Alkyl–and 1–Aryl–4–Substituted Pyrazolo[3,4–d] Pyrimidines, J. Org. Chem., 1956, vol. 21, pp. 1240–1258.

L. Colombetti, "Principles of Radiopharmacology," CRC Press, 1979, pp. 11–13, and 24.

P. Crooks, et al., "Synthesis of 5–Benzoyl–5–Phenyl–and 5–Phenylhydroxymethyl–5–Phenylhydantoins as Potential Anticonvulsants," J. Heter. Chem., Jul.–Aug. 1989, vol. 26, No. 4, pp. 1113–1117.

M. DeNinno, et al., Annual Reports in Medicinal Chemistry, 33, 1998, pp. 111–120.

B. Fredholm, et al., "Nomenclature and Classification of Purinoceptors," Pharm. Rev., Jun. 1994, vol. 46, No. 2, pp. 143–156.

G. Gregoriades, "Liposomes," Drug Carriers in Biology and Med., 1979, pp. 287–341.

J. Hannon, et al., "A Role for Mast Cells in Adenosine A3 Receptor–Mediated Hypotension in the Rat," British Journal of Pharm., Jul. 1995, vol. 115, No. 6, pp. 945–952.

R. Hill, et al., "Cloning, Expression and Pharmacological Characterization of Rabbit Adenosine A1 and A3 Receptors," J. Pharmacol. Exp. Ther., Jan. 1997, vol. 280, No. 1, pp. 122–128.

A. Howlett, "Pharmacology of Cannabinoid Receptors," Ann. Rev. Pharmacol. Toxicol. 1995, vol. 35, pp. 607.

K. Jacobson, "Adenosine A3 Receptors: Novel Ligands and Paradoxical Effects," Trends Pharmacol. Sci., May 1998, vol. 19, No. 5, pp. 184–191.

K. Jacobson, et al., "Recent Developments in Selective Agonists and Antagonists Acting at Purine and Pyrimidine Receptors," Drug Dev. Res. 1996, vol. 39, pp. 4667–4675.

K. Jacobson, et al., "Development of Selective Purinoceptor Agonists and Antagonists" Purinergic Approaches in Experimental Therapeutics, 1997, vol. 6, pp. 101–128.

J. Jiang, et al., "6–Phenyl–1,4–Dihydropyridine Derivatives as Potent and Selective A3 Adenosine Receptor Antagonists," J. Med. Chem. Nov. 8, 1996, vol. 39, No. 23, pp. 4667–4675.

J. Jiang, et al., "Structure–Activity Relationships of 4–(Phenylethynyl)–6–Phenyl–1,4–dihydropyridines as Highly Selective A3 Adenosine Receptor Antagonists," J. Med. Chem., Aug. 1, 1997, vol. 40, No. 16, pp. 2596–2608.

J. Kagan, et al., "The Synthesis and Photochemistry of 4–Amino–3–Cyanopyrazole," J. Heter. Chem., Sep. 1979, vol. 16, No. 6, pp. 1113–1115.

Y. Karton, et al., "Synthesis and Biological Activities of Flavornoid Derivatives as A3 Adenosine Receptor Antagonists," J. Med. Chem., Jun. 7, 1996, vol. 39, No. 12, pp. 2293–2301.

Y. Kim, et al., "Derivatives of the Triazoloquinazoline Adenosine Antagonist (CGS15943) are Selective for the Human A3 Receptor Subtype," J. Med. Chem., Oct. 11, 1996, vol. 39, No. 21, pp. 4142–4148.

Y. Kim, et al., Derivatives of the Triazoloquinazoline Adenosine Antagonist (CGS15943) Having High Potency at the Human A2B and A3 Receptor Subtypes, J. Med. Chem., 1998, vol. 41, pp. 2835–2845.

A. Li, et al., Structure–Activity Relationships and Molecular Modeling of 3,5–Diacyl–2,4–Dialkylpyridine Derivatives as Selective A3 Adenosine Receptor Antagonists, J. Med. Chem., Aug. 13, 1998, vol. 41, No. 17, pp. 3186–3201.

J. Linden, "Cloned Adenosine A3 Receptors: Pharmacological Properties, Species Differences and Receptor Functions," Trends Pharmacol. Sci., Aug. 1994, vol. 15, No. 8, pp. 298–306.

J. Linden, et al., "Molecular Cloning and Functional Expression of a Sheep A3 Adenosine Receptor with Widespread Tissue Distribution," Molecular Pharm., Sep. 1993, vol. 44, No. 3, pp. 524–532.

M. Lohse, et al., "8–Cyclopentyl–1,3–Dipropylxanthine (DPCPX)—A Selective High Affinity Antagonist Radioligand for A1 Adenosine Receptors," Naunyn Schmiedebergs Arch. Pharmacol. Aug. 1987, vol. 336, No. 2, pp. 204–210.

W. MacKenzie, et al., "Adenosine Inhibits the Adhesion of Anti–CD3–Activated Killer Lymphocytes to Adenocarcinoma Cells through an A3 Receptor," Cancer Research, Jul. 1994, vol. 54, No. 13, pp. 3521–3526.

R.A.A. Mathot, et al., "Deoxyribose Analogues of N6–Cyclopentyladenosine (CPA): Partial Agonists at the Adenosine A1 Receptor In Vivo," British Journal of Pharm., Oct. 1995, vol. 116, No. 3, pp. 1957–1964.

C. Meade, et al., "In Vivo Role of the Adenosine A3 Receptor: N6–2–(4–Aminophenyl) Ethyladenosine Induces Bronchospasm in BDE Rats by a Neurally Mediated Mechanism Involving Cells Resembling Mast Cells," J. Pharmacol. Exp. Ther., Dec. 1996, vol. 279, No. 3, pp. 1148–1156.

W. Meyerhof, et al., "Molecular Cloning of a Novel Putative G-Protein Coupled Receptor Expressed During Rat Spermiogenesis," FEBS Letter, Jun. 1991, vol. 284, No. 2, pp. 155–160.

S. Moro, et al., "Flavonoid Derivatives as Adenosine Receptor Antagonists: A Comparison of the Hypothetical Receptor Binding Site Based on a Comparative Molecular Field Analysis Model," J. Med. Chem., Jan. 1, 1998, vol. 41, No. 1, pp. 46–52.

P. Munson, et al., "Ligand: A Versatile Computerized Approach for Characterization of Ligand–Binding Systems," Analytical Biochemistry, 1990, vol. 107, pp. 220–239.

M. Olah, et al., "Adenosine Receptor Subtypes: Characterization and Therapeutic Regulation," Annual Rev. Pharmacol. Toxicol., 1995, vol. 35, pp. 581–606.

V. Ramkumar, et al., "The A3 Adenosine Receptor is the Unique Adenosine Receptor Which Facilitates Release of Allergic Mediators in Mast Cells," J. of Biological Chem., Aug. 15, 1993, vol. 268, No. 23, pp. 16887–16890.

F. Sajjadi, et al., "cDNA Cloning and Sequence Analysis of the Human A3 Adenosine Receptor," Biochimica et Biophysica ACTA, Oct. 7, 1993, vol. 1179, No. 1, pp. 105–107.

C. Salvatore, et al., "Molecular Cloning and Characterization of the Human A3 Adenosine Receptor," Proc. Natl., Acad. Sci., Nov. 1, 1993, vol. 90, No. 21, pp. 10365–10369.

J. Shultz, et al., "Studies of the Fischer–Tropsch Synthesis. XV. Cementite as Catalysts," Amer. Chem. Soc. vol. 78, 1956, pp. 282–285.

K. Takagi, et al., "Sur la Formation d'un Derive Pyrazolique Original a Partir d'Hydrazine et d'Ethoxymethylene Malononitrile," Chem. Pharm. Bull., 1970, vol. 18, pp. 2353–2356.

S. Van Calenbergh, et al., N6–Cyclopentyl-3'-Substituted–Xylofuranosyladenosines: A New Class of Non–Xanthine Adenosine A1 Receptor Antagonists, J. Med. Chem., Nov. 7, 1997, vol. 40, No. 23, pp. 3765–3772.

E. van der Wenden, et al., "Ribose–Modified Adenosine Analogues as Potential Partial Agonists for the Adenosine Receptor," J. Med. Chem., Sep. 29, 1995, vol. 38, No. 20, pp. 4000–4006.

J. van Muijlwijk–Koezen, et al., "A Novel Class of Adenosine A3 Receptor Ligands. 2. Structure Affinity Profile of a Series of Isoquinoline and Quinazoline Compounds," J. Med. Chem., Oct. 8, 1998, vol. 41, No. 21, pp. 3994–4000.

J. van Muijlwijk–Koezen, et al., "A Novel Class of Adenosine A3 Receptor Ligands. 1. 3–(2–Pyridinyl) Isoquinoline Derivatives," J. Med. Chem., Oct. 8, 1998, vol. 41, No. 21, pp. 3987–3993.

A. van Rhee, et al., "Interaction of 1,4–Dihydropyridine and Pyridine Derivatives with Adenosine Receptors: Selectively for A3 Receptors," J. Med. Chem., 1996, vol. 39, No. 15, pp. 2980–2989.

E. Van Schiack, et al., "Hemodynamic Effects and Histamine Release Elicited by the Selective Adenosine A3 Receptor Agonist 2–Cl–IB–MECA in Conscious Rats," European Journal of Pharmacol., Jul. 25, 1996, vol. 308, No. 3, pp. 311–314.

D. Von Lubitz, et al., "Adenosine A3 Receptor Stimulation and Cerebral Ischemia," European Journal of Pharmacol., Sep. 22, 1994, vol. 263, Nos. 1–2, pp. 59–67.

D. Von Lubitz, et al., "The Effects of Adenosine A3 Receptor Stimulation on Seizures in Mice," European Journal of Pharmacol., Feb. 24, 1995, vol. 275, No. 1, pp. 23–29.

Y. Yao, et al., Adenosine A3 Receptor Agonists Protect HL–60 and U–937 Cells from Apoptosis Induced by A3 Antagonists, Biochemical and Biophysical Research Communications, Mar. 17, 1997, vol. 232, No. 2, pp. 317–322.

Z. Zhao, et al., "Chromosonal Mapping of the Mouse A3 Adenosine Receptor Gene, Adora 3," Genomics, Nov. 1, 1995, vol. 30, No. 1, pp. 118–119.

C. Zocchi, et al., "Binding of the Radioligand [3H]–SCH 58261, A New Non–Xanthine A2A Receptor Antagonist, to Rat Striatal Membranes," British Journal of Pharmacol., Apr. 1996, vol. 117, No. 7, pp. 1381–1386.

C. Zocchi, et al., "The Non–Xanthine Heterocyclic Compound SCH 58261 is a New Potent and Selective A2A Adenosine Receptor Antagonist," J. of Pharmacol. Exp. Ther., Feb. 1996, vol. 276, No. 2, pp. 398–404.

C. Zocchi, et al., "SCH 58261, A New Potent and Selective Adenosine A2A Receptor Antagonist," British Journal of Pharmacology,1995, vol. 114, pp. 229–300.

American Radiolabeled Chemicals, Inc. St. Louis, Date Unknown, pp. 3–5, and 183–208.

International Search Report Dated Jul. 9, 2002, Issued in Corresponding PCT Patent Application No. PCT/US02/14191, filed May 6, 2002.

Internation Search Report Dated Jan. 18, 2000, Issued in Corresponding PCT Patent Application No. PCT/US99/21103, Filed Sep. 15, 1999.

* cited by examiner

ADENOSINE A₃ RECEPTOR MODULATORS

CROSS REFERENCE TO OTHER PATENT APPLICATIONS

This application is a continuation-in-part of U.S. patent application Ser. No. 09/379,300 filed Aug. 23, 1999 now U.S. Pat. No. 6,407,236 which is a continuation-in-part of U.S. patent application Ser. No. 09/154,435 filed Sep. 16, 1998 now U.S. Pat. No. 6,448,253.

BACKGROUND OF THE INVENTION

The present invention relates to certain pyrazolo-triazolo-pyrimidine, triazolo-triazolo-pyrimidine and imidazolo-triazolo-pyrimidine derivatives and their use in the practice of medicine as modulators of adenosine $A_3$ receptors.

Three major classes of adenosine receptors, classified as $A_1$, $A_2$, and $A_3$, have been characterized pharmacologically. $A_1$ receptors are coupled to the inhibition of adenylate cyclase through $G_i$ proteins and have also been shown to couple to other second messenger systems, including inhibition or stimulation of phosphoinositol turnover and activation of ion channels. $A_2$ receptors are further divided into two subtypes, $A_{2A}$ and $A_{2B}$, at which adenosine agonists activate adenylate cyclase with high and low affinity, respectively. The $A_3$ receptor sequence was first identified in a rat testes cDNA library, and this sequence, later cloned by homology to other G-protein coupled receptors from a rat brain cDNA library, was shown to correspond to a novel, functional adenosine receptor.

The discovery of the $A_3$ receptor has opened new therapeutic vistas in the purine field. In particular, the $A_3$ receptor mediates processes of inflammation, hypotension, and mast cell degranulation. This receptor apparently also has a role in the central nervous system. The $A_3$ selective agonist IB-MECA induces behavioral depression and upon chronic administration protects against cerebral ischemia. $A_3$ selective agonists at high concentrations were also found to induce apoptosis in HL-60 human leukemia cells. These and other findings have made the $A_3$ receptor a promising therapeutic target. Selective antagonists for the $A_3$ receptor are sought as potential antiinflammatory or possibly antiischemic agents in the brain.

Mast cell degranulation is a component of myocardial reperfusion injury, hypersensitivity reactions (asthma, allergic rhinitis, and urticaria), ischemic bowel disease, autoimmune inflammation, and atopic dermatitis. Selective $A_3$ adenosine receptor antagonists can be used to treat or prevent these diseases and pathologic effects that result from mast cell degranulation.

For example, $A_3$ antagonists have been under development as antiasthmatic, antidepressant, antiarrhythmic, renal protective, antiparkinson and cognitive enhancing drugs.

Further investigation has identified $A_3$ receptors in a number of human cancers, including pancreatic cancer, colon cancer, breast cancer, lung cancer and human malignant melanoma. Surprisingly, $A_3$ receptors are found at higher concentrations in the cancerous cells as compared to normal healthy tissue.

Although others have studied the apoptosis induced effect of $A_3$ agonists, inventors have also demonstrated success in using $A_3$ antagonists to induce apoptosis in human cancers. The use of $A_3$ antagonists with selectivity allows targeting of the cancer cells for apoptosis thereby reducing anticipated side effects in treatment of patients.

It is therefore an object of the present invention to provide compounds and methods of preparation and use thereof, which are antagonists or partial antagonists of the adenosine $A_3$ receptor.

BRIEF SUMMARY OF THE INVENTION

Compounds and pharmaceutical salts thereof useful as potent, yet selective modulators of the adenosine $A_3$ receptor, with activity as antagonists of this receptor, and methods of preparation and use thereof, are disclosed. The compounds have the following general formula:

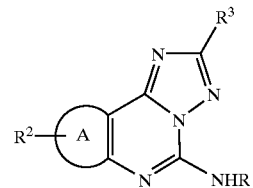

wherein:

A is imidazole, pyrazole, or triazole;

R is —C(X)R¹, —C(X)—N(R¹)₂, —C(X)OR¹, —C(X)SR¹, —SO_n—R¹, —SO_nOR¹, —SO_n—SR¹, or SO_n—N(R¹)₂;

R¹ is hydrogen, alkyl, substituted alkyl, alkenyl, substituted alkenyl, alkynyl, substituted alkynyl, aryl, substituted aryl, heteroaryl, heterocyclic, lower alkenyl, lower alkanoyl, or, if linked to a nitrogen atom, then taken together with the nitrogen atom, forms an azetidine ring or a 5–6 membered heterocyclic ring containing one or more heteroatoms;

R² is hydrogen, alkyl, substituted alkyl, aralkyl, substituted aralkyl, heteroaryl, substituted heteroaryl or aryl;

R³ is furan, pyrrole, thiophene, benzofuran, benzypyrrole, benzothiophene, optionally substituted with one or more substituents selected from the group consisting of hydroxy, acyl, alkyl, alkoxy, alkenyl, alkynyl, substituted alkyl, substituted alkoxy, substituted alkenyl, substituted alkynyl, amino, substituted amino, aminoacyl, acyloxy, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, thioalkoxy, substituted thioalkoxy, thioaryloxy, thioheteroaryloxy, —SO-alkyl, —SO-substituted alkyl, —SO-aryl, —SO-heteroaryl, —SO₂-alkyl, —SO₂-substituted alkyl, —SO₂-aryl, —SO₂-heteroaryl, and trihalomethyl;

X is O, S, or NR¹; and n is 1 or 2.

Preferably, R¹ is hydrogen; C1 to C8 alkyl; C2 to C7 alkenyl, C2 to C7 alkynyl; C3 to C7 cycloalkyl; C1 to C5 alkyl substituted with one or more halogen atoms, hydroxy groups, C1 to C4 alkoxy, C3 to C7 cycloalkyl or groups of formula —N(R¹)₂, —C(O)N(R¹)₂; aryl, substituted aryl wherein the substitution is selected from the group consisting of C1 to C4 alkoxy, C1 to C4 alkyl, nitro, amino, cyano, C1 to C4 haloalkyl, C1 to C4 haloalkoxy, carboxy, carboxyamido; C7 to C10 aralkyl in which the aryl moiety can be substituted with one or more of the substituents indicated above for the aryl group; a group of formula —(CH₂)m-Het, wherein Het is a 5–6 membered aromatic or non aromatic heterocyclic ring containing one or more heteroatoms selected from the group consisting of N, O, and S and m is an integer from 0 to 5.

Preferred C1 to C8 alkyl groups are methyl, ethyl, propyl, butyl and isopentyl. Examples of C3 to C7 cycloalkyl groups include cyclopropyl, cyclopentyl, and cyclohexyl. Examples of C1 to C5 alkyl groups substituted with C3 to C7 cycloalkyl groups include cyclohexylmethyl, cyclopentylmethyl, and 2-cyclopentylethyl. Examples of substituted C1 to C5 alkyl groups include 2-hydroxyethyl, 2-methoxyethyl, trifluoromethyl, 2-fluoroethyl, 2-chloroethyl, 3-aminopropyl, 2-(4methyl-1-piperazine) ethyl, 2-(4-morpholinyl)ethyl, 2-aminocarbonylethyl, 2-dimethylaminoethyl, 3-dimethylaminopropyl. Aryl is preferably phenyl, optionally substituted. Examples of 5 to 6 membered ring heterocyclic groups containing N, O and/or S include piperazinyl, morpholinyl, thiazolyl, pyrazolyl, pyridyl, furyl, thienyl, pyrrolyl, triazolyl, tetrazolyl. Examples of C7 to C10 aralkyl groups comprise benzyl or phenethyl optionally substituted by one or more substituents. Preferably, $R^1$ is hydrogen, C1 to C8 alkyl, aryl or C7 to C10 aralkyl, optionally substituted, preferably with halogen atoms. Preferably, X is O, $R^2$ is C2–3 alkyl or substituted alkyl and $R^3$ is furan.

Particularly preferred compounds are those in which $R^2$ is an alkyl.

The possible meanings of A can be represented by the following structural formulae:

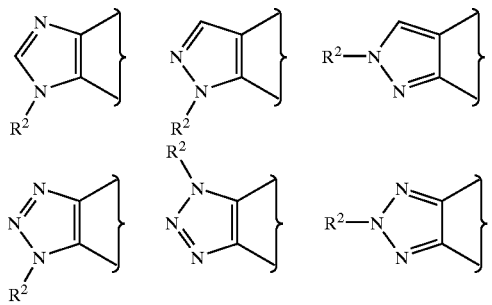

The compounds can be used in a method for modulating adenosine $A_3$ receptors in a mammal, including a human. The methods involve administering an effective amount of a compound of formula I sufficient to moderate adenosine $A_3$ receptors in the mammal. Uses for the compounds include:

treating hypertension;

treating inflammatory disorders such as rheumatoid arthritis and psoriasis;

treating allergic disorders such as hay fever and allergic rhinitis;

mast cell degranulation;

antitumor agents;

treating cardiac hypoxia; and protection against cerebral ischemia;

diagnostic uses, for example, to determine the presence of one or more of the above described medical conditions, or in a screening assay to determine the effectiveness of other compounds for binding to the $A_3$ adenosine receptor (i.e., through competitive inhibition as determined by various binding assays), as described in Jacobson and Van Rhee, Purinergic approaches to experimental therapy, Jacobson and Jarvis, ed., Wiley, New York, 1997, pp. 101–128; Mathot et al., *Brit. J. Pharmacol*,. 116:1957–1964 (1995); van der Wenden et al., *J. Med. Chem*,. 38:4000–4006 (1995); and van Calenbergh, *J. Med. Chem*,. 40:3765–3772 (1997), the contents of which are hereby incorporated by reference.

The compounds can also be used in a method for fully or partially inhibiting adenylate cyclase ($A_3$) in a mammal, including a human. The methods involve administering an effective amount of a compound of formula I sufficient to fully or partially inhibit adenylate cyclase in the mammal.

The compounds can also be labeled and used to detect the presence of tumor cells containing adenosine $A_3$ ligands in a patient or in a cell sample, by contacting the cells with the labeled compound, allowing the compound to bind to the $A_3$ receptors, and detecting the presence of the label.

The compounds can be used in a pharmaceutical formulation that includes a compound of formula I and one or more excipients. Various chemical intermediates can be used to prepare the compounds.

DETAILED DESCRIPTION OF THE INVENTION

Figure 1:
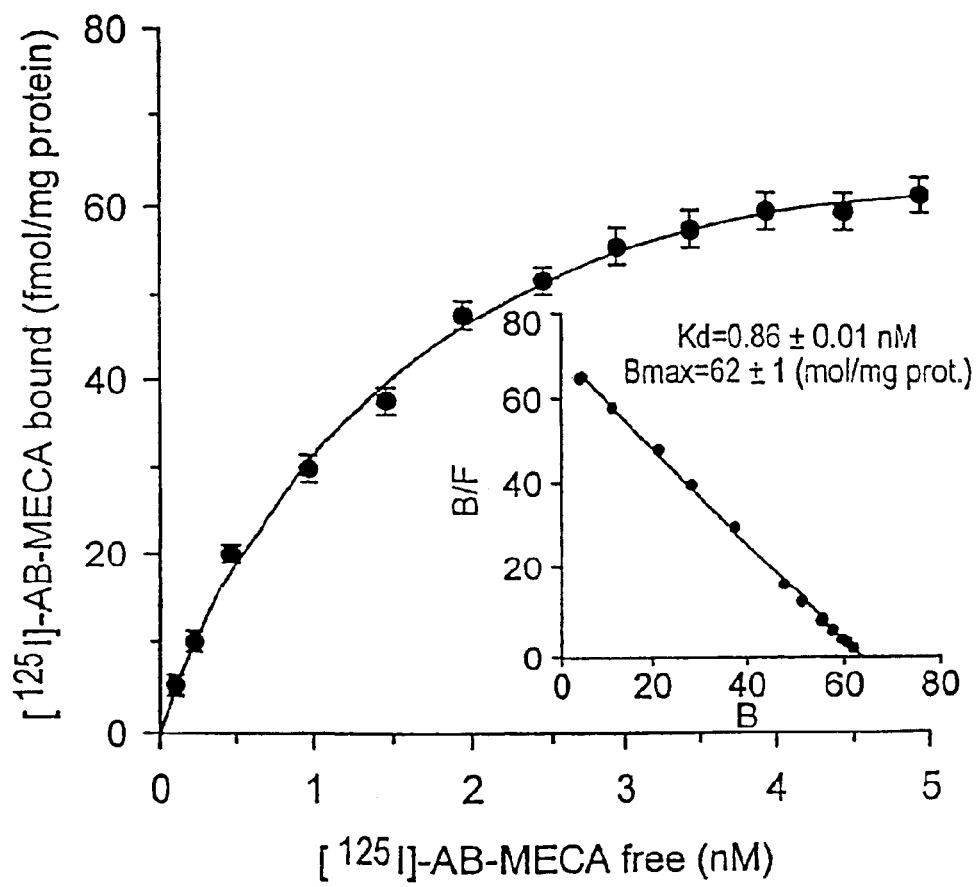
FIG. 1 is a graph showing the saturation of $[^{125}I]$AB-MECA binding (fmol/mg protein) to human $A_3$ receptors expressed in HEK 293 cells versus the molar concentration of $[^{125}I]$AB-MECA.

The present application discloses compounds useful as potent, yet selective modulators of adenosine receptors, with activity as $A_3$ antagonists, and in some cases, $A_3$ agonists, and methods of preparation and use thereof.

The compounds can be used in a method for modulating adenosine $A_3$ receptors in a mammal, including a human. The methods involve administering an effective amount of a compound of formula I sufficient to moderate adenosine $A_3$ receptors to the mammal.

The compounds can be used in a pharmaceutical formulation that includes a compound of formula I and one or more excipients. Various chemical intermediates can be used to prepare the compounds.

DEFINITIONS

As used herein, a compound is an agonist of an adenosine $A_3$ receptor if it is able to fully inhibit adenylate cyclase ($A_3$) and is able to displace $[^{125}I]$-AB-MECA in a competitive binding assay.

As used herein, a compound is a partial agonist of an adenosine $A_3$ receptor if it is able to partially inhibit adenylate cyclase ($A_3$) and is able to displace $[^{125}I]$-AB-MECA in a competitive binding assay.

As used herein, a compound is an antagonist of an adenosine $A_3$ receptor if it is able to prevent the inhibition due to an agonist and is able to displace $[^{125}I]$-AB-MECA in a competitive binding assay.

As used herein, a compound is selective for the $A_3$ receptor if the ratio of $A_1/A_3$, $A_{2A}/A_3$ and $A_{2B}/A_3$ activity is greater than about 50, preferably between 50 and 100, and more preferably, greater than about 100.

As used herein, the term "alkyl" refers to monovalent straight, branched or cyclic alkyl groups preferably having from 1 to 20 carbon atoms, more preferably 1 to 10 carbon atoms ("lower alkyl") and most preferably 1 to 6 carbon atoms. This term is exemplified by groups such as methyl, ethyl, n-propyl, isopropyl, -butyl, isobutyl, n-hexyl, and the like. The terms "alkylene" and "lower alkylene" refer to divalent radicals of the corresponding alkane. Further, as used herein, other moieties having names derived from alkanes, such as alkoxyl, alkanoyl, alkenyl, cycloalkenyl, etc when modified by "lower," have carbon chains of ten or less carbon atoms. In those cases where the minimum number of carbons are greater than one, e.g., alkenyl (minimum of two carbons) and cycloalkyl, (minimum of three carbons), it is to be understood that "lower" means at least the minimum number of carbons.

As used herein, the term "substituted alkyl" refers to an alkyl group, preferably of from 1 to 10 carbon atoms ("substituted lower alkyl"), having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino aminoacyl, aminoacyloxy, oxyacylamino, cyano, halogen, hydroxyl, keto, thioketo, carboxyl, carboxylalkyl, thiol, thioalkoxy, substituted thioalkoxy, aryl, substituted aryl, aryloxy, heteroaryl, heteroaryloxy, heterocyclic, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and mono- and di-alkylamino, mono- and di-(substituted alkyl) amino, mono- and di-arylamino, mono- and di-heteroarylamino, mono- and di-heterocyclic amino, and unsymmetric di-substituted amines having different substituents selected from alkyl, aryl, heteroaryl and heterocyclic. As used herein, other moieties having the prefix "substituted" are intended to include one or more of the substituents listed above.

As used herein, "alkaryl" refers to an alkyl group with an aryl substituent. Attachment to the core molecule is through the alkyl group. "Aralkyl" refers to an aryl group with an alkyl substituent, where attachment is through the aryl group.

As used herein, the term "alkoxy" refers to the group "alkyl-O—", where alkyl is as defined above. Preferred alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

As used herein, the term "alkenyl" refers to alkenyl groups preferably having from 2 to 10 carbon atoms and more preferably 2 to 6 carbon atoms and having at least 1 and preferably from 1–2 sites of alkenyl unsaturation. Preferred alkenyl groups include ethenyl (—CH=CH2), n-propenyl (—CH2CH=CH2), iso-propenyl (—C(CH3)=CH2), and the like.

As used herein, the term "alkynyl" refers to alkynyl groups preferably having from 2 to 10 carbon atoms and more preferably 2 to 6 carbon atoms and having at least 1 and preferably from 1–2 sites of alkynyl unsaturation.

As used herein, the term "acyl" refers to the groups alkyl-C(O)—, substituted alkyl-C(O)—, cycloalkyl-C(O)—, substituted cycloalkyl-C(O)—, aryl-C(O)—, heteroaryl-C(O)— and heterocyclic-C(O)— where alkyl, substituted alkyl, cycloalkyl, substituted cycloalkyl, aryl, substituted aryl, heteroaryl and heterocyclic are as defined herein.

As used herein, the term "acylamino" refers to the group —C(O)NRR where each R is independently hydrogen, alkyl, substituted alkyl, aryl, substituted aryl, heteroaryl, or heterocyclic wherein alkyl, substituted alkyl, aryl, substituted aryl, heteroaryl and heterocyclic are as defined herein.

As used herein, the term "aryl" refers to an unsaturated aromatic carbocyclic group of from 6 to 14 carbon atoms having a single ring (e.g., phenyl) or multiple condensed (fused) rings (e.g., naphthyl or anthryl). Preferred aryls include phenyl, naphthyl and the like. Unless otherwise constrained by the definition for the aryl substituent, such aryl groups can optionally be substituted with from 1 to 5 substituents and preferably 1 to 3 substituents selected from the group consisting of hydroxy, acyl, alkyl, alkoxy, alkenyl, alkynyl, substituted alkyl, substituted alkoxy, substituted alkenyl, substituted alkynyl, amino, substituted amino, aminoacyl, acyloxy, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, trihalomethyl. Preferred substituents include alkyl, alkoxy, halo, cyano, nitro, trihalomethyl, and thioalkoxy.

As used herein, the term "cycloalkyl" refers to cyclic alkyl groups of from 3 to 12 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantyl, and the like.

As used herein, the terms "halo" or "halogen" refer to fluoro, chloro, bromo and iodo and preferably is either fluoro or chloro.

As used herein, the term "heteroaryl" refers to an aromatic carbocyclic group of from 1 to 15 carbon atoms and 1 to 4 heteroatoms selected from the group consisting of oxygen, nitrogen and sulfur within at least one ring (if there is more than one ring).

Unless otherwise constrained by the definition for the heteroaryl substituent, such heteroaryl groups can be optionally substituted with from 1 to 5 substituents and preferably 1 to 3 substituents selected from the group consisting of hydroxy, acyl, alkyl, alkoxy, alkenyl, alkynyl, substituted alkyl, substituted alkoxy, substituted alkenyl, substituted alkynyl, amino, substituted amino, aminoacyl, acyloxy, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO2-alkyl, —SO2-substituted alkyl, —SO2-aryl, —SO2-heteroaryl, and trihalomethyl. Preferred substituents include alkyl, alkoxy, halo, cyano, nitro, trihalomethyl, and thioalkoxy. Such heteroaryl groups can have a single ring (e.g., pyridyl or furyl) or multiple condensed rings (e.g., indolizinyl or benzothienyl).

"Heterocycle" or "heterocyclic" refers to a saturated or unsaturated carbocyclic group having a single ring or multiple condensed rings, from 1 to 15 carbon atoms and from 1 to 4 hetero atoms selected from the group consisting of nitrogen, sulfur and oxygen within the ring.

Unless otherwise constrained by the definition for the heterocyclic substituent, such heterocyclic groups can be optionally substituted with 1 to 5 substituents selected from the group consisting of alkyl, substituted alkyl, alkoxy, substituted alkoxy, aryl, substituted aryl, aryloxy, halo, nitro, heteroaryl, thiol, thioalkoxy, substituted thioalkoxy, thioaryloxy, trihalomethyl, and the like. Such heterocyclic groups can have a single ring or multiple condensed rings.

As to any of the above groups that contain 1 or more substituents, it is understood, of course, that such groups do not contain any substitution or substitution patterns which are sterically impractical and/or synthetically non-feasible.

As used herein, "carboxylic acid derivatives" and "sulfonic acid derivatives" refer to —C(X)—N($R^1$)$_2$, —C(X)O$R^1$, —C(X)S$R^1$, —SO$_n$$R^1$, —SO$_n$O$R^1$, —SO$_n$S$R^1$, or —SO$_n$—N($R^1$)$_2$, where X is O, S or N$R^1$, where $R^1$ is hydrogen, alkyl, substituted alkyl, aryl, or substituted aryl and activated derivatives thereof, such as anhydrides, esters, and halides such as chlorides, bromides and iodides, which can be used to couple the carboxylic acid and sulfonic acid derivatives to the 5'-amine using standard coupling chemistry.

"Pharmaceutically acceptable salts" refers to pharmaceutically acceptable salts of a compound of Formula I, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like can be used as the pharmaceutically acceptable salt.

The term "protecting group" or "blocking group" refers to any group which when bound to one or more hydroxyl, amino or carboxyl groups of the compounds (including intermediates thereof such as the aminolactams, aminolactones, etc.) prevents reactions from occurring at these groups and which protecting group can be removed by conventional chemical or enzymatic steps to reestablish the hydroxyl, amino or carboxyl group. Preferred removable amino blocking groups include conventional substituents such as t-butyoxycarbonyl (t-BOC), benzyloxycarbonyl (CBZ), and the like which can be removed by conventional conditions compatible with the nature of the product.

ABBREVIATIONS

The following abbreviations are used herein: [$^{125}$I]AB-MECA, [$^{125}$I]$N^6$-(4-amino-3-iodobenzyl)adenosine-5'N-methyluronamide;(R)-PIA, (R)-$N^6$-(phenylisopropyl)adenosine; DMSO, dimethysulfoxide; I-AB-MECA, $N^6$-(4-amino-3-iodobenzyl)adenosine-5'-N-methyluronamide; IB-MECA, $N^6$-(3-iodobenzyl)adenosine-5'-N-methyluronamide; Ki, equilibrium inhibition constant; NECA, 5'-N-ethylcarboxamido adenosine; THF, tetrahydrofuran; Tris, tris(hydroxymethyl)aminomethane.

Compound Preparation

Those skilled in the art of organic chemistry will appreciate that reactive and fragile functional groups often must be protected prior to a particular reaction, or sequence of reactions, and then restored to their original forms after the last reaction is completed. Usually groups are protected by converting them to a relatively stable derivative. For example, a hydroxyl group may be converted to an ether group and an amine group converted to an amide or carbamate. Methods of protecting and de-protecting, also known as "blocking" and "de-blocking," are well known and widely practiced in the art, e.g., see T. Green, *Protective Groups in Organic Synthesis*, John Wiley, New York (1981) or *Protective Groups in Organic Chemistry*, Ed. J. F. W. McOmie, Plenum Press, London (1973).

The compounds are preferably prepared by reacting a compound of Formula II below with a suitable carboxylic acid, sulfonic acid derivative, isocyanate of precursor of an isocyanate using known chemistry.

Compounds of Formula II can be prepared using the following Schemes I and II, illustrated where $R^3$ is furan.

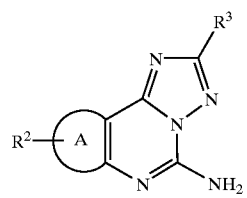

II

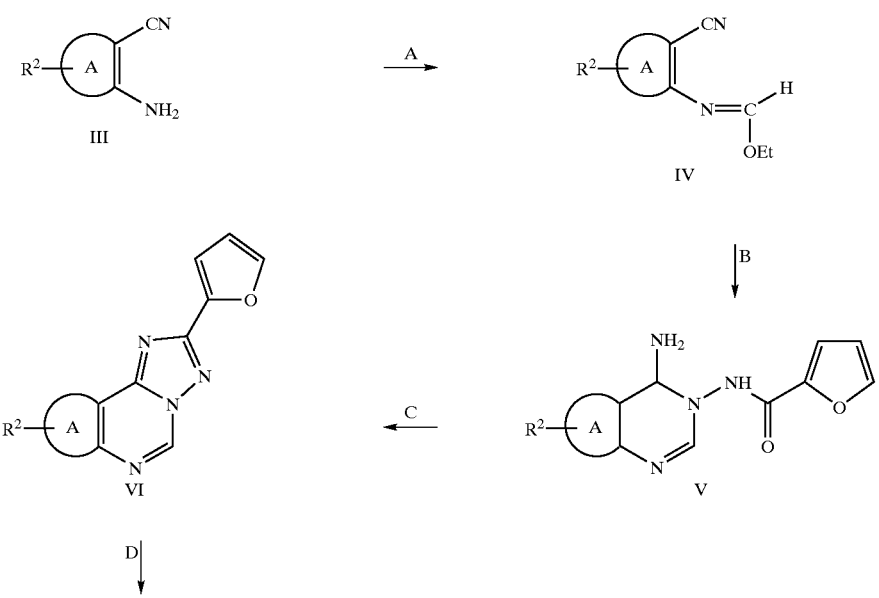

Scheme I

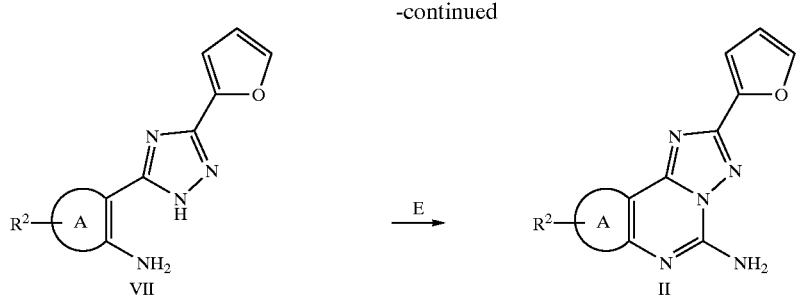

Reagents: A) triethyl orthoformate; B) 2-furoic acid hydrazide, 2-methoxyethanol; C) PhOPh, 260° C.; D) 10% HCl, under reflux; E) cyanamide, pTsOH, N-methylpyrrolidone Scheme II

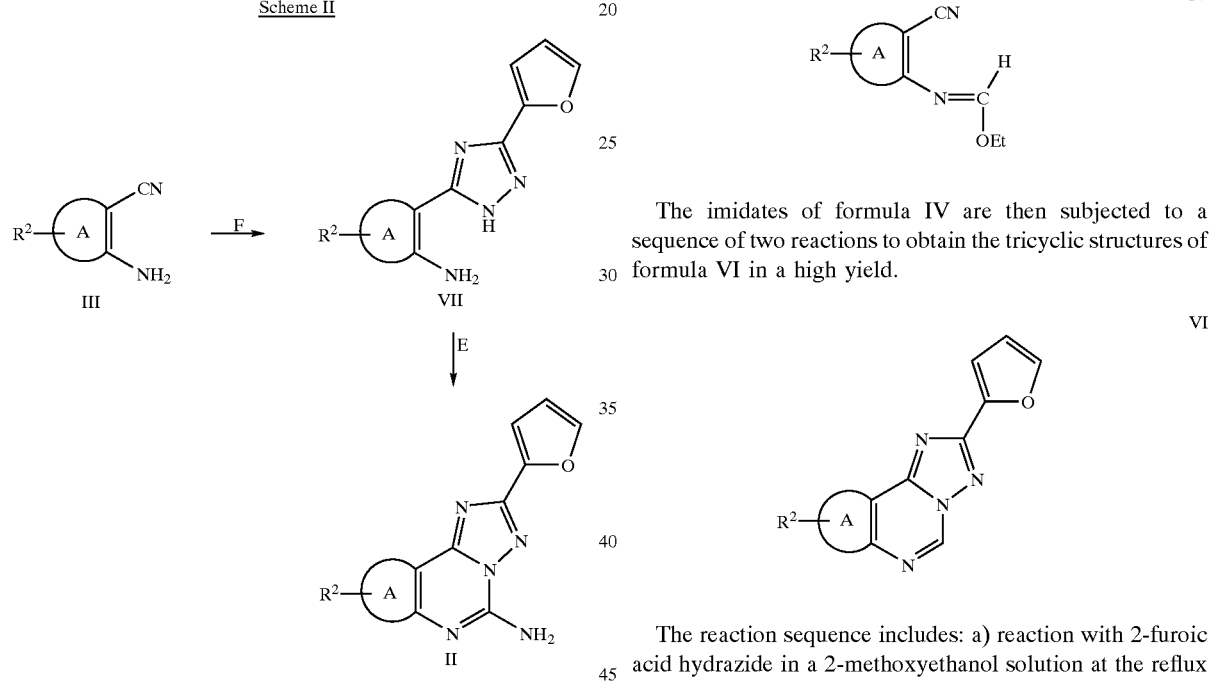

Reagents: F) furoic acid hydrazide, diphenyl ether; E) cyanamide, pTsOH, N-methylpyrrolidone.

The compounds of formula II can be prepared through either an indirect route described in Scheme I or a direct route described in Scheme II. Suitable starting materials for both schemes are the heterocyclic ortho-amino nitriles of formula III, generally prepared according to synthetic procedures known in literature and reported in the book by E. C. Taylor and A. McKillop (vol. 7 of the series Advances in Organic Chemistry, Ed. Interscience, 1970).

Ortho-amino nitriles (formula III) are transformed into the corresponding imidates of formula IV by reaction with an excess of ethyl orthoformate at the reflux temperature for 8 to 10 hours. The reaction, after evaporation of the ethyl orthoformate, leads to the substantially pure corresponding imidates IV in a high yield as evidenced by the IR and $^1$H NMR analysis on the crude reaction products.

The imidates of formula IV are then subjected to a sequence of two reactions to obtain the tricyclic structures of formula VI in a high yield.

The reaction sequence includes: a) reaction with 2-furoic acid hydrazide in a 2-methoxyethanol solution at the reflux temperature for 8–10 hours, to obtain the intermediate compounds of formula V; b) thermal cyclization of the latter to corresponding compounds of formula VI, by heating in diphenyl ether at the temperature of 260° C. for 0.5 to 1 hour.

The tricyclic compounds VI are then hydrolyzed with HCl at reflux for 1 to 3 hours to give triazoles VII, which are finally cyclized to desired compounds II with cyanamide in N-methylpyrrolidone at reflux and in the presence of para-toluenesulfonic acid (Scheme I).

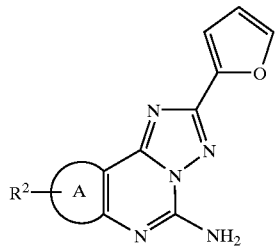

In some cases, triazoles VII can be obtained by directly heating in diphenyl ether ortho-amino nitrile III with 2-furoic acid hydrazide. Triazoles VII are then cyclized as described above in Scheme II. In the following schemes III, IV and V, the synthesis of the compounds of formula II in which A is a triazole ring are reported in more detail.

Scheme III
Synthesis of 5-amino-7-substituted-2-(2-furyl)-1,2,3-triazolo-[5,4-e]-1,2,4-triazolo[1,5-c]pyrimidine derivatives

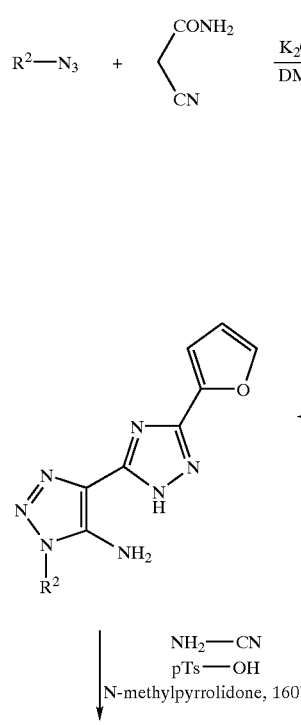

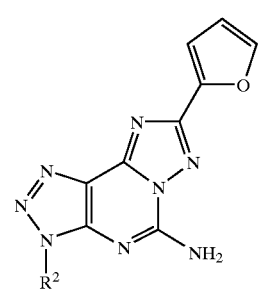

Scheme IV
Synthesis of 5-amino-8-substituted-2-(2-furyl)-1,2,3-triazolo[5,4-e]1,2,4-triazolo[1,5-c]pyrimidine derivatives

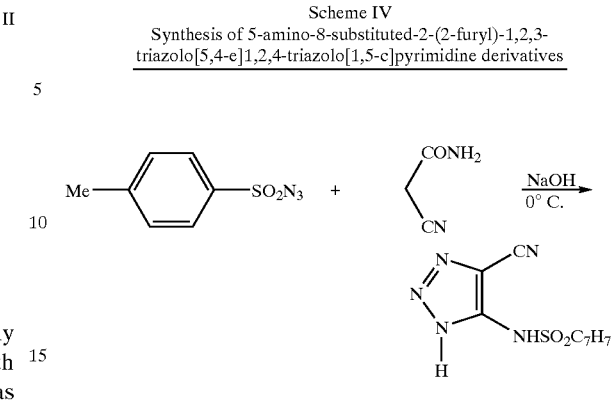

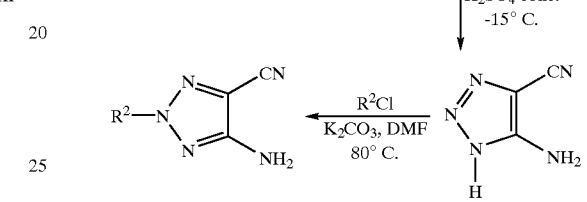

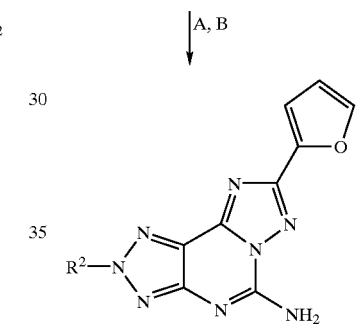

Reagents:

A) furoic acid hydrazide, PhOph, 260° C.,
B) $NH_2CN$, pTsOH, N-methylpyrrolidone.

Scheme V
Synthesis of 5-amino-9-substituted-2-(2-furyl)-1,2,3-triazolo[5,4-e]1,2,4-triazolo[1,5-c]pyrimidine derivatives

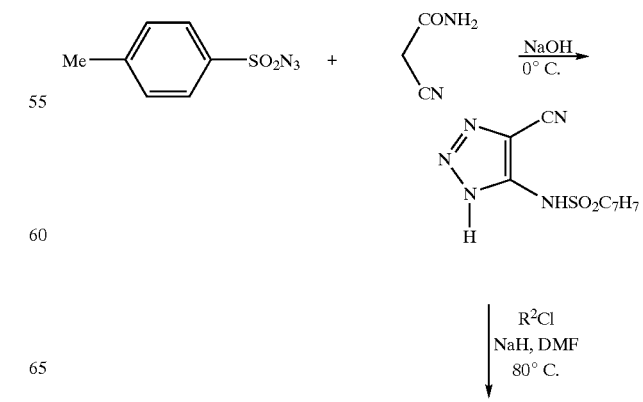

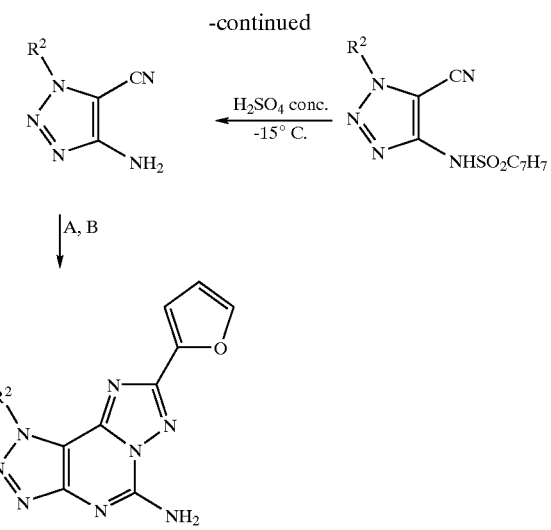

Reagents:
A) furoic acid hydrazide, PhOph, 260° C.,
B) NH₂CN, pTsOH, N-methylpyrrolidone.

Finally, the 5-amine-containing compounds 11 are reacted with carboxylic acids, sulfonic acids, activated carboxylic acids, activated sulfonic acids, thiocarboxylic acids, activated thiocarboxylic acids, isocyanates, isothiocyanates and the like, to form the desired compounds. Activated carboxylic acids include acid halides, esters, anhydrides and other derivatives known to react with amines to form amides. Activated sulfonic acids include sulfonyl halides such as sulfonyl chlorides.

It is not necessary in all cases to use activated carboxylic acid and sulfonic acid derivatives. The acids themselves can be coupled to the amines using standard coupling chemistry, for example, using dicyclohexyl diimide (DCI) and other routinely used coupling agents. Suitable coupling conditions for forming amide linkages are well known to those of skill in the art of peptide synthesis.

Similarly, it is not necessary in all cases to use the desired isocyanate or isothiocyanate directly. The desired isocyanate or isothiocyanate may be prepared in situ from the corresponding acyl azide by Curtius Rearrangement, well known to those skilled in the art. Alternatively the desired isocyanate or isothiocyanate may be prepared from the corresponding amide or thioamide by Hofmann Rearrangement, a method also known to those skilled in the art. In still another alternative, the desired isocyanate or isothiocyanate may be prepared in situ by a Lossen Rearrangement of the corresponding O-acyl hydroxamic acid or O-thioacyl hydroxamic acid.

Generally, the chemistry above can be used to prepare 8-(Ar)alkyl-2-(2-furyl)-pyrazolo[4,3-e]-1,2,4-triazolo[1,5-c]pyrimidines when 3-cyano-2-aminopyrazoles are used as starting materials. The 3-cyano-2-aminopyrazoles can be reacted with an alkyl halide (RX) in a polar aprotic solvent such as dimethyl formamide (DMF) to provide an R group on one of the ring nitrogens. The resulting compound can be refluxed with triethyl orthoformate to provide an imine ethyl ester, which can be reacted with furoic hydrazide, preferably using a Dean-Stark trap for the azeotropic elimination of water produced in the reaction, to provide 8-(Ar)alkyl-2-(2-furyl)-pyrazolo[4,3-e]-1,2,4-triazolo[1,5-c]pyrimidines. The products can be purified by chromatography, for example, in (EtOAc/hexane 1:1), for use in subsequent chemistry.

The product of this reaction can be reacted with a suitable acid, such as HCl, at reflux, followed by reaction with cyanamide in a solvent such as N-methylpyrrolidone with catalytic para-toluene sulfonic acid at elevated temperatures to provide 5-amino-8-(Ar)alkyl-2-(2-furyl)-pyrazolo[4,3-e]-1,2,4-triazolo[1,5-c]pyrimidines.

These amine-substituted compounds can be reacted with appropriate isocyanates to form urea compounds, activated carboxylic acids such as acid halides to provide amides, activated sulfonic acids such as sulfonic acid halides to form sulfonamides, or other reactive carboxylic acid or sulfonic acid derivatives to form other desired compounds. The isocyanates used to react with the amine-substituted compounds can be those commercially available or synthesized by means known in the art.

For example, the isocyanate 4-(N-morpholino)-phenyl isocyanate can be synthesized by reacting commercially available 4-morpholinoaniline with phosgene or diphosgene in an appropriate solvent. Similarly, the phenyl-isocyanates of a sulfonyl amine, sulfonyl piperazine, substituted sulfonyl amine or substituted sulfonyl piperazine can be synthesized by reacting the respective amine with diphosgene or phosgene. Benzene, ethyl acetate and the like are useful as the solvent in such reactions.

Other isocyanates can be prepared by first synthesizing the corresponding acyl azide and then forming the isocyanate during thermal decomposition. Such decomposition was originally reported by Curtius and further described by others (see, for example, R. Lo Scalzo et al., *Gazz. Chim. Ital.* 118, 819 (1988)). Acyl azides can be formed by contacting a hydrazide with a solution of sodium nitrite in hydrochloric acid.

Triazolo-triazolo-pyrimidine compounds can be prepared using similar chemistry, but starting with a suitably functionalized azide, and reacting the azide with 2-cyanoacetamide to form the initial heterocyclic ring, followed by reaction of the amide group with a dehydrating agent such as $POCl_3$ to form a nitrite. The resulting cyano-aminotriazole can be reacted in the same manner as the 3-cyano-2-aminopyrazoles discussed above to prepare triazolo-triazolo-pyrimidines.

Synthesis of Radiolabeled Analogues

The compounds can be labeled with any suitable radiolabel. Examples of suitable radiolabels include $^3H$ and $^{14}C$, but any substantially non-toxic radiolabel commonly used in pharmacokinetic studies can be used. Means for incorporating radiolabels into organic compounds are well known to those of skill in the art.

When the compounds are 5-[[substituted phenyl)amino] carbonyl]amino-8-(ar) alkyl-2-(2-furyl)-pyrazolo[4,3-e] 1,2,4-triazolo[1,5-c]pyrimidine compounds or 5-amino-8-(ar) alkyl-2-(2-furyl)-pyrazolo[4,3-e] 1,2,4-triazolo[1,5-c] pyrimidine compounds, incorporation of a tritium label is fairly straightforward.

In one embodiment, a suitable starting material is a compound in which the (ar)alkyl group at the 8-position includes a double bond. The double bond can be reacted with tritium in the presence a suitable catalyst, for example, palladium on charcoal or other known hydrogenation catalysts.

For example, 5-[[(4-methoxyphenyl)amino]carbonyl] amino-8-(1,2-ditritiopropyl)-2-(2-furyl)-pyrazolo[4,3-e] 1,2,4-triazolo[1,5-c] pyrimidine (radioligand of compound 108) can be prepared by adding tritium across the double bond of 5-[[(4-methoxyphenyl)amino]carbonyl]amino-8-(2-propen-1-yl)-2-(2-furyl)-pyrazolo[4,3-e] 1,2,4-triazolo[1,5-c] pyrimidine (compound 100). The radioligand of compound 108 is discussed below with respect to various binding affinity studies on JURKAT cancer cells.

Alternatively, the tritium label can be present on the compounds used to react with the 5-amino group to form the amides, ureas or other groups at the 5-position. For example, the isocyanates used to prepare the 5-aminocarbonylamino compounds described herein can include a tritium or other radiolabels, and can therefore be easily incorporated into the final product.

In another embodiment, the radiolabel can be incorporated into the molecule while the ring system is being put together. As discussed above with respect to the synthesis of the compounds of Formula II, various tricyclic compounds of Formula VI are hydrolyzed with HCl to give triazoles of Formula VII, which are cyclized to with cyanamide at reflux in the presence of para-toluenesulfonic acid, as shown in Scheme I. It is relatively straightforward to incorporate a $^{14}C$ label at this step in the synthesis using $^{14}C$ labeled cyanamide.

Iodinated compounds can be prepared, for example, by incorporating a radioactive iodine into the aromatic compound used to react with the 5-amine group. Incorporation of iodine into aromatic rings is well known to those of skill in the art. It is straightforward to incorporate an iodine atom into the aromatic compounds used to react with the 5-amine group to prepare the compounds described herein.

Accordingly, using no more than ordinary skill in the art, suitable radiolabeled analogues can readily be prepared.

Synthesis of Fluorescently-labeled Analogues

As with the radiolabeled compounds, the synthesis of fluorescently-labeled compounds is relatively straightforward. Preferably, the fluorescent groups are present at the $R^2$-position, although substitution at the $R^3$ position is also feasible. In one embodiment, the fluorescent group(s) include a furan ring which can be attached at the $R^3$ position. Alternatively, other aromatic rings can be used. Fluorescent labels are well known to those of skill in the art, and can readily be attached to the compounds described herein using known chemistry.

METHODS OF USING THE COMPOUNDS

The compounds can be used for all indications for which agonists and antagonists of the $A_3$ receptor may be used, including:
 treating hypertension;
 treating inflammatory disorders such as rheumatoid arthritis and psoriasis;
 treating allergic disorders such as hay fever and allergic rhinitis;
 mast cell degranulation;
 antitumor agents;
 treating cardiac hypoxia; and
 protection against cerebral ischemia;
as described, for example, in Jacobson, TIPS May 1998, pp. 185–191, the contents of which are hereby incorporated by reference.

A preferred use for these compounds is in the detection and/or treatment of cancer. As discussed below, tumor cells have been shown to express the $A_3$ receptor. It is believed that the $A_3$ receptor protects the cells from ischemic damage when they do not receive an adequate blood supply. However, agonism of the adenosine $A_3$ receptors can bring about a protective effect, preventing tumor cell death while the cells are not receiving an adequate blood supply. By administering antagonists of these receptors the protective effect that $A_3$ receptors provide will be lost.

The compounds can be administered to a patient via any medically acceptable means. Suitable means of administration include oral, rectal, topical or parenteral (including subcutaneous, intramuscular and intravenous) administration, although oral or parenteral administration are preferred.

The amount of the compound required to be effective as a modulator of an adenosine receptor will, of course, vary with the individual mammal being treated and is ultimately at the discretion of the medical or veterinary practitioner. The factors to be considered include the condition being treated, the route of administration, the nature of the formulation, the mammal's body weight, surface area, age and general condition, and the particular compound to be administered. However, a suitable effective dose is in the range of about 0.1 µg/kg to about 10 mg/kg body weight per day, preferably in the range of about 1 mg/kg to about 3 mg/kg per day.

The total daily dose may be given as a single dose, multiple doses, e.g., two to six times per day, or by intravenous infusion for a selected duration. Dosages above or below the range cited above are within the scope of the present invention and may be administered to the individual patient if desired and necessary. For example, for a 75 kg mammal, a dose range would be about 75 mg to about 220 mg per day, and a typical dose would be about 150 mg per day. If discrete multiple doses are indicated, treatment might typically be 50 mg of a compound given 3 times per day.

In another embodiment, the radiolabeled compounds can be administered to a patient for purposes of performing an assay to determine the presence or absence of cancerous tumor cells expressing $A_3$ receptors. The compounds described herein as having a relatively high affinity for the $A_3$ receptor subtype are advantageously administered to a patient, and after the compounds bind to the $A_3$ receptors present in the tumor cells, the location of the tumor cells can be determined by determining the location of the radiolabeled compounds. Devices for determining the location and density of radiolabeled compounds are well known to those of skill in the art.

The use of radiolabeled and/or fluorescently labeled compounds during surgery for removal of cancerous tissue can also be advantageous. Often, surgeons need to ensure complete removal of the cancerous tissue. The radiolabeled or fluorescently labeled compounds can be administered to a patient either before or during the surgery, and will bind to the cancer cells present in the patient. The time of administration will vary, depending, among other factors, on the uptake of the particular compound for the particular tumor cells, and the location of the tumor in the body. The surgeon then has a relatively straightforward assay for determining the presence of residual cancer cells after removing the tumor. The presence of residual tumor cells can be determined by measuring fluorescence or radioactivity at the operative site, using analytical devices well known to those of skill in the art.

Detection of cancer cells in vitro can be performed by administering the compounds to a suspension of cells in cell culture media, allowing the compound to bind to the adenosine $A_3$ receptors on the cancer cells, and detecting the label.

Formulations

The compounds described above are preferably administered in formulation including an active compound, i.e., a compound of formula I, together with an acceptable carrier for the mode of administration. Suitable pharmaceutically acceptable carriers are known to those of skill in the art.

The compositions can optionally include other therapeutically active ingredients such as antivirals, antitumor agents, antibacterials, anti-inflammatories, analgesics, and immunosuppresants. The carrier must be pharmaceutically acceptable in the sense of being compatible with the other ingredients of the formulation and not deleterious to the recipient thereof.

The formulations can include carriers suitable for oral, rectal, topical or parenteral (including subcutaneous, intramuscular and intravenous) administration. Preferred carriers are those suitable for oral or parenteral administration.

Formulations suitable for parenteral administration conveniently include sterile aqueous preparation of the active compound which is preferably isotonic with the blood of the recipient. Thus, such formulations may conveniently contain distilled water, 5% dextrose in distilled water or saline. Useful formulations also include concentrated solutions or solids containing the compound of formula (I) which upon dilution with an appropriate solvent give a solution suitable for parental administration.

For enteral administration, the compound can be incorporated into an inert carrier in discrete units such as capsules, cachets, tablets or lozenges, each containing a predetermined amount of the active compound; as a powder or granules; or a suspension or solution in an aqueous liquid or non-aqueous liquid, e.g., a syrup, an elixir, an emulsion or a draught. Suitable carriers may be starches or sugars and include lubricants, flavorings, binders, and other materials of the same nature.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine, a mixture of the powdered active compound with any suitable carrier.

A syrup or suspension may be made by adding the active compound to a concentrated, aqueous solution of a sugar, e.g., sucrose, to which may also be added any accessory ingredients. Such accessory ingredients may include flavoring, an agent to retard crystallization of the sugar or an agent to increase the solubility of any other ingredient, e.g., as a polyhydric alcohol, for example, glycerol or sorbitol.

The compounds can also be administered locally by topical application of a solution, ointment, cream, gel, lotion or polymeric material (for example, a Pluronic™, BASF), which may be prepared by conventional methods known in the art of pharmacy. In addition to the solution, ointment, cream, gel, lotion or polymeric base and the active ingredient, such topical formulations may also contain preservatives, perfumes, and additional active pharmaceutical agents.

Formulations for rectal administration may be presented as a suppository with a conventional carrier, e.g., cocoa butter or Witepsol S55 (trademark of Dynamite Nobel Chemical, Germany), for a suppository base.

Alternatively, the compound may be administered in liposomes or microspheres (or microparticles). Methods for preparing liposomes and microspheres for administration to a patient are well known to those of skill in the art. U.S. Pat. No. 4,789,734, the contents of which are hereby incorporated by reference, describes methods for encapsulating biological materials in liposomes. Essentially, the material is dissolved in an aqueous solution, the appropriate phospholipids and lipids added, along with surfactants if required, and the material dialyzed or sonicated, as necessary. A review of known methods is provided by G. Gregoriadis, Chapter 14, "Liposomes," *Drug Carriers in Biology and Medicine*, pp. 287–341 (Academic Press, 1979). Microspheres formed of polymers or proteins are well known to those skilled in the art, and can be tailored for passage through the gastrointestinal tract directly into the blood stream. Alternatively, the compound can be incorporated and the microspheres, or composite of microspheres, implanted for slow release over a period of time ranging from days to months. See, for example, U.S. Pat. Nos. 4,906,474, 4,925,673 and 3,625,214, the contents of which are hereby incorporated by reference.

Preferred microparticles are those prepared from biodegradable polymers, such as polyglycolide, polylactide and copolymers thereof. Those of skill in the art can readily determine an appropriate carrier system depending on various factors, including the desired rate of drug release and the desired dosage.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier or a finely divided solid carrier and then, if necessary, shaping the product into a desired unit dosage form.

In addition to the aforementioned ingredients, the formulations may further include one or more optional accessory ingredient(s) utilized in the art of pharmaceutical formulations, e.g., diluents, buffers, flavoring agents, binders, surface active agents, thickeners, lubricants, suspending agents, preservatives (including antioxidants) and the like.

Determination of the Degree of Activity for the Compounds

The activity of the compounds can be readily determined using no more than routine experimentation using any of the following assays.

Rat $A_1$ and $A_{2A}$ Adenosine Receptor Binding Assay

Membrane Preparations:

Male Wistar rats (200–250 g) can be decapitated and the whole brain (minus brainstem, striatum and cerebellum) dissected on ice. The brain tissues can be disrupted in a Polytron (setting 5) in 20 vols of 50 mM Tris HCl, pH 7.4. The homogenate can then be centrifuged at 48,000 g for 10 min and the pellet resuspended in Tris-HCL containing 2 IU/ml adenosine deaminase, type VI (Sigma Chemical Company, St. Louis, Mo., USA). After 30 min incubation at 37° C., the membranes can be centrifuged and the pellets stored at −70° C. Striatal tissues can be homogenized with a Polytron in 25 vol of 50 mM Tris HCL buffer containing 10 mM $MgCl_2$ pH 7.4. The homogenate can then be centrifuged at 48,000 g for 10 min at 4° C. and resuspended in Tris HCl buffer containing 2 IU/ml adenosine deaminase. After 30 min incubation at 37° C., membranes can be centrifuged and the pellet stored at −70° C.

Radioligand Binding Assays:

Binding of [$^3$H]-DPCPX (1,3-dipropyl-8-cyclopentylxanthine) to rat brain membranes can be performed essentially according to the method previously described by Bruns et al., Proc. Natl, Acad. Sci. 77, 5547–5551 1980. Displacement experiments can be performed in 0.25 ml of buffer containing 1 nM [$^3$H]-DPCPX, 100 µl of diluted membranes of rat brain (100 µg of protein/assay) and at least 6–8 different concentrations of examined compounds. Non specific binding can be determined in the presence of 10 µM of CHA (N$^6$cyclohexyladenosine) and this is always ≦10% of the total binding. Incubation times are typically 120 min at 25° C.

Binding of [$^3$H]-SCH 58261 (5-amino-7-(2-(phenyl)ethyl)-2-(2-furyl)-pyrazolo[4,3-e]-1,2,4-triazolo[1,5-c]pyrimidine) to rat striatal membranes (100 µg of protein/assay) can be performed according to methods described in Zocchi et al., J. Pharm. and Exper. Ther. 276:398–404 (1996). In competition studies, at least 6–8 different concentrations of examined compounds should be used. Non specific binding can be determined in the presence of 50 µM of NECA (5'-(N-ethylcarboxamido)adenosine). Incubation time is typically 60 min at 25° C.

Bound and free radioactivity can be separated by filtering the assay mixture through Whatman GF/B glass-fiber filters using a Brandel cell harvester (Gaithersburg, Md., USA). The incubation mixture can be diluted with 3 ml of ice-cold incubation buffer, rapidly vacuum filtered and the filter can be washed three times with 3 ml of incubation buffer. The filter bound radioactivity can be measured, for example, by liquid scintillation spectrometry. The protein concentration can be determined, for example, according to a Bio-Rad method (Bradford, Anal. Biochem. 72:248 (1976)) with bovine albumin as reference standard.

Human Cloned A$_3$ Adenosine Receptor Binding Assay

Receptor Binding Assays:

Binding assays can be carried out according to methods described in Salvatore et al., Proc. Natl. Acad. Sci. 90:10365–10369 (1993). In saturation studies, an aliquot of membranes (8 mg protein/ml) from HEK-293 cells transfected with the human recombinant A$_3$ adenosine receptor (Research Biochemical International, Natick, Mass., USA) can be incubated with 10–12 different concentrations of [$^{125}$I]AB-MECA ranging from 0.1 to 5 nM. Competition experiments can be carried out in duplicate in a final volume of 100 µl in test tubes containing 0.3 nM [$^{125}$I]AB-MECA, 50 mM Tris HCL buffer, 10 mM MgCl$_2$, pH 7.4 and 20 µl of diluted membranes (12.4 mg protein/ml) and at least 6–8 different concentrations of examined ligands.

Incubation time was 60 min at 37° C., according to the results of previous time-course experiments. Bound and free radioactivity were separated by filtering the assay mixture through Whatman GF/B glass-fiber filters using a Brandel cell harvester. Non-specific binding was defined as binding in the presence of 50 µM R-PIA and was about 30% of total binding. The incubation mixture was diluted with 3 ml of ice-cold incubation buffer, rapidly vacuum filtered and the filter was washed three times with 3 ml of incubation buffer. The filter bound radioactivity was counted in a Beckman gamma 5500B γ counter. The protein concentration can be determined according to a Bio-Rad method (3) with bovine albumin as reference standard.

Data Analysis

Inhibitory binding constant, $K_i$, values can be calculated from those of IC$_{50}$ according to the Cheng & Prusoff equation (Cheng and Prusoff, Biochem. Pharmacol. 22:3099–3108 (1973)), $K_i$=IC$_{50}$/(1+[C*]/K$_D$*), where [C*] is the concentration of the radioligand and K$_D$* its dissociation constant.

A weighted non linear least-squares curve fitting program LIGAND (Munson and Rodbard, Anal. Biochem. 107:220–239 (1990)) can be used for computer analysis of saturation and inhibition experiments. Data are typically expressed as geometric mean, with 95% or 99% confidence limits in parentheses.

CHO Membranes Preparation

The expression of the human A$_1$, A$_{2A}$, A$_{2B}$ and A.sub.3 receptors in CHO cells has been previously described (Klotz et al., 1998). The cells are grown adherently and maintained in Dulbecco's modified Eagle's medium with nutrient mixture F12 without nucleosides at 37.degree. C. in 5% CO$_2$/95% air. Cells are split two or three times weekly and then the culture medium is removed for membrane preparations. The cells are washed with phosphate-buffered saline and scraped off flasks in ice cold hypotonic buffer (5 mM Tris HCl, 2 mM EDTA, pH 7.4). The cell suspension is homogenized with Polytron and the homogenate is centrifuged for 30 min. at 48,000 g. The membrane pellet is re-suspended in 50 mM Tris HCl buffer at pH 7.4 for A$_1$ adenosine receptors, in 50 mM Tris HCl, 10 mM MgCl$_2$ at pH 7.4 for A$_{2A}$ adenosine receptors, in 50 mM Tris HCl, 10 mM MgCl$_2$, 1 mM EDTA at pH 7.4 for A$_3$ adenosine receptors and are utilized for binding and adenylate cyclase assays.

Human Cloned A$_1$, A$_{2A}$, A$_{2B}$ and A$_3$ Adenosine Receptor Binding Assay Binding of [$^3$H]-DPCPX to CHO cells transfected with the human recombinant A$_1$ adenosine receptor is performed according to the method previously described by Klotz and coworkers (Klotz, K. N.; Cristalli, G.; Grifantini, M.; Vittori, S.; Lohse, M. J., "Photoaffinity labeling of A1 adenosine receptors," J. Biol. Chem., 260, 14659–14664,1985).

Displacement experiments are performed for 120 min. at 25° C. in 0.20 mL of buffer containing 1 nM [$^3$H]-DPCPX, 20 µL of diluted membranes (50 µg of protein/assay) and at least 6–8 different concentrations of examined compounds. Non-specific binding is determined in the presence of 10 µM of CHA and this is always 10% of the total binding. Binding of [$^3$H]-SCH58261 to CHO cells transfected with the human recombinant A$_{2A}$ adenosine receptors (50 µg of protein/assay) was performed according to Varani et al. (Varani, K; Cacciari, B.; Baraldi, P. G.; Dionisotti, S.; Ongini, E.; Borea, P. A., "Binding affinity of adenosine receptor agonists and antagonists at human cloned A$_3$ adenosine receptors," Life Sci., 63, 81–87,1998). In competition studies, at least 6–8 different concentrations of compounds are used and non-specific binding is determined in the presence of 50 µM NECA for an incubation time of 60 min. at 25° C.

Binding of [.sup.3 H]-DPCPX to HEK-293 cells (Receptor Biology, Inc., Beltsville, Md.) transfected with the human recombinant A2B adenosine receptors is performed essentially to the method described by Varani and coworkers (Mol. Pharmacol.). In particular, assays are carried out for 60 min. at 25° C. in 0.1 mL of 50 mM Tris HCl Buffer, 10 mM MgCl.sub.2, 1 mM EDTA, 0.1 mM benzamidine pH 7.4, 2 IU/ml adenosine deaminase containing 40 nM [.sup.3 H]-DPCPX, diluted membranes (20.mu.g of protein/assay) and at least 6–8 different concentration of tested compounds. Non-specific binding is determined in the presence of 100 µM of NECA and is always 30% of the total binding.

Binding of [³H] MRE3008-F20 (radioligand of Compound 108) to CHO cells transfected with the human recombinant A₃ adenosine receptors was performed according to Varani et al. (Mol. Pharmacol.). Competition experiments are carried out in duplicate in a final volume of 250 μL in test tubes containing 1 nM [³H] MRE3008-F20, 50 mM Tris HCl buffer, 10 mM $MgCl_2$, pH 7.4 and 100 μL of diluted membranes (50.mu.g of protein/assay) and at least 6–8 different concentrations of examined ligands. Incubation time was 120 min. at 40° C., according to the results of previous time-course experiments (Mol. Pharmacol.). Nonspecific bindings is defined as binding in the presence of 1 μM of MRE3008-F20 and is about 25% of total binding. Bound and free radioactivity are separated by filtering the assay mixture through Whatman GF/B glass-fiber filters using a Micro-mate 196 cell harvester (Packard Instrument Company). The filter bound radioactivity is counted on Top Count (efficiency 57%) with Micro-Scint 20. The protein concentration is determined according to a BioRad method (Bradford, M. M., "A rapid and sensitive method for the quantification of microgram quantities of protein utilizing the principle of protein dye-binding," Anal. Biochem. 72, 248, 1976) with bovine albumin as reference standard.

Adenylate Cyclase Assay

Membrane preparation is suspended in 0.5 mL of incubation mixture (50 mM Tris HCl, $MgCl_2$ 10 mM, EDTA, 1 mM, pH 7.4) containing GTP 5 .mu.M, 0.5 mM 4-(3-buthoxy-4-methoxybenzyl)-2-imidazolidinone (Ro 20-1274) as phosphodiesterase inhibitor, 2.0 IU/mL adenosine deaminase and pre-incubated for 10 min. in a shaking bath at 37° C. The IB-MECA or antagonists examined plus ATP (1 mM) and forskolin 10 μM are added to the mixture and the incubation continued for a further 10 min. The potencies of antagonists were determined by antagonism of the IB-MECA (100 nM)-induced inhibition of cyclic AMP (cAMP) production. The reaction is terminated by transferring to a boiling water bath. Boiling is for 2 min., and then the tubes are cooled to room temperature and centrifuged at 2,000 g for 10 min. at 4° C. Supernatants (100 μL) are used in competition protein binding assay carried out essentially according to Varani et al. (Mol. Pharmacol. 2000).

Samples of cAMP standards (0–10 pmol) are added to each test tube containing the incubation buffer (trizma base 0.1 M; aminophylline 8.0 mM; 2-mercaptoethanol 6.0 mM, pH 7.4) and [³H]-cAMP in a total volume of 0.5 mL. The binding protein, previously prepared from beef adrenals, is added to the samples previously incubated at 4° C. for 150 min. and, after the addition of charcoal are centrifuged at 2,000 g for 10 min. The clear supernatant (0.2 mL) is mixed with 4 mL of atomlight in a LS-1800 Beckman scintillation counter.

EXAMPLES

The following examples illustrate aspects of this invention but should not be construed as limitations. The symbols and conventions used in these examples are intended to be consistent with those used in the contemporary, international, chemical literature, for example, the *Journal of the American Chemical Society* ("*J. Am. Chem. Soc.*") and *Tetrahedron*.

Example 1

Preparation of 8-(Ar)alkyl-2-(2-furyl)-pyrazolo[4,3-e]1,2,4-triazolo[1,5-c]pyrimidines (Compounds 18–25)

8-(Ar)alkyl-2-(2-furyl)-pyrazolo[4,3-e] 1,2,4-triazolo[1,5-c]pyrimidines were prepared according to the synthetic strategy shown in the following Scheme VI.

Scheme VI
General procedures for the preparation of 8-(Ar)alkyl-2-(2-furyl)-pyrazolo[4,3-e]1,2,4-triazolo[1,5-c]pyrimidine (18-25)

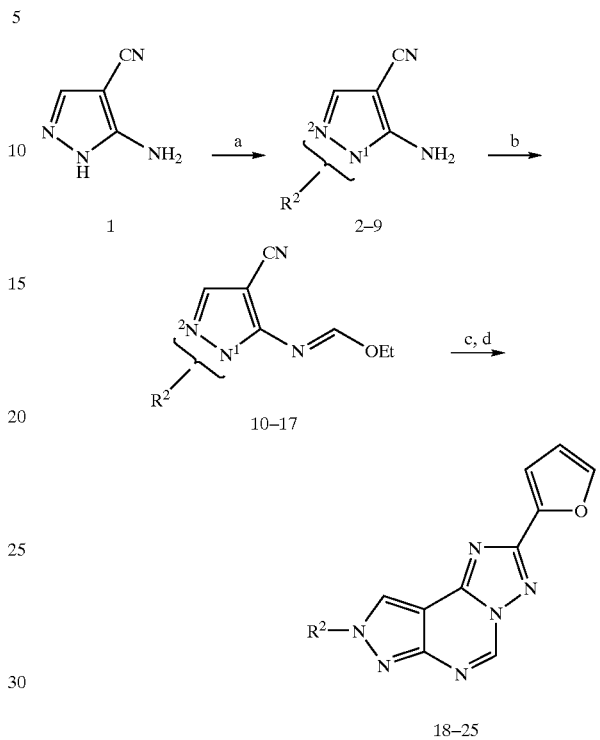

Reagents: a) NaH, DMF, $R^2X$; b) $HC(OEt)_3$, reflux; c) 2-Furoic hydrazide, $MeO(CH_2)_2OH$; d) $Ph_2O$, 260° C., flash chromatography In the preparation of compounds 18–25, a solution of Compound 1 (10 mmol) in 40 ml of DMF cooled to 0° C. was treated with NaH (60% in oil, 12 mmol) in several portions over 10 minutes. After 45 minutes, the appropriate (ar)alkyl halide (12 mmol), was added and the reaction mixture was allowed to warm to 25° C. and stirred for 3–5 hours (TLC: EtOAc 1:1). The reaction was quenched by addition of $H_2O$ (80 ml), and the aqueous layer was extracted with EtOAc (5×25 ml). The organic layers were recombined, dried ($Na_2SO_4$), filtered and concentrated at reduced pressure, to afford the alkylated pyrazole (Compounds 2–9) as inseparable mixture of $N^1$ and $N^2$ isomers (ratio approximately 1:4). This mixture of $N^1$ and $N^2$-substituted-4-cyano-5-amino pyrazoles (Compounds 2–9) was then dissolved in triethyl orthoformate (60 ml) and the solution was refluxed under nitrogen for 8 hours. The solvent was then removed under vacuum and the oily residue constituted by the mixture of imidates (Compounds 10–17) was dissolved in 2-methoxyethanol (50 ml) and 2-furoic acid hydrazide (13 mmol) was added. The mixture was refluxed for 5–10 hours, then, after cooling, the solvent was removed under reduced pressure and the dark oily residue was cyclized further in diphenyl ether (50 ml) using a Dean-Stark apparatus for the azeotropic elimination of water produced in the reaction. After 1.5 hours, the mixture was cooled and poured onto hexane (300 ml). The precipitate was collected by filtration and purified by chromatography (EtOAc/hexane 1:1). In this way, the major product ($N^8$ alkylated) (Compounds 18–25) are obtained in a good overall yield.

Following this general procedure the following compounds have been prepared:

8-Methyl-2-(2-furyl)-pyrazolo[4,3-e]1,2,4-triazolo[1,5-c]pyrimidine (Compound 18) yield 45%; yellow solid, m.p. 155–156° C. (EtOAc-light petroleum); IR (KBr): 1615, 1510 cm$^{-1}$; $^1$H NMR (DMSO-d$_6$) δ 4.1 (s, 1H); 6.32 (m, 1H); 7.25 (m, 1H); 8.06 (m, 1H); 8.86 (s, 1H), 9.38 (s, 1H).

8-Ethyl-2-(2-furyl)-pyrazolo[4,3-e] 1,2,4-triazolo[1,5-c]pyrimidine (Compound 19) yield 50%; pale yellow solid m.p. 188–189° C. (EtOAc-light petroleum); IR (KBr): 1620, 1500 cm$^{-1}$; $^1$H NMR (DMSO-d$_6$) δ 1.67 (t, 2H, J=7); 4.53 (q, 2H, J=7); 6.59 (m, 1H); 7.23 (m, 1H); 7.64 (s, 1H); 8.34 (s, 1H); 9.10 (s, 1H).

8-Propyl-2-(2-furyl)-pyrazolo[4,3-e] 1,2,4-triazolo[1,5-c]pyrimidine (Compound 20) yield 60%; yellow solid m.p. 189–190° C. (EtOAc-light petroleum); IR (KBr): 1600, 1505 cm$^{-1}$; $^1$H NMR (DMSO-d$_6$) δ 0.98 (t, 2H, J=7); 2.03–2.10 (m, 2H); 4.41 (q, 2H, J=7); 6.60 (m, 1H); 7.24 (m, 1H); 7.64 (s, 1H); 8.32 (s, 1H); 9.10 (s, 1H).

8-Butyl-2-(2-turyl)-pyrazolo[4,3-e] 1,2,4-triazolo[1,5-c]pyrimidine (Compound 21) yield 50%, pale yellow solid m.p. 245–247° C. (EtOAc-light petroleum); IR (KBr): 1610, 1500 cm$^1$; $^1$H NMR (DMSO-d$_6$) δ 0.9 (m, 3H); 1.3 (m, 2H); 1.9 (m, 2H); 4.5 (t. 2H, J=7.2); 6.2 (m, 1H); 7.3 (m, 1H); 8.0 (m, 1H); 8.9 (s, 1H); 9.4 (s, 1H).

8-Isopentyl-2-(2-furyl)-pyrazolo[4,3-e] 1,2,4-triazolo[1,5-c]pyrimidine (Compound 22) yield 54%; pale yellow solid m.p. 235–237° C. (EtOAc-light petroleum); IR (KBr): 1635, 1510, 1450 cm$^1$; $^1$H NMR (DMSO-d$_6$) δ 1.0 (d, 6H, J=6.2); 1.5–1.9 (m, 3H); 4.6 (t, 2H, J=7.4); 6.6 (m, 1H), 7.3 (m, 1H); 7.7 (m, 1H); 8.8 (s, 1H); 9.1 (s, 1H).

8-(2-Isopentenyl)-2-(2-furyl)-pyrazolo[4,3-e] 1,2,4-triazolo[1,5-c]pyrimidine (Compound 23) yield 48%; yellow solid m.p. 210–212° C. (EtOAc-light petroleum); IR (KBr): 1625, 1500, 1430 cm$^{-1}$; $^1$H NMR (DMSO-d$_6$) δ 1.79 (s, 3H); 1.87 (s, 3H); 5.05 (d, 2H, J=6); 5.55–5.63 (m, 1H); 6.60 (m, 1H); 7.24 (m, 1H); 7.64 (s, 1H) 8.34 (s, 1H); 9.10 (s, 1H).

8-(2-(phenyl)ethyl)-2-(2-furyl)-pyrazolo[4,3-e] 1,2,4-triazolo [1,5-c]pyrimidine (Compound 24) yield 56%, m.p. 268–270° C.; (EtOAc-Light petroleum); IR (KBr): 1660, 1510, 1450 cm$^{-1}$; $^1$H NMR (DMSO-d$_6$) δ 3.32 (t, 2H, J=6.7); 4.72 (t, 2H, J=6.7); 6.73 (s, 1H); 7.23 (m, 5H); 7.95 (s, 1H); 8.8 (s, 1H); 9.41 (s, 1H). Anal. (C$_{18}$H$_{14}$N$_6$O)C, H, N.

8-(3-(phenyl)propyl)-2-(2-furyl)-pyrazolo[4,3-e] 1,2,4-triazolo [1,5-c]pyrimidine (Compound 25) yield 63%; yellow solid m.p. 165–166° C. (EtOAc-light petroleum); IR (KBr): 1630, 1500, 1440 cm$^{-1}$; $^1$H NMR (DMSO-d$_6$) δ 2.34–2.48 (m, 2H); 2.67 (t, 3H, J=7.5); 4.43 (t, 2H, J=7.5), 6.61 (m, 1H); 7.16–7.32 (m, 6H); 7.64 (d, 1H, J=2); 8.29 (s, 1H); 9.02 (s, 1H).

Example 2

Preparation of 5-Amino-8-(ar)alkyl-2-(2-furyl)-pyrazolo[4,3-e] 1,2,4-triazolo[1,5-c]pyrimidines (Compounds 33–40)

5-Amino-8-(ar)alkyl-2-(2-furyl)-pyrazolo[4,3-e] 1,2,4-triazolo[1,5-c]pyrimidines can be prepared according to the synthetic strategy shown in the following Scheme VII.

Scheme VII
General procedures for the preparation of 5-Amino-8-(ar)alkyl-2-(2-furyl)-pyrazolo[4,3-e] 1,2,4-triazolo[1,5-c]pyrimidine (Compounds 34-41)

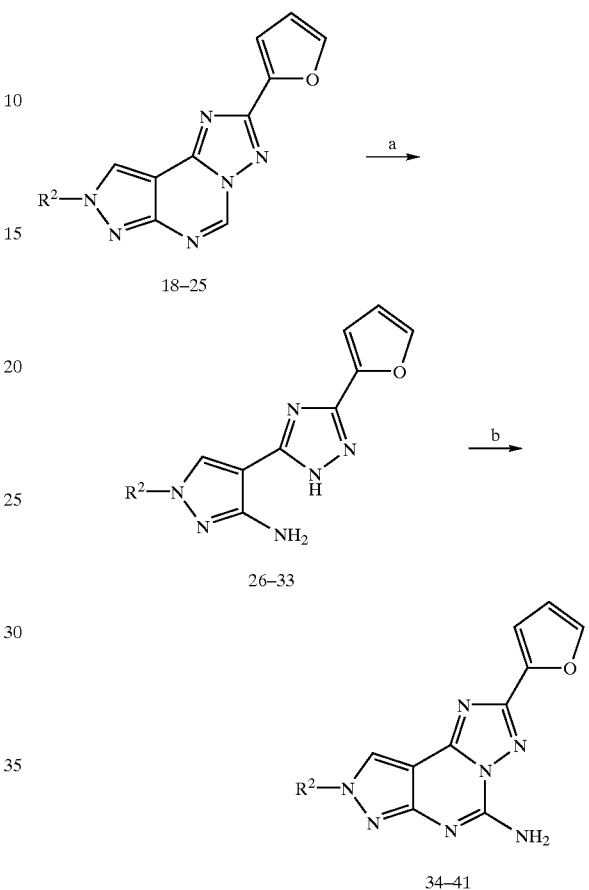

Reagents: a) HCl, reflux; b) NH$_2$CN, 1-methyl-2-pyrrolidone, pTsOH, 140° C.

In the preparation of compounds 34–41, a solution of the mixture of pyrazolo-triazolo-pyrimidine (Compounds 18–25) (10 mmol) in aqueous 10% HCl (50 ml) was refluxed for 3 hours. Then the solution was cooled and neutralized with a saturated solution of NaHCO$_3$ at 0° C. The compounds Compounds (26–33) were extracted with EtOAc (3×20 ml), the organic layers were dried with Na$_2$SO$_4$ and evaporated under vacuum. The obtained crude amine (Compounds 26–33) was dissolved in N-methylpyrrolidone (40 ml), cyanamide (60 mmol) and p-toluene sulfonic acid (15 mmol) were added and the mixture was heated at 160° C. for 4 hours. After cooling, cyanamide (60 mmol) was added again and the solution was heated overnight. Then the solution was diluted with EtOAc (80 ml) and the precipitate (excess of cyanamide) was collected by filtration; the filtrate was concentrated under reduced pressure and washed with water (3×30 ml). The organic layer was dried (Na$_2$SO$_4$) and evaporated under vacuum. The residue was purified by chromatography (EtOAc/light petroleum 2:1) to afford the desired product (Compounds 34–41) as a solid.

Following this general procedure the following compounds have been prepared:

5-Amino-8-methyl-2-(2-furyl)-pyrazolo[4,3-e] 1,2,4-triazolo[1,5-c]pyrimidine (Compound 34) yield 53%; yellow solid m.p. 167–168° C. (EtOAc-light petroleum); IR (KBr): 3500–2950, 1680, 1645, 1610, 1560, 1455 cm⁻¹; ¹H NMR (DMSO-d₆) δ 4.12 (s, 3H); 6.70 (m, 1H); 6.99 (bs, 2H); 7.18 (m, 1H); 7.81 (s, 1H), 8.42 (s, 1H).

5-Amino-8-ethyl-2-(2-furyl)-pyrazolo[4,3-e] 1,2,4-triazolo[1,5-c]pyrimidine (Compound 35) yield 65%,- yellow solid m.p. 249–250° C. (EtOAc-light petroleum); IR (KBr): 3430–2950, 1680, 1655, 1620, 1550, 1450 cm⁻¹; ¹H NMR (DMSO-d₆) δ 1.46 (t, 2H, J=7); 4.30 (d, 2H, J=7); 6.72 (m, 1H); 7.18 (m, 1H); 7.93 (bs, 2H); 7.93 (s, 1H); 8.62 (s, 1H).

5-Amino-8-propyl-2-(2-furyl)-pyrazolo[4,3-e] 1,2,4-triazolo[1,5-c]pyrimidine (Compound 36) yield 57%; pale yellow solid m.p. 209–210° C. (EtOAc-light petroleum); IR (KBr): 3400–2900, 1660, 1645, 1610, 1545, 1430 cm⁻¹; ¹H NMR (DMSO-d₆) 60.83 (t, 2H, J=7); 1.81–1.91 (m, 2H); 4.22 (d, 2H, J=7); 6.71 (m, 1H); 7.19 (m, 1H); 7.63 (bs, 2H); 7.93 (s, 1H); 8.61 (s, 1H).

5-Amino-8-butyl-2-(2-furyl)-pyrazolo[4,3-e] 1,2,4-triazolo[1,5-c]pyrimidine (Compound 37) yield 47%; white solid m.p. 200–203° C. (EtOAc-light petroleum); IR (KBr): 3500–2900, 1685, 1640, 1620, 1550, 1450 cm⁻¹; ¹H NMR (DMSO-d₆) δ 0.9 (t, 3H); 1.2 (m, 2H); 1.8 (m, 2H); 4.2 (t, 2H); 6.7 (m, 1H); 7.2 (m, 2H); 7.6 (s, 1H); 8.0 (s, 1H); 8.6 (s, 1H).

5-Amino-8-isopentyl-2-(2-furyl)-pyrazolo[4,3-e] 1,2,4-triazolo[1,5-c]pyrimidine (Compound 38) yield 60%; off-white solid m.p. 212–213° C. (EtOAc-light petroleum); IR (KBr): 3500–2850, 1670, 1650, 1615, 1560, 1455 cm⁻¹; ¹H NMR (CDCl₃) δ 0.96 (d, 6H, J=6.4); 1.59 (m, 1H); 1.86 (m, 2H); 4.32 (t, 2H, J=6.4); 6.58 (m, 1H); 6.72 (bs, 2H); 7.21 (d, 1H, J=4.2); 7.63 (d, 1H, J=1.2); 8.10 (s, 1H).

5-Amino-8-(2-isopentenyl)-2-(2-furyl)-pyrazolo[4,3-e] 1,2,4-triazolo[1,5-c]pyrimidine (Compound 39) yield 58%; pale yellow solid m.p. 178–179° C. (EtOAc-light petroleum); IR (KBr): 3520–2950, 1665, 1640, 1610, 1555, 1450 cm⁻¹; ¹H NMR (CDCl₃) δ 1.74 (s, 3H); 1.77 (s, 3H); 4.87 (d, 2H, J=7); 5.43–5.46 (m, 1H); 6.72 (m, 1H); 7.18 (m, 1H); 7.62 (bs, 2H); 7.93 (s, 1H); 8.55 (s, 1H).

5-Amino-8-(2-(phenyl)ethyl)-2-(2-furyl)-pyrazolo[4,3-e] 1,2,4-triazolo[1,5-c]pyrimidine (Compound 40) yield 45%; white solid m.p. 183–185° C. (EtOAc-light petroleum); IR (KBr): 3500–2900, 1670, 1645, 1620, 1530, 1455 cm⁻¹; ¹H NMR (DMSO-d₆) δ 3.21 (t, 2H, J=6.4); 4.53 (t, 2H, J=6.4); 6.7 (s, 1H); 7.1–7.4 (m, 6H), 7.65 (bs, 2H); 7.93 (s, 1H); 8.45 (s, 1H).

5-Amino-8-(3-(phenyl)propyl)-2-(2-furyl)-pyrazolo[4,3-e] 1,2,4-triazolo[1,5-c]pyrimidine (Compound 41) yield 57%; yellow solid m.p. 168–170° C. (EtOAc-light petroleum); IR (KBr): 3510–2950, 1665, 1640, 1615, 1520, 1455 cm⁻¹; ¹H NMR (DMSO-d₆) δ 2.14–2.21 (m, 2H); 2.54 (t, 2H, J=7); 4.29 (t, 2H, J=6.4); 6.71 (s, 1H); 7.14–7.32 (m, 6H), 7.64 (bs, 2H); 7.93 (s, 1H); 8.64 (s, 1H).

Example 3

Preparation of 5-[[(Substituted phenyl)amino]carbonyl]amino-8-(ar)alkyl-2-(2-furyl)-pyrazolo[4,3-e] 1,2,4-triazolo[1,5-c]pyrimidine (Compounds 42–57)

5-[[substituted phenyl)carbonyl]amino-8-(Ar)alkyl-2-(2-furyl)-pyrazolo[4,3-e]1,2,4-triazolo[1,5-c]pyrimidines can be prepared according to the synthetic strategy shown in the following Scheme VIII.

Scheme VIII
General procedures for the preparation of 5-[[(Substituted phenyl)amino]carbonyl]amino-8-(ar)alkyl-2-(2-furyl)-pyrazolo[4,3-e] 1,2,4-triazolo[1,5-c]pyrimidine (Compounds 42–57)

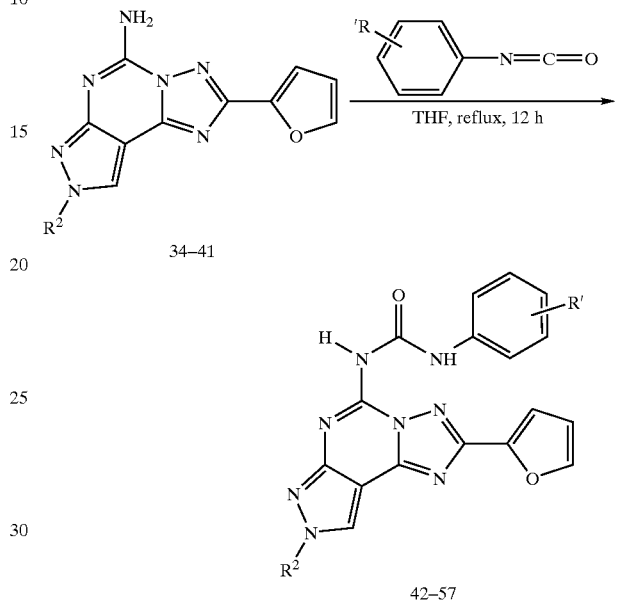

In the preparation of compounds 42–57, the appropriate amino compound (Compounds 34–41) (10 mmol) was dissolved in freshly distilled THF (15 ml) and the appropriate isocyanate (13 mmol) was added. The mixture was refluxed under argon for 18 hours. Then the solvent was removed under reduced pressure and the residue was purified by flash chromatography (EtOAc-light petroleum 4–6) to afford the desired compounds 42–57. Following this general procedure the following compounds have been prepared:

5-[[(3-Chlorophenyl)amino]carbonyl]amino-8-methyl-2-(2-furyl)-pyrazolo[4,3-e]1,2,4-triazolo[1,5-c]pyrimidine (Compound 42) yield 98%; pale yellow solid m.p. 142–145° C. (Et₂O-light petroleum); IR (KBr): 3210–2930, 1660, 1630, 1610, 1500 cm⁻¹; ¹H NMR (CDCl₃) δ 4.21 (s, 3H); 6.60 (m, 1H); 7.11 (d, 1H, J=8); 7.13–7.28 (m, 2H): 7.55 (d, 1H, J=8); 7.65 (s, 1H); 7.78 (d, 1H, J=2); 8.22 (s, 1H); 8.61 (bs, 1H); 11.24 (bs, 1H).

5-[[(4-Methoxyphenyl)aminocarbonyli]amino-8-methyl-2-(2-furyl)-pyrazolo[4,3-e] 1,2,4-triazolo[1,5-c]pyrimidine (Compound 43) yield 99%; yellow solid m.p. 193–195° C. (Et₂O-light petroleum); IR (KBr): 3200–2900, 1664, 1625, 1600, 1500 cm⁻¹, ¹H NMR (CDCl₃) δ 3.81 (s, 3H); 4.20 (s, 3H); 6.61 (m, 1H); 6.85 (d, 2H, J=9); 7.26 (m, 1H); 7.55 (d, 2H, J=9); 7.65 (s, 1H); 8.21 (s, 1H); 8.59 (bs, 1H); 10.96 (bs, 1H).

5-[[(3-Chlorophenyl)amino]carbonyl]amino-8-ethyl-2-(2-furyl)-pyrazolo[4,3-e] 1,2,4-triazolo[1,5-c]pyrimidine (Compound 44) yield 98%; pale yellow solid m.p. 204–205° C. (Et₂O-light petroleum); IR (KBr): 3220–2930, 1660, 1620, 1600, 1500 cm⁻¹; ¹H NMR (CDCl₃) δ 1.71 (t, 3H, J=7); 4.50 (q. 2H, J=7); 6.67 (m, 1H); 7.20 (d, 1H, J=8); 7.31 (m, 1H); 7.61 (d, 1H, J=8); 7.70 (s, 1H); 7.84 (s, 1H); 8.30 (s, 1H); 8.67 (bs, 1H); 11.30 (bs, 1H).

5-[[(4-Methoxyphenyl)amino]carbonyl]amino-8-ethyl-2-(2-furyl)-pyrazolo[4,3-e] 1,2,4-triazolo[1,5-c]pyrimidine (Compound 45) yield 99%; pale yellow solid m.p. 200–201° C. (Et$_2$O-light petroleum); IR (KBr): 3250–2950, 1665, 1620, 1610, 1520 cm$^{-1}$; $^1$H NMR (CDCl$_3$) δ 1.71 (t, 3H, J=7); 3.85 (s, 3H); 4.49 (s, 3H); 6.65 (m, 1H); 6.88 (d, 2H, J=9); 7.26 (m, 1H); 7.58 (d, 2H, J=9); 7.69 (s, 1H); 8.28 (s, 1H); 8.63 (bs, 1H); 10.99 (bs, 1H).

5-[[(3-Chlorophenyl)amino]carbonyl]amino-8-propyl-2-(2-furyl)-pyrazolo[4,3-e] 1,2,4-triazolo[1,5-c]pyrimidine (Compound 46) yield 95%; white solid m.p. 138–139° C. (Et$_2$O-light petroleum): IR (KBr): 3210-2920, 1655, 1615, 1600, 1510 cm$^{-1}$; $^1$H NMR (CDCl$_3$) δ 1.71 (t, 3H, J=7); 2.04 (m, 2H); 4.36 (q, 2H, J=7); 6.62 (m. 1H); 7.12 (d, 1H, J=8); 7.27 (m, 1H); 7.56 (d, 1H, J=8); 7.66 (s, 1H); 7,80 (s, 1H; 8.24 (s, 1H); 8.62 (bs, 1H); 11.08 (bs, 1H).

5-[[(4-Methoxyphenyl)amino]carbonyl]amino-8-propyl-2-(2-furyl)-pyrazolo[4,3-e] 1,2,4-triazolo[1,5-c]pyrimidine (Compound 47) yield 98%; pale yellow solid m.p. 146–148° C. (Et$_2$O-light petroleum); IR (KBr): 3230–2950, 1660, 1620, 1600, 1530 cm$^{-1}$ $^1$H NMR (CDCl$_3$) δ 0.98 (t, 3H, J=7); 2.04–2.08 (m, 2H); 3.82 (s, 3H); 4.35 (t, 2H, J=7); 6.61 (m, 1H); 6.89 (d, 2H, J=9); 7.25 (m, 1H); 7.56 (d, 2H, J=9); 7.65 (s, 1H); 8.23 (s, 1H); 8.59 (bs, 1H); 10.95 (bs, 1H).

5-[[(3-Chlorophenyl)amino]carbonyl]amino-8-butyl-2-(2-furyl)-pyrazolo[4,3-e] 1,2,4-triazolo[1,5-c]pyrimidine (Compound 48) yield 97%; white solid m.p. 210–212° C. (Et$_2$O-light petroleum); IR (KBr): 3240-2970, 1650, 1610, 1510 cm$^{-1}$; $^1$H NM R (CDCl$_3$) δ 1.00 (t, 3H, J=7); 1.39-1.41 (m, 2H); 1.99–2.03 (m, 2H); 4.41 (q, 2H, J=7); 6.63 (m, 1H); 7.14 (d, 1H, J=8); 7.29 (m, 1H); 7.56 (d, 1H, J=8); 7.67 (s, 1H), 7.80 (s, 1H); 8.25 (s, 1H); 8.63 (bs, 1H); 11.26 (bs, 1H).

5-[[(4-Methoxyphenyl)amino]carbonyl]amino-8-butyl-2-(2-furyl)-pyrazolo[4,3-e] 1,2,4-triazolo[1,5-c]pyrimidine (Compound 49) yield 96%; white solid m.p. 197–198° C. (Et$_2$O-light petroleum); IR (KBr): 3250–2960, 1665, 1610, 1600, 1520 cm$^{-1}$; $^1$H NMR (CDCl$_3$) δ 0.98 (t, 3H, J=7); 1.38-1-42 (m, 2H); 2.02–2.05 (m, 2H); 3.82 (s, 3H); 4.39 (t, 2H, J=7); 6.63 (m, 1H); 6.92 (d, 2H, J=9); 7.25 (m, 1H); 7.57 (d, 2H, J=9); 7.67 (s, 1H); 8.23 (s, 1H); 8.60 (bs, 1H); 10.95 (bs, 1H).

5-[[(3-Ch lorophenyl)amino]carbonyl]amino-8-isopentyl-2-(2-furyl)-pyrazolo[4,3-e] 1,2,4-triazolo[1,5-c]pyrimidine (Compound 50) yield 97%; pale yellow solid m.p. 199–200° C. (Et$_2$O-light petroleum); IR (KBr): 3230–2950, 1655, 1600, 1510 cm$^1$; 1H NMR (CDCl$_3$) δ 1.01 (d, 6H, J=7.5); 1.49–1.51 (m, 1H); 1.88–2.03 (m, 2H), 4.42 (t, 2H, J=7); 6.62 (m, 1H); 7.13 (d, 1H, J=8); 7.34 (m, 1H); 7.57 (d, 1H, J=8); 7.67 (s, 1H); 7.80 (s, 1H); 8.24 (s, 1H); 8.63 (bs, 1H); 11.25 (bs, 1H).

5-[[(4-Methoxyphenyl)amino]carbonyl]amino-8-isopentyl-2-(2-furyl)-pyrazolo[4,3-e] 1,2,4-triazolo[1,5-c]pyrimidine (Compound 51) yield 98%; white solid m.p. 192–193° C. (Et$_2$O-light petroleum); IR (KBr): 3230–2970, 1660, 1615, 1600, 1500 cm$^{-1}$; $^1$H NMR (CDCl$_3$) δ 0.99 (d, 6H, J=7.5); 1.58-1-22 (m, 1H); 1.87–1.97 (m, 2H); 3.82 (s, 3H); 4.40 (t, 2H, J=7); 6.62 (m, 1H); 6.91 (d, 2H, J=9); 7.23 (m, 1H); 7.58 (d, 2H, J=9); 7.66 (s, 1H); 8.23 (s, 1H); 8.59 (bs, 1H); 10.94 (bs, 1H).

5-[[(3-Chlorophenyl)amino]]carbonyl]amino-8-(2-isopentenyl)-2-(2-furyl)pyrazolo[4,3-e] 1,2,4-triazolo[1,5-c]pyrimidine (Compound 52) yield 99%; white solid m.p. 204–205° C. (Et$_2$O-light petroleum); IR (KBr): 3245–2960, 1650, 1600, 1510 cm$^{-1}$, $^1$H NMR (CDCl$_3$) δ 1.84 (s, 3H); 1.88 (s, 3H); 5.01 (d, 2H, J=8); 5.57 (m, 1H); 6.62 (m, 1H); 7.12 (d, 1H, J=8); 7.29 (m, 1H); 7.56 (d, 1H, J=8); 7.66 (s, 1H); 7.80 (s, 1H); 8.26 (s, 1H); 8.60 (bs, 1H); 11.26 (bs, 1H).

5-[[(4-Methoxyphenyl)amino]carbonyl]amino-8-(2-isopentenyl)-2-(2-furyl)-pyrazolo[4,3-e] 1,2,4-triazolo[1,5-c]pyrimidine (Compound 53) yield 96%; pale yellow solid m.p. 198–199° C. (Et$_2$O-light petroleum); IR (KBr): 3235–2950, 1665, 1620, 1600, 1510 cm$^1$, $^1$H NMR (CDCl$_3$) δ 1.83 (s, 3H); 1.87 (s, 3H); 3.81 (s, 3H); 4.97 (d, 2H, J=7); 5.57 (m, 1H); 6.61 (m, 1H); 6.93 (d, 2H, J=9); 7.24 (m, 1H); 7.54 (d, 2H, J=9); 7.66 (s, 1H); 8.25 (s, 1H); 8,58 (bs, 1H); 10.96 (bs, 1H).

5-[[(3-Chlorophenyl)amino]carbonyl]amino-B-(2-(phenyl)ethyl)-2-(2-furyl)-pyrazolo[4,3-e] 1,2,4-triazolo[1,5-c]pyrimidine (Compound 54) yield 98%; white solid m.p. 186–187° C. (Et$_2$O-light petroleum); IR (KBr): 3250–2970, 1660, 1610, 1515 cm$^{-1}$; $^1$H NMR (CDCl$_3$) δ 3.33 (t, 2H, J=7); 4.62 (t, 2H, J=7); 6.60 (m, 1H); 7.19–7.35 (m, 7H); 7.57 (d, 1H, J=8); 7.61 (s, 1H); 7.81 (s, 1H); 7.89 (s, 1H); 8.63 (bs, 1H); 11.27 (bs, 1H).

5-[[(4-Methoxyphenyl)amino]carbonyl]amino-8-(2-(phenyl)ethyl)-2-(2-furyl)-pyrazolo[4,3-e] 1,2,4-triazolo[1,5-c]pyrimidine (Compound 55) yield 99%; white solid m.p. 180–181° C. (Et$_2$O-light petroleum); IR (KBr); 3245–2960, 1660, 1615, 1600, 1500 cm$^{-1}$; $^1$H NMR (CDCl$_3$) δ 3.42 (t, 2H, J=7); 3.82 (s, 3H); 4.60 (t, 2H, J=7); 6.60 (m, 1H); 6.93 (d, 2H, J=9); 7.09 (m, 2H); 7.20–7.28 (m, 4H); 7.56 (d, 2H, J 8); 7.60 (s, 1H); 7.89 (s, 1H); 8.59 (bs, 1H); 10.96 (bs, 1H).

5-[[(3-Chlorophenyl)amino]carbonyl]amino-8-(3-(phenyl)propyl)-2-(2-furyl)-pyrazolo[4,3-e] 1,2,4-triazolo[1,5-c]pyrimidine (Compound 56) yield 99%; pale yellow solid m.p. 183–184° C. (Et$_2$O-Light petroleum); IR (KBr); 3245–2960, 1665, 1610, 1515 cm$^{-1}$, $^1$H NMR (CDCl$_3$) δ 2.46 (m, 2H); 2.73 (t, 2H, J=7); 4.43 (t, 2H, J=7); 6.66 (m, 1H); 7.19-7-40 (m,8H); 7.59 (d, 1H, J=8); 7.64 (s, 1H); 7.85 (m, 1H); 8.25 (s, 1H); 8.67 (bs, 1H); 11.30 (bs, 1H).

5-[[(4-Methoxyphenyl)amino]carbonyl]amino-8-(3-(phenyl)propyl)-2-(2-furyl)-pyrazolo[4,3-e] 1,2,4-triazolo[1,5-c]pyrimidine (Compound 57) yield 98%; white solid m.p. 174–175° C. (Et$_2$O-light petroleum); IR (KBr): 3240–2950, 1665, 1615, 1600, 1510 cm$^{-1}$; $^1$H NMR (CDCl$_3$) δ 2.46 (m, 2H); 2.73 (t, 2H, J=7); 4.42 (t, 2H, J=7); 6.67 (m, 1H); 6.96 (d, 2H, J=9); 7.22–7.41 (m, 6H); 7.60 (d, 2H, J=8); 7.64 (s, 1H); 8.25 (s, 1H), 8.65 (bs, 1H); 11.16 (bs, 1H).

Example 4

Preparation of 5-[(Benzyl)carbonyl]amino-8-(ar)alkyl-2-(2-furyl)-pyrazolo[4,3-e] 1,2,4-triazolo[1,5-c]pyrimidine (Compounds 58–59)

5-[[benzyl)carbonyl]amino-8-(Ar)alkyl-2-(2-furyl)-pyrazolo[4,3-e]1,2,4-triazolo[1,5-c]pyrimidines can be prepared according to the synthetic strategy shown in the following Scheme IX.

Scheme IX
General procedures for the preparation of 5-[(Benzyl)carbonyl]amino-8-(ar)alkyl-2-(2-furyl)-pyrazolo[4,3-e] 1,2,4-triazolo[1,5-c]pyrimidine (Compounds 58-59)

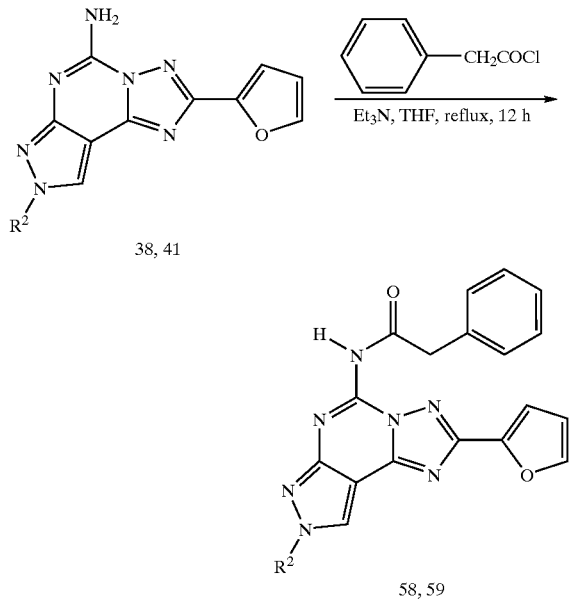

In the preparation of compounds 58–59, the appropriate amino compound (Compound 38 or 41) (10 mmol) was dissolved in freshly distilled THF (15 ml) and the appropriate acid halide (13 mmol) and triethylamine (13 mmol) were added. The mixture was refluxed under argon for 18 hours. The solvent was then removed under reduced pressure and the residue was dissolved in EtOAc (30 ml) and washed twice with water (15 ml). The organic phase was dried on $Na_2SO_4$ and concentrated under reduced pressure. The residue was purified by flash chromatography (EtOAc-light petroleum 4:6) to afford the desired compounds 58 and 59.

Following this general procedure the following compounds have been prepared:

5-[(Benzyl)carbonyl]amino-8-isopentyl-2-(2-furyl)-pyrazolo[4,3-e] 1,2,4-triazolo[1,5-c]pyrimidine (Compound 58) yield 85%, pale yellow solid m.p. 144–145° C. (Et$_2$O-light petroleum); IR (KBr): 3255–2930, 1673, 1620, 1610, 1520 cm$^{-1}$; $^1$H NMR (CDCl$_3$) δ 0.98 (d, 6H, J=7.5); 1.60 (m, 1H); 1.91 (m, 1H); 4.40 (t, 2H, J=7); 4.53 (s, 2H); 6.60 (m, 1H); 7.18 (m, 1H); 7.26–7.39 (m, 5H); 7.64 (s, 1H); 8.22 (s, 1H); 9.11 (bs, 1H).

5-[(Benzyl)carbonyl]amino-8-(3-(phenyl)propyl)-2-(2-furyl)-pyrazolo[4,3-e]1,2,4-triazolo[1,5-c]pyrimidine (Compound 59) yield 95%, pale yellow solid m.p. 116–117° C. (Et$_2$O-light petroleum); IR (KBr); 3250–2900, 1675, 1625, 1600, 1500 cm$^{-1}$; $^1$H NMR (CDCl$_3$) δ 2.39 (m, 2H); 2.67 (t, 2H, J=7); 4.37 (t, 2H, J=7); 4.53 (s, 2H); 6.61 (m, 1H); 7.16–7.43 (m, 11H); 7.65 (s, 1H); 7.64 (s, 1H); 8.19 (s, 1H); 9.12 (bs, 1H).

Example 5

Preparation of 1-Substituted-4-cyano-5-aminopyrazoles

According to the procedures described in *J. Org. Chem.* 1956, 21, 1240; *J. Am. Chem. Soc.* 1956, 78, 784 and the references herein cited, the following compounds are prepared, starting from commercially available ethoxymethylene malonodinitrile and N1-substituted hydrazines, which are also commercially available:

1-methyl-4-cyano-5-aminopyrazole
1-n-butyl-4-cyano-5-aminopyrazole
1-isopentyl-4-cyano-5-aminopyrazole
1-(2-cyclopentyl)ethyl-4-cyano-5-aminopyrazole
1-hydroxyethyl-4-cyano-5-aminopyrazole
1-phenyl-4-cyano-5-aminopyrazole
1-tert-butyl-4-cyano-5-aminopyrazole.
1-(phenyl)ethyl-4-cyano-5-aminopyrazole
1-(2-chlorophenyl)-4-cyano-5-aminopyrazole.

These compounds can be used as intermediates to prepare pyrazolo-triazolo-pyrimidine compounds as described herein.

Example 6

Preparation of 1-substituted-4-cyano-3-aminopyrazoles

Starting from 4-cyano-5-aminopyrazole, prepared according the procedure reported in *Chem. Pharm. Bull.* 1970, 18, 2353 or in *J. Heterocyclic Chem.* 1979, 16, 1113, 1-substituted 4-cyano-3-aminopyrazoles can be prepared by direct alkylation with the corresponding alkyl halide in dimethyl formamide at 80° C. for 1 to 2 hours in the presence of anhydrous potassium carbonate. From the reaction mixture, containing the two N1 and N2 alkylated position isomers in an about 1:2 ratio, the N2 isomer can be isolated by a single crystallization or column chromatography on silica gel eluting with ethyl acetate and petroleum ether mixtures. Using these procedures, the following compounds were prepared:

1-methyl-4-cyano-3-aminopyrazole
1-butyl-4-cyano-3-aminopyrazole
1-benzyl-4-cyano-3-aminopyrazole
1-isopentyl-4-cyano-3-aminopyrazole
1-(phenyl)ethyl-4-cyano-3-aminopyrazole These compounds can be used as intermediates to prepare pyrazolo-triazolo-pyrimidine compounds as described herein.

Example 7

Preparation of phenylethyl-4-cyano-3-aminopyrazoles a) A suspension of anhydrous potassium carbonate (30 mmols) in DMF (50 ml) is added with 3-amino-4-cyano pyrazole (20 mmols), heating to a temperature of 80° C. for 30 minutes. The suspension is added with phenethyl bromide (25 mmols) and is heated to 80° C. for 2 hours. After cooling to room temperature, the mixture is evaporated to dryness under vacuum and the resulting residue is taken up with distilled water (100 ml) and extracted with ethyl acetate (3×50 ml). The combined organic extracts are dried over anhydrous sodium sulfate and evaporated to dryness under vacuum. The resulting residue consists of a 1:3 mixture of 1-phenylethyl-4-cyano-5-aminopyrazole (20%) and of 1-phenylethyl-4-cyano-3-aminopyrazole (60%) which may be used as such in Example 9 or chromatographed on silica gel column eluting with an ethyl acetate/hexane mixture to give: 1-phenylethyl-4-cyano-5-aminopyrazole M.P. 172–173° C.; (20%); $^1$H-NMR (DMSO-d$_6$): 3.04 (t, 2H);

4.12 (t, 2H); 5.85 (bs, 2H); 7.21–7.30 (m, 5H); 7.41 (s, 1H); 1-β-phenylethyl-4-cyano-3-aminopyrazole M.P. 98–100° C. (60%); $^1$H NMR (CDCl$_3$): 3.07 (t, 2H); 4.10 (t, 2H); 4.23 (bs, 2H); 7.17 (s, 1H); 7.00–7.28 (m, 5H).

b) A solution of 1-β-phenylethyl-4-cyano-5-aminopyrazole (20 mmol) in triethylorthoformate (40 ml) was refluxed under nitrogen for 8 hours.

The excess orthoformate was evaporated to dryness under vacuum and the residual yellow oil is dissolved in ethyl ether and percolated onto silica gel to give the corresponding iminoether (87% yield). The residue obtained after orthoformate evaporation is practically pure and is directly used in the following step. A solution of the iminoether (20 mmol) and 2-furoic acid hydrazide (2.5 g, 22 mmol) in 2-methoxyethanol (50 ml) was refluxed for 5 to 10 hours. After cooling, the solution is evaporated to dryness to give an oily residue which is subjected to thermal cyclization in diphenylether (50 ml) using a Dean-Stark apparatus so as to azeotropically remove water formed during the reaction. After 1.5 hours, the reaction is checked by TLC (ethyl acetate:petroleum ether 2:1) and when the starting compound is completely absent, the mixture is cooled and added with hexane. The resulting precipitate is filtered and crystallized to give 7-(p-phenylethyl)-2-(2-furyl)-pyrazolo[4,3-e]1,2,4-triazolo[1,5-c]-pyrimidine M.P. 174–175° C. (20%) $^1$H NMR (DMSO-d 6):3.23 (t, 2H) 4.74 (t, 2H); 6.75 (s, 1H); 7.14–7.17 (m, 5H); 7.28 (s, 1H); 7.98 (s, 1H); 8.53 (s, 1 E); 9.56 (s, 1H).

In a similar way, starting from 1-β-phenylethyl-4-cyano-3-aminopyrazole, 8-(β-phenylethyl)-2-(2-furyl) pyrazolo[4,3-e]1,2,4-triazolo(1,5-c)-pyrimidine was prepared; M.P. 268–270° C. (600A) $^1$H NMR (DMSO-d$_6$): 3.32 (t, 2H); 4.72 (t, 2H); 6.73 (s, 1H), 7.23 (m, 5H); 7.95 (s, 1H); 8.8 (s, 1H); 9.41 (s, 1H).

c) A suspension of the product of step b) (10 mmol) in 10% HCl (5.0 ml) is refluxed under stirring for 3 hours. After cooling, the solution is made basic with concentrated ammonium hydroxide at 0° C. and the resulting precipitate is extracted with ethyl acetate (3×100 ml), dried and evaporated to dryness under vacuum, to give the corresponding 1-(β-phenylethyl)-4-[3(2-furyl)-1,2,4-triazol-5-yl]-5-amino pyrazole m.p. 175–176° C.; $^1$H NMR (DMSO-d 6):3.15 (t, 2H); 4.48 (t, 2H); 5.78 (s, 1H), 6.37 (s, 1H); 6.68 (s, 1H); 7.1 (s, 1H) 7.27–7.28 (m, 5H); 7.82 (s, 1H) 14.51 (bs, 2H): in a similar way 1-(β-phenylethyl)-4-[3(2-furyl)-1,2,4-triazol-5-yl)-3-aminopyrazole (m.p. 205–206° C.); $^1$H NMR (DMSO-d 6): 3.12 (t, 2H); 4.46 (t, 2H) 5.75 (s, 1H); 14.41 (bs, 2H) is obtained.

d) Cyanamide (60 mmol) is added to a suspension of the amine of step c) (10 mmole in N-methylpyrrolidone (40 ml) followed by p-toluene sulfonic acid (15 mmol). The mixture is heated to 160° C. under stirring. After 4 hours a second portion of cyanamide (60 mmol) is added and. heating is continued overnight. The mixture is then cooled and treated with hot water (200 ml) and the precipitate is filtered, washed with water and crystallized from ethanol to give the corresponding 5-amino-7-([-phenylethyl)-2-(2-furyl)-pyrazolo[4,3-e]-1,2,4-triazolo[1,5-c]pyrimidine m.p. 225–226° C. $^1$H NMR (DMSO-d 6): 3.21 (t, 2H); 4.51 (t, 2H); 6.65 (s, 1H); 7.1–7.44 (m, 6H); 7.78 (s, 1H); 7.89 (bs, 2H); 8.07 (s, 1H).

In a similar way 5-amino-8-(β-phenylethyl)-2-(2-furyl)-pyrazolo[4,3-e]-1,2,4-triazolo[1,5-c]-pyrimidine m.p. 212–213° C. $^1$H NMR (DMSO-d 6): 3.21 (t, 2H); 4.53 (t, 2H); 6.7 (s, 1H); 7.1–7.4 (m, 5H, arom and 1H); 7.65 (bs, 2H); 7.93 (s, 1H); 8.45 (s, 1H) was obtained.

Example 8

Preparation of 4-cyano-5-amino-1,2,3-triazoles

A suspension of potassium carbonate (0.23 mole) in DMSO (70 ml) is added subsequently with cyanoacetamide (70 mmols) and p-fluorobenzylazide (54.5 mmols). The resulting solution is stirred at room temperature for 1 h and then poured into a large volume of water (1.5 l). The separated solid is filtered, washed with water and dried in oven at 70° C. to give 1-(p-fluorobenzyl)-4-carboxamido-5-amino-1,2,3-triazole (96.1% yield).M.P.: 198–199° C.; $^1$H NMR (DMSO-d$_6$): 7.5–7.1 (m, 6H); 6.4 (s, 2H); 5.4 (s, 2H).

An amide suspension (0.005 mole), stirred and cooled to 0° C., in DMF (5 ml) is added with phosphorous oxychloride (0.01 mole). The resulting solution is stirred for 5 minutes at 0° C., 10 minutes at 25° C. and 15 minutes at 80° C. After cooling to room temperature, 5 ml of N HCl are added and the mixture is refluxed for 5 minutes. I-(p-fluorobenzyl)-4-cyano-5-amino-1,2,3-triazole separates from the cooled solution (90% yield). M.P. 185–186° C.; $^1$H NMR (DMSO-d 6): 7.3–7.0 (m, 6H); 5.5 (s, 2H); IR (KBr): 3400, 3220, 2220, 1655 cm-1.

Analogously, the following compounds were prepared:

1- or 2-benzyl-4-cyano-5-amino-1,2,3-triazole 1- or 2-(o-fluorobenzyl)-4-cyano-5-amino-1,2,3-triazole
   1- or 2-(p-fluorobenzyl)-4-cyano-5-amino-1,2,3-triazole 1- or 2-butyl-4-cyano-5-amino-1,2,3-triazole 1- or 2-isopentyl-4-cyano-5-amino-1,2,3-triazole 1- or 2-(2-methoxyethyl)-4-cyano-5-amino-1,2,3-triazole
   1-2-heptyl-4-cyano-5-amino-1,2,3-triazole 1- or 2-octyl-4-cyano-5-amino-1,2,3-triazole.

These compounds can be used as intermediates to prepare the triazolo-triazolo-pyrimidine compounds as described herein.

Example 9

Preparation of Ethoxymethyleneamino Heterocycles

The preparation of ethoxymethyleneamino heterocycles of formula IV is formed by refluxing the respective ortho-aminonitrile with ethyl orthoformate. By way of example, the preparation of 4-cyano-5-(ethoxymethyleneamino)-1-butylpyrazole is reported. A solution of 4-cyano-5-amino-1-butylpyrazole (20 mmols) in triethyl orthoformate (40 ml) is heated to the reflux temperature under nitrogen atmosphere for 8 hours. The orthoformate excess is evaporated to dryness under vacuum and the residual yellow oil is dissolved in ethyl ether and eluted through silica gel to give the pure compound (87% yield). In many cases, the residue obtained after evaporation of the orthoformate is substantially pure and is used as such in the subsequent step. IR (nujol): 3140, 2240, 1640 cm$^{-1}$; $^1$H NMR (CDCl$_3$): 8.4 (s, 1H); 7.9 (s, 1H); 4.5 (t, 2H); 4.3 (q, 2H); 1.8 (m, 2H); 1.5 (m, 2H); 1.4 (t, 3H); 0.9 (t, M).

Example 10

Cyclization of Ethoxymethyleneamino Heterocycles

A solution of the ethoxymethyleneamino heterocycle (20 mmols) and 2-furoic acid hydrazide (2.5 g, 22 mmols) in 2-methoxyethanol (50 ml) is refluxed for 5 to 10 hours. After cooling, the solution is evaporated to dryness to obtain a residual oil which is subjected to thermal cyclization in diphenyl ether (50 ml) using a round-bottom flask fitted with a Dean-Stark apparatus, to azeotropically remove the water formed during the reaction. After varying times (3 to 5 hours) the reaction is checked by TLC (2:1 ethyl acetate: petroleum ether) and when the whole starting product has disappeared, the mixture is cooled and hexane is added. The resulting precipitate is filtered and crystallized from the suitable solvent. In some cases, a viscous oil separates from the solution, which is then decanted and subsequently extracted. The oily residue is then chromatographed on silica gel, eluting with ethyl acetate/petroleum ether mixtures, to give the tricyclic compound VI.

By way of examples, the analytical and spectroscopical characteristics of some compounds prepared by these procedures are reported:

7-butyl-2-(2-furyl)-pyrazolo-[4,3-e]1,2,4-triazolo[1,5-c] pyrimidine. $^1$H NMR (DMSO-d 6): 9.6 (s, 1H); 8.6 (s, 1H); 8.0 (m, 1H); 7.4 (m, 1H); 6.7 (m, 1H); 4.5 (t, 2H); 1.9 (m, 2H); 1.3 (m, 2H); 0.9 (t, 3H).

8-butyl-2-(2-furyl)-pyrazolo[4,3-e]1,2,4-triazolo[1,5-c] pyrimidine. $^1$H NMR (DMSO-d 6): 9.4 (s, 1H); 8.9 (s, 1H); 8.0 (m, 1H), 7.3 (m, 1H); 6.2 (m, 1H); 4.5 (t, 2H); 1.9 (m, 2H); I.; (m, 2H); 0.9 (m, 3H). In the 2D-NMR (NOESY) spectrum, the N—CH$_2$ signal resonating at 4.5 shows cross peaks with the C9-H signal resonating at 8.9.

7-isopentyl-2-(2-furyl)-pyrazolo[4,3-e]1,2,4-triazolo[1,5-c]pyrimidine. $^1$H NMR (CDCl$_3$):9.1 (s, 1H); 8.8 (s, 1H); 7.7 (m, 1H); 7.3 (m, 1H); 6.6 (m, 1H); 4.6 (t, 2H); 1.18–1.7 (m, 3H); 1.0 (d, 6H).

8-isopentyl-2-(2-furyl)-pyrazolo[4,3-e]1,2,4-triazolo[1,5-c]pyrimidine. 9.1 (s, 1H); 8.8 (s, 1H); 7.7 (m, 1H); 7.3 (m, 1H); 6.6 (m, 1H); 4.6 (t, 2H); 1.9–1.5 (m, 3H); 1.0 (d, 6H).

Following this procedure, the following compounds were prepared:

7-methyl-2-(2-furyl)-pyrazolo[4,3-e]1,2,4-triazolo[1,5-c] pyrimidine 8-methyl-2-(2-furyl)-pyrazolo[4,3-e]1,2,4-triazolo[1,5-c] pyrimidine 7-(2-chlorophenyl)-2-(2-furyl)-pyrazolo[4,3-e]1,2,4-triazolo[1,5-c] pyrimidine 7-phenylethyl-2-(2-furyl)-pyrazolo[4,3-e]1,2,4-triazolo [1,5-c] pyrimidine 7-tert-butyl-2-(2-furyl)-pyrazolo[4,3-e]1,2,4-triazolo[1,5-c] pyrimidine 7-(2-(cyclopentyl)ethyl)-2-(2-furyl)-pyrazolo[4,3-e]1,2,4-triazolo[1,5-c] pyrimidine 8-benzyl-2-(2-furyl)-pyrazolo[4,3-e]1,2,4-triazolo[1,5-c] pyrimidine 7-benzyl-2-(2-furyl)-1,2,3-triazolo[5,4-e]1,2,4-triazolo[1,5-c] pyrimidine 7-(2-fluorobenzyl)-2-(2-furyl)-1,2,3-triazolo[5,4-e]1,2,4-triazolo[1,5-c] pyrimidine 7-(4-fluorobenzyl)-2-(2-furyl)-1,2,3-triazolo[5,4-e]1,2,4-triazolo[1,5-c] pyrimidine 7-butyl-2-(2-furyl)-1,2,3-triazolo[5,4-e]1,2,4-triazolo[1,5-c] pyrimidine 7-isopentyl-2-(2-furyl)-1,2,3-triazolo[5,4-e]1,2,4-triazolo [1,5-c] pyrimidine 7-(2-methoxy)ethyl-2-(2-furyl)-1,2,3-triazolo[5,4-e]1,2,4-triazolo[1,5-c] pyrimidine 7-heptyl-2-(2-furyl)-,2,3-triazolo[5,4-e]1,2,4-triazolo[1,5-c] pyrimidine 7-octyl-2-(2-furyl)-1,2,3-triazolo[5,4-e]1,2,4-triazolo[1,5-c] pyrimidine 8-benzyl-2-(2-furyl)-1,2,3-triazolo[5,4-e]1,2,4-triazolo[1,5-c] pyrimidine 8-(2-fluorobenzyl)-2-(2-furyl)-1,2,3-triazolo[5,4-e]1,2,4-triazolo[1,5-c] pyrimidine 8-(4-fluorobenzyl)-2-(2-furyl)-1,2,3-triazolo(5,4-e]1,2,4-triazolo[1,5-c] pyrimidine 8-butyl-2-(2-furyl)-1,2,3-triazolo[5,4-e]1,2,4-triazolo[1,5-c] pyrinidine 8-isopentyl-2-(2-furyl)-1,2,3-triazolo[5,4-e]1,2,4-triazolo [1,5-c] pyrimidine 8-hexyl-2-(2-furyl)-1,2,3-triazolo[5,4-e] 1,2,4-triazolo[1,5-c] pyrimidine 8-heptyl-2-(2-furyl)-1,2,3-triazolo[5,4-e]1,2,4-triazolo[1,5-c] pyrimidine 8-octyl-2-(2-furyl)-1,2,3-triazolo[5,4-e]1,2,4-triazolo[1,5-c] pyrimidine 9-benzyl-2-(2-furyl)-1,2,3-triazolo[4,5-e1,2,4-triazolo[1,5-c] pyrimidine 9-(2-fluorobenzyl)-2-(2-furyl)-1,2,3-triazolo[4,5-e]1,2,4-triazolo[1,5-c] pyrimidine 9-(4-fluorobenzyl)-2-(2-furyl)-1,2,3-triazolo[4,5-e]1,2,4-triazolo[1,5-c] pyrimidine These compounds can be used as intermediates to prepare the triazolo-triazolo-pyrimidines and pyrazolo-triazolo-pyrimidines as described herein.

Example 11

Preparation of 5-amino-7-[aralkyl)]-2-(2-furyl)-pyrazole[4,3-e]-1,2,4-triazolo[1,5-c]pyrimidines A suspension of the amines of formula VII (10 mmols) in N-methyl-pyrrolidone (40 ml) is added with cyanamide (60 mmols) followed by p-toluenesulfonic acid (15 mmols). The mixture is heated to 160° C. with magnetic stirring. After 4 hours, a second portion of cyanamide (60 mmols) is added and heating is continued overnight. The mixture is then cooled and treated with hot water (200 ml) and the precipitated solid is filtered, washed with water and crystallized from ethanol. If no precipitations take place, the solution is extracted with ethyl acetate (4×100 ml), the extracts are washed with brine (2×50 ml), dried and evaporated to dryness under vacuum. The residue is then chromatographed on a silica gel column eluting with ethyl acetate.

In the following, the analytical and spectroscopic data of some compounds prepared by this procedure are reported:

5-amino-7-butyl-2-(2-furyl)-pyrazolo[4,3-e]-1,2,4-triazolo[1,5-c]pyrimidine. M.P.157–158° C.; $^1$H NMR (DMSO-d 6) 8.1 (s, 1H); 8.0 (s, 2H); 7.9 (m, 1H); 7.2 (m, 1H); 6.7 (m, 1H); 4.2 (t, 2H); 1.9 (m, 2H); 1.5 (m, 2H); 0.9 (t, 3H). 5-amino-8-butyl-2-(2-furyl)-pyrazolo[4,3-e]-1,2,4-triazolo[1,5-c]pyrimidine m.p. 183–185° C.; $^1$H NMR (DMSO-d 6): 8.6 (s, 1H); 8.0 (s, 1H); 7.6 (s, 2H); 7.2 (m, 1H); 6.7 (m, 1H); 4.2 (t, 2H); 1.8 (m, 2H); 1.2 (m, 2H); 0.9 (t, 3H).

5-amino-7-benzyl-2-(2-furyl)-1,2,3-triazolo[5,4-e]1,2,4-triazolo[1,5-c]pyrimidine. M.p. 295–297° C.; $^1$H NMR (DMSO-d 6): 8.5 (s, 2H); 8.0 (s, 1H); 7.3 (m, 6H); 6.7 (m, 1H); 5.7 (s, 2H).

5-amino-7-o-fluoro-benzyl-2-(2-furyl)-1,2,3-triazolo[5,4-e]-1,2,4-triazolo[1,5-c]pyrimidine M.p. 310–312° C.; $^1$H NMR (DMSO-d 6): 8.5 (s, 2H); 8.0 (s, 1H); 7.3 (m, 5H); 6.8 (s, 1H); 5.75 (s, 2H).

5-amino-7-methyl-2-(2-furyl)-pyrazolo[4,3-e]-1,2,4 triazolo-[1,5-c] pyrimidine; m.p. 210–213° C.

5-amino-7-tert-butyl-2-(2-furyl)-pyrazolo[4,3-e]-1,2,4 triazolo-[1,5-c]pyrimidine; m.p. 238–240° C.

5-amino-2-(2-furyl)-pyrazolo[4,3-e]-1,2,4-triazolo-[1,5-c] pyrimidine; m.p. 248–250° C.

5-amino-7-(2-hydroxyethyl)-2-(2-furyl)-pyrazolo[4,3-e] 1,2,4-triazolo-[1,5-c]pyrimidine; m.p. 258–260° C.

5-amino-7-phenyl-2-(2-furyl)-pyrazolo(4,3-e]-1,2,4-triazolo-[1,5-c] pyrimidine; m.p. 295–297° C.

5-amino-7-isopentyl-2-(2-furyl)-pyrazolo[4,3-e]-1,2,4-triazolo-[1,5-e] pyrimidine; m.p. 208–210° C.

5-amino-8-isopentyl-2-(2-furyl)-pyrazolo(4,3-e)-1,2,4-triazolo-[1,5-c]pyrimidine;. m.p. 200–203° C.

5-amino-7-phenethyl-2-(2-furyl)-pyrazolo[4,3-e]-1,2,4-triazolo-[1,5-c]pyrimidine; m.p. 225° C.

5-amino-7-[2-(benzyloxy)ethyl]-2-(2-furyl)-pyrazolo[4,3-e]1,2,4-triazolo-[1,5-c]pyrimidine.

5-amino-7-[2-(4-isobutylphenyl)ethyl]-(2-furyl)-pyrazole [4,3-e]-1,2,4-triazolo[1,5-c]pyrimidine m.p. 207–210° C.

These compounds can be reacted with a suitable acid or sulfonic acid derivative to arrive at the compounds of Formula I disclosed herein.

Example 12

Preparation of Substituted-4-carboxamido-5-amino-1,2,3-triazoles p-Fluorobenzylazide (15.1 g, 0.1 mole) and cyanacetamide (10.8 g, 0.13 moles) are added in this order to a suspension of powdered potassium carbonate (57.5 g, 0.42 mole) in dimethylsulfoxide (150 ml). The mixture is stirred at room temperature, for 1 hour. The mixture is poured into 3 liters of water and the solid which separates is filtered and washed thoroughly with water to give 22.47 g (96%) of 1-p-fluorobenzyl-4-carboxamido-5-amino 1,2,3-triazole. M.P.: 198–199° C.; $^1$H NMR (DMSO-d 6): 7.5–7.1 (m, 6H); 6.4 (s, 2H); 5.4 (s, 2H).

Analogously, the following are obtained:

2-fluoro-6-chlorobenzyl-4-carboxamide-5 amino-1,2,3-triazole; m.p. 230–231° C.; $^1$H NMR (DMSO d 6): 5.40 (s, 2H); 6.52 (bs, 2H); 7.12–7.45 (m, 5H).

3-fluorobenzyl-4-carboxamido-5-amino 1,2,3-triazole;m.p. 211–211° C. $^1$H-NMR (DMSO-d 6): 5.46 (s, 2H); 6.47 (bs, 2H); 7.00–7.52 (m, 6H).

2-fluorobenzyl-4-carboxamide-5-amino-1,2,3-triazole; M.P. 195–197° C.

1-(2-(phenyl)ethyl)-4-carboxamido-5-amino-1,2,3-triazole; M. P. 181–183° C.; $^1$H NMR (DMSO-d$_6$): 3.04 (t, 2H); 4.35 (t, 2H); 6.30 (bs, 2H); 7.20–7.47 (m, 7H).

Example 13

Preparation of Substituted-4-cyano-5-amino-1,2,3-triazoles

A suspension of 1-p-fluorobenzyl-4-carboxamido-5-amino-1,2,3-triazole (23.4 g, 0.1 mole) in DMF (100 10 ml), magnetically stirred at 0° C., is added with 20.8 ml (0.2 mole) of POCl$_3$. The solution is stirred for 5 h at 0° C., 10 h at room temperature and finally 15 h at 80° C. After cooling, 1 N HCl (100 ml) is added thereto and the resulting solution is refluxed for 5 h; upon cooling the following is obtained: 1,5 p-fluorobenzyl-4-cyano-5-amino-1,2,3-triazole (18.54 g, 90%) precipitates. M.P. 185–186° C.; $^1$H NMR (DMSO-d$_6$): 7.3–7.0 (m, 6H); 5.5 (s, 2H); IR (KBr): 3400, 3220, 2220, 1655 cm-1.

Analogously, the following compounds are obtained:

2-fluoro-6-chlorobenzyl-4-cyano-5-amino-1,2,3-triazole; M.P.181–185° C. $^1$H NMR (DMSO-d 6): 5.40 (s, 2H); 7.26–7.50 (m, 5H).

3-fluorobenzyl-4-cyano-5-amino-1,2,3-triazole; M.P. 195–197° C.; $^1$H NMR (DMSO-d 6): 5.44 (s, 2H); 7.00–7.43 (m, 6H).

2-fluorobenzyl-4-cyano-5-amino-1,2,3-triazole; M.P.: 195–197° C.

1-(2-(phenyl)ethyl)-4-cyano-5-amino-1,2,3-triazole; M.P.149–150° C. $^1$H NMR (DMSO-d 6): 3.04 (t, 2H), 4.36 (t, 2H); 7.03 (bs, 2H); 7.23–7.28 (m, 5H).

Example 14

Preparation of Substituted-4[3(2-furyl)-1,2,4-triazol-5-yl]-5-amino-1,2,3-triazoles A suspension of 1-p-fluorobenzyl-4-cyano-5-amino-,2,3-triazole (20 mmols) and 2-furoic acid hydrazide (22 mmols) in diphenyl ether (30 ml) is stirred and heated to reflux (260° C.) with a Dean-Stark apparatus until the starting compound disappears (TLC, 1 to 2 hours). After cooling, the mixture is diluted with petroleum ether and the resulting precipitate is either filtered or separated by decantation and chromatographed on a silica gel column eluting with 2:1 ethyl acetate and petroleum ether to obtain:

1-(p-fluorobenzyl)-4-[3-(2-furyl)-1,2,4-triazol-5-yl]-5-amino-1, 2, 3-triazole; m.p. 266–268° C. $^1$H NMR (DMSO-d 6): 14.5 (s, 1H); 7.8 (s, 1H); 7.4–7.1 (m, 5H); 6.6 (s, 1H); 6.5 (s, 2H); 5.5 (s, 2H).

Analogously, 1-(2-(phenyl)ethyl)-4[3(2-furyl)-1,2,4-triazol-5-yl]-5-amino-1,2,3-triazole (50%); m.p. 200–202° C. $^1$H-NMR (DMSO-d$_6$): 3.07 (t, 2H); 4.16 (t, 2H); 5.50 (bs, 2H); 6.61 (s, 1H); 6.95 (s, 1H); 7.2–7.4 (m, 5H); 7.78 (s, 1H); 13.8 (bs, 1H) is obtained.

Example 15

Preparation of 5-amino-7-substituted-2-(2-furyl)-1,2,3-triazolo[5,4-e]1,2,4-triazolo[1,5-c]pyrimidines A suspension of 1-(p-fluorobenzyl)-4-[3-(2-furyl)1,2,4-triazol-5-yl-5-amino-1,2,3-triazole (0.325 g, 1 mmols) in N-methyl-pyrrolidone (4 ml) is added with cyanamide (6 mmols) followed by p-toluenesulfonic acid (1.5 mmols). The mixture is heated at 160° C. with magnetic stirring. After 4 hours, a second portion of cyanamide (6 mmols) is added and heating is continued overnight. The mixture is then treated with hot water (20 ml) and the precipitated solid is filtered, washed with water and crystallized from ethanol. If no precipitations take place, the solution is extracted with ethyl acetate (4×10 ml), the extracts are washed with brine (2×5 ml), dried and evaporated to dryness under vacuum. The residue is then chromatographed on a silica gel column eluting with ethyl acetate to give 105 mg (30% yield) of 5-amino-7-p-fluoro-benzyl-2-(2-furyl)-1,2,3-triazolo[5,4-e] 1,2,4-triazolo[1,5-c]pyrimidine M.P.: 266–268° C.; $^1$H NMR (DMSO-d 6): 8.5 (bs, 2H); 7.95 (s, 1H); 7.4–7.1 (m, 6H); 6.7 (s, 1H); 5.7 (s, 2H).

Analogously, were obtained:

5-amino-7-(o-fluorobenzyl)-2-(2-furyl)-1,2,3-triazolo[5,4-e]1,2,4-triazolo[1,5-c]pyrimidine; M.P. 310° C.

5-amino-7-benzyl-2-(2-furyl)-1,2,3-triazolo[5,4-e]1,2,4-triazolo[1,5-c]pyrimidine; M.P. 295–297° C.

5-amino-7-(2-fluoro-6-chlorobenzyl)-2-(2-furyl)-1,2,3 triazolo-[5,4-e]1,2,4-triazolo[1,5-c]pyrimidine; M.P.

218–220° C.; ¹H NMR (DMSO-d₆): 8.51 (bs, 2H); 7.98 (s, 1H); 7.55–7.28 (m, 4H); 6.77 (m. 1H); 5.73 (s, 2H).

5-amino-7-(m-f uorobenzyl)-2-(2-furyl)1,2,3-triazolo[5,4-e]1,2,4-triazolo[1,5-c]pyrimidine; m.p. 280–283° C.; ¹H NMR (DMSO-d₆): 8.45 (bs, 2H); 7.98 (s, 1H); 7.4–7.1 (m, 5H); 6.76 (s, 1H); 5.75 (s, 2H).

5-amino-7-(β-phenylethyl)-2-(2-furyl)-I.2,3-triazolo[5,4-e] 1,2,4-triazolo[1,5-c]pyrimidine; M.P. 269–271° C.; ¹H NMR (DMSO-d₆): 8.4 (bs, 2H); 7.98 (s, 1H); 7.3–7.15 (m, 6H); 6.8 (s, 1H); 4.71 (t, 2H); 3.31 (t, 2H).

Example 16

Additional Compounds

Using the chemistry described above, the following additional compounds were prepared:

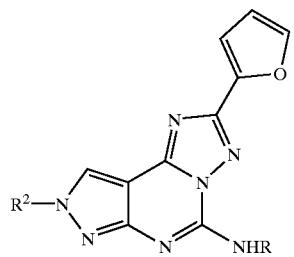

| Compd. | R² | R |
|---|---|---|
| 60 | H | H |
| 61 | H | 4-MeO-Ph-NHCO |
| 62 | H | 3-Cl-Ph-NHCO |
| 63 | t-C₄H₉ | H |
| 64 | t-C₄H₉ | 4-MeO-Ph-NHCO |
| 65 | t-C₄H₉ | 3-Cl-Ph-NHCO |
| 66 | CH₃ | Ph-NHCO |
| 67 | CH₃ | 4-SO₃H-Ph-NHCO |
| 68 | CH₃ | 3,4-Cl₂-Ph-NHCO |
| 69 | CH₃ | 3,4-(OCH₂—O)-Ph-NHCO |
| 70 | CH₃ | 4-(NO₂)-Ph-NHCO |
| 71 | CH₃ | 4-(CH₃)-Ph-NHCO |
| 72 | CH₃ | Ph-(CH₂)—CO |
| 73 | C₂H₅ | Ph-NHCO |
| 74 | C₂H₅ | 4-SO₃H-Ph-NHCO |
| 75 | C₂H₅ | 3,4-Cl₂-Ph-NHCO |
| 76 | C₂H₅ | 3,4-(OCH₂—O)-Ph-NHCO |
| 77 | C₂H₅ | 4-(NO₂)-Ph-NHCO |
| 78 | C₂H₅ | 4-(CH₃)-Ph-NHCO |
| 79 | C₂H₅ | Ph-(CH₂)—CO |
| 80 | n-C₃H₇ | Ph-NHCO |
| 81 | n-C₃H₇ | 4-SO₃H-Ph-NHCO |
| 82 | n-C₃H₇ | 3,4-Cl₂-Ph-NHCO |
| 83 | n-C₃H₇ | 3,4-(OCH₂—O)-Ph-NHCO |
| 84 | n-C₃H₇ | 4-(NO₂)-Ph-NHCO |
| 85 | n-C₃H₇ | 4-(CH₃)-Ph-NHCO |
| 86 | n-C₃H₇ | Ph-(CH₂)—CO |
| 87 | n-C₄H₉ | Ph-NHCO |
| 88 | n-C₄H₉ | 4-SO₃H-Ph-NHCO |
| 89 | n-C₄H₉ | 3,4-Cl₂-Ph-NHCO |
| 90 | n-C₄H₉ | 3,4-(OCH₂—O)-Ph-NHCO |
| 91 | n-C₄H₉ | 4-(NO₂)-Ph-NHCO |
| 92 | n-C₄H₉ | 4-(CH₃)-Ph-NHCO |
| 93 | 2-(α-napthyl)ethyl | Ph-(CH₂)—CO |
| 94 | 2-(α-napthyl)ethyl | H |
| 95 | 2-(α-napthyl)ethyl | 4-MeO-Ph-NHCO |
| 96 | 2-(α-napthyl)ethyl | 3-Cl-Ph-NHCO |
| 97 | 2-(2,4,5-tribromo-phenyl)ethyl | H |
| 98 | 2-(2,4,5-tribromo-phenyl)ethyl | 4-MeO-Ph-NHCO |
| 99 | 2-(2,4,5-tribromo-phenyl)ethyl | 3-Cl-Ph-NHCO |

-continued

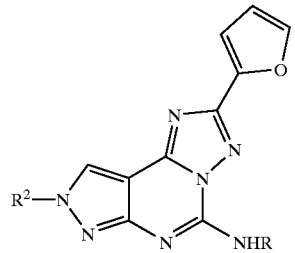

| Compd. | R² | R |
|---|---|---|
| 100 | 2-propen-1-yl | 4-MeO-Ph-NHCO |
| 108 | n-C₃H₇ | 4-MeO-Ph-NHCO |
| 109 | C₂H₅ | 4-MeO-Ph-NHCO |

Example 17

Preparation of Phenyl Isocyanates

Sulfonyl phenyl isocyanates can be prepared according to the synthetic strategy shown in the following Scheme X.

Scheme X
General procedures for the preparation of phenyl-isocyanates

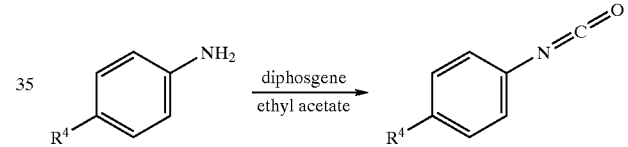

A suspension of the appropriate, commercially available amine is reacted with diphosgene using ethyl acetate as the solvent. The resulting isocyanate is then available for use as an intermediate in the synthesis of compounds of the present invention.

Following Scheme X the following phenyl-isocyanates may be produced, many of which are also commercially available:

4-(Diethylamino)phenyl isocyanate (used as intermediate in the production of Compounds 101–102).

4-(Dimethylamino)phenyl isocyanate (used as intermediate in the production of Compound 103).

4-(N-Morpholino)phenyl isocyanate (used as intermediate in the production of Compound 104).

Example 17

Preparation of Sulfonyl Phenyl Isocyanates

Phenyl isocyanates can be prepared according to the synthetic strategy shown in the following Scheme XI.

Scheme XI
General procedures for the preparation of sulfonyl-phenyl-isocyanates

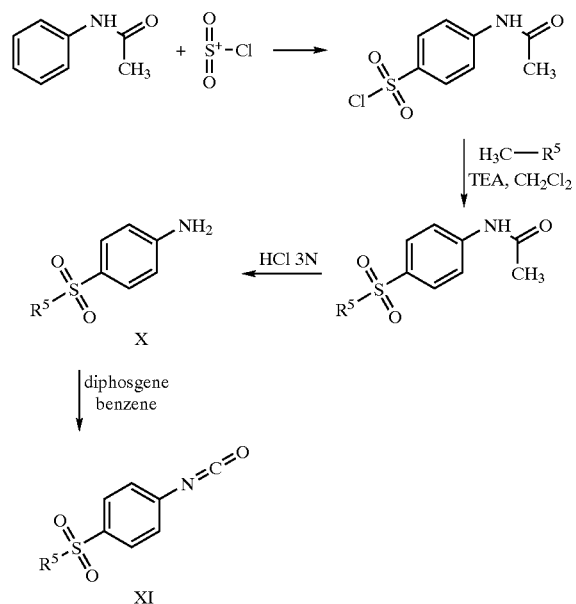

Acetanilide (20 g, 145 mmol) was added gradually to chlorosulfonic acid (48 mL, 725 mmol) at 0–5° C. After the addition is complete, the reaction mixture was heted to 60° C. for 2 h. After cooling to room temperature, the reaction mixture was poured slowly, with stirring onto 300 g of ice. The sulfonyl chloride that precipitated was collected by filtration, washed with water, then recrystallized from acetone at 35° C./–10° C.

A suspension of 4-acetylaminobenzene sulfonyl chloride (4.5 mmol) in anhydrous $CH_2Cl_2$ at room temperature is treated with 1-methyl piperazine (4.5 mmol) and triethylamine (4.5 mmol). The reaction mixture was stirred at room temperature for 1 hour, water was added, and the product extracted with additional $CH_2Cl_2$. The combined organic extracts were dried (Na2SO4), filtered, and evaporated under reduced pressure, affording the desired N-[4-(4-methylpiperazine-1-sulfonyl)phenyl]acetamide. Mp: 184° C.; Yield 41%; $^1$H NMR (DMSO $d_8$): δ 2.09 (s, 3H), 2.15 (s, 3H), 2.40 (m, 4H), 2.85 (m, 4H), 7.63–7.68 (d,2H, J=10 Hz), 7.80–7.84 (d, 2H, J=8 Hz), 10.41 (s, 1H).

N-[4-(4-methylpiperazine-1-sulfonyl)phenyl]acetamide (2 g, 6.7 mmol) was dissolved in 3 N HCl (50 mL) and 1,4-dioxane (12 mL). The reaction mixture was refluxed for 1 h, evaporated under vacuum, and the rsulting mixture made basic with 30% NH4OH. The desired product was extracted with $CH_2Cl_2$, dried (Na2SO4), filtered, and evaporated under reduced pressure to obtain 4-(4-methylpiperazin-1-sulfonyl)aniline as a white solid. MP: 210° C.; Yield 53%; $^1$H NMR (DMSO $d_6$): δ 2.22 (s, 3H), 2.50 (m, 4H), 2.82 (m, 4H), 6.10 (bs, 2H), 6.62–6.67 (d, 2H, J=10 Hz), 7.32–7.36 (d, 2H, J=8 Hz).

4-(4-Methylpiperazin-1-sulfonyl)aniline (0.5 g, 1.96 mmol) dissolved in anhydrous benzene was added dropwise to a solution of trichloromethylchloroformate (0.3 mL, 2.35 mmol) in anhydrous benzene at –10° C. The mixture was warmed to room temperature for 10 minutes, then heated to 90° C. for 2 h. The mixture was concentrated under reduced pressure to provide 4-[(4-methylpiperazin-1-yl)sulfonyl] phenyl isocyanate as a solid, used as an intermediate in the production of Compound 105. IR: 1166, 1339, 2265 cm$^1$.

Following Scheme XI the following sulfonyl-phenyl-isocyanates may be produced:

1-[(4-isocyanatophenyl)sulfonyl]-3-methylpiperazine
  N-[3-(dimethylamino)propyl]-4-isocyanatobenzenesulfonamide
  N-[3-(diethylamino)propyl]-4-isocyanatobenzenesulfonamide

Example 18

Preparation of 5-[[(Substituted phenyl)amino] carbonyl]amino-8-(ar)alkyl-2-(2-furyl)-pyrazolo[4,3-e] 1,2,4-triazolo[1,5-c]pyrimidine urea (Compounds 101, 104, 105, Int. 103)

5-[[substituted phenyl)carbonyl]amino-8-(Ar)alkyl-2-(2-furyl)-pyrazolo[4,3-e]1,2,4-triazolo[1,5-c]pyrimidines can be prepared according to the synthetic strategy shown in the following Scheme XII.

Scheme XII
General procedures for the preparation of 5-[[(Substituted phenyl) amino]carbonyl]amino-8-(ar)alkyl-2-(2-furyl)-pyrazolo[4,3-e] 1,2,4-triazolo[1,5-c]pyrimidine urea (Compounds 101, 104, 105, intermediate for Compound 103)

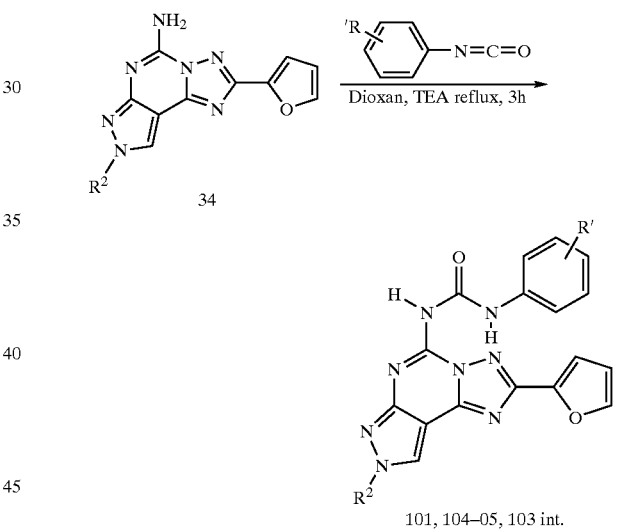

101, 104–05, 103 int.

In the preparation of compounds 101, 104, 105 and intermediate for compound 103, the appropriate amino compound (Compounds 34–41) (10 mmol) are dissolved in freshly distilled TEA and Dioxan, then the appropriate isocyanate (13 mmol) is added. The mixture is refluxed under argon for a minimum of 3 hours. Then the solvent is removed under reduced pressure and the residue is purified by flash chromatography (EtOAc-light petroleum 4–6) to afford the desired compounds 101, 104, 105 and intermediate for compound 103. In the case of compound 101 and the intermediate for compound 103, N-methyl pyrrolidone is also added with the isocyanate. Following this general procedure the following compounds have been prepared:

N-[4-(diethylamino)phenyl]-N'-[2-(2-furyl)-8-methyl-8H-pyrazolo[4,3-e][1,2,4]triazolo[1,5-c]pyrimidin-5-yl] urea (Compound 101)

N-(2-(2-furyl)-8-methyl-8H-pyrazolo[4,3-e][1,2,4] triazolo[1,5-c] pyrimidin-5-yl)-N'-[4-(morpholin-4-ylsulfonyl)phenyl]urea (Compound 104)

N-[2-(2-furyl)-8-methyl-8H-pyrazolo[4,3-e][1,2,4]triazolo[1,5-c] pyrimidin-5-yl]-N'-{4-[(4-methylpiperazin-1-yl)sulfonyl]-phenyl}urea (Compound 105)

N-[4-(dimethylamino)phenyl]-N'-[2-(2-furyl)-8-methyl-8H-pyrazolo[4,3-e][1,2,4]triazolo[1,5-c]pyrimidin-5-yl] urea (intermediate for Compound 103)

Example 19

Preparation of Pharmaceutical Salt of 5-[[(Substituted phenyl)amino]carbonyl]amino-8-(ar)alkyl-2-(2-furyl)-pyrazolo[4,3-e] 1,2,4-triazolo[1,5-c]pyrimidine urea (Compounds 102, 103)

Pharmaceutical salts of the present invention may be prepared in any method known in the art, including the method depicted in the following Scheme XIII.

Scheme XIII
General procedures for the preparation of hydrochloride salt of 5-[[(Substituted phenyl)amino]carbonyl]amino-8-(ar)alkyl-2-(2-furyl)-pyrazolo[4,3-e]1,2,4-triazolo[1,5-c]pyrimidine urea (Compounds 101, 104, 105, intermediate for Compound 103)

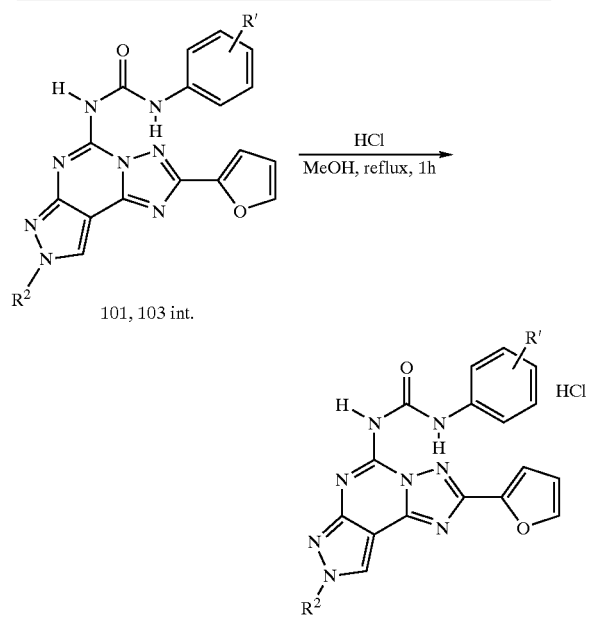

Starting with 100 mg of a pryrimidine urea compound of the present invention (for example, Compound 101, Int. 103), the hydrochloride salt is prepared by exposing the urea to 10 ml of methanol that has been saturated with HCl gas. Temperature is held at 0° C. while stirring is continued for approximately 1 hour. The solvent is then evaporated under vacuum to obtain a solid compound. The solid is purifed by resuspension in ethanol with subsequent solvent evaporation under vacuum. Following this general procedure the following compounds have been prepared:

N-[8-methyl-2-(2-furyl)-8H-pyrazolo[4,3-e][1,2,4]triazolo[1,5-c]pyrimidin-5-yl]-N'-[4-(diethylamino)phenyl] urea hydrochloride (Compound 102)

N-[8-methyl-2-(2-furyl)-8H-pyrazolo[4,3-e][1,2,4]triazolo[1,5-c]pyrimidin-5-yl]-N'-[4-(dimethylamino)phenyl]urea hydrochloride (Compound 103)

Example 20

Preparation of 5-[(pyridinyl)amino-8-(ar)alkyl-2-(2-furyl)-pyrazolo[4,3-e] 1,2,4-triazolo[1,5-c] pyrimidine urea (Compound 106)

5-[(pyridinyl)amino-8-(ar)alkyl-2-(2-furyl)-pyrazolo[4,3-e] 1,2,4-triazolo[1,5-c]pyrimidine ureas can be prepared according to the synthetic strategy shown in the following Scheme XIV.

Scheme XIV
General procedures for the preparation of 5-[(pyridinyl)amino-8-(ar)alkyl-2-(2-furyl)-pyrazolo[4,3-e] 1,2,4-triazolo[1,5-c] pyrimidine urea (Compound 106)

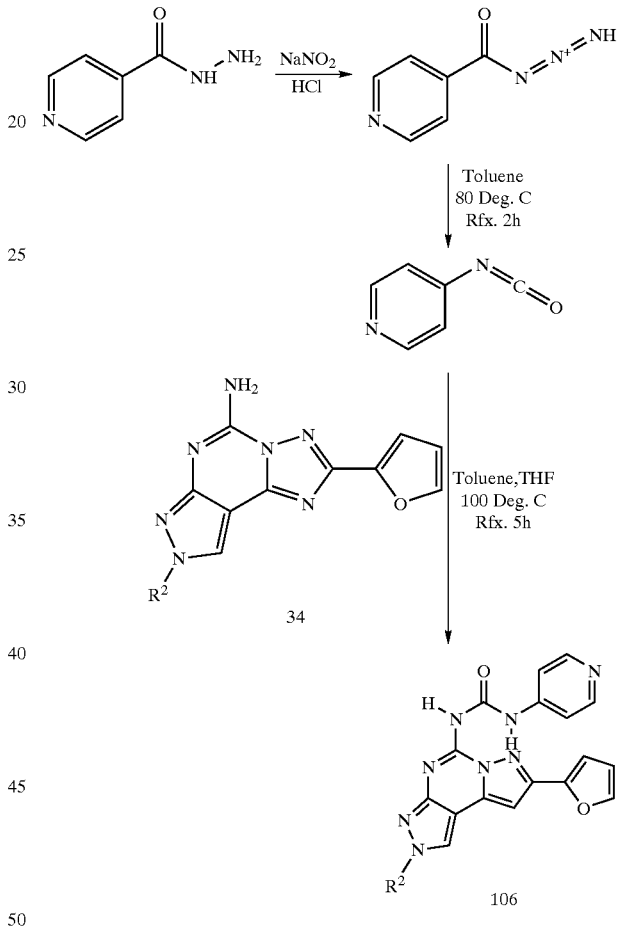

In the preparation of compounds such as 106 the appropriate amino compound (for example, Compounds 34–41) are added after the Curtius rearrangement of the acyl azide has occurred. To a solution of 13.8 sodium nitirite in 30 ml of aqueous HCl solution, 13.7 g of hydrazide is slowly added, keeping the temperature between 0° C. and 5° C. The mixture is stirred at 0° C. for an additional 0.5 hours. The reaction was extracted with EtOH, the organic layer washed with $NaCO_3$ solution having a pH=8.0 and then washed with water. The solution is then dried over $Na_2SO_4$ and concentrated a r.t. The white solid was filtered using petroleum ether to obtain the pyridineacylazide (M.P. 45° C.).

Next, 1.5 g of pyridineacylazide and 30 ml toluene are stirred at 80° C. for 2 hours, allowing the Curtius rearrangement to occur. Then 0.5 g of the tricyclic amine (Compound 34) are added and the mixture stirred at 100° C. for 5 hours (controlling on TLC between 95° C. and 105° C.). (CH$_2$Cl$_2$—CH$_3$OH). The solvent is evaporated and the product dissolved in scalding hot CH$_3$OH (heated to approx. 60° C.), adsorbed on silica gel and purified by chromatography to yield 0.9 g of a white solid. (M.P. 195–197° C.). Following this general procedure the following compound was prepared:

N-[2-(2-furyl)-8-methyl-8H-pyrazolo[4,3-e][1,2,4]triazolo[1,5-c]pyrimidin-5-yl]-N'-pyridin-4-yl urea (Compound 106). M.P. 195–197° C.

Starting with the urea Compound 106, a corresponding pharmaceutical salt was obtained as follows: 50 mg of Compound 106 is added to 5 ml of Dioxan and 5 ml of methanol that has been saturated with HCl gas and held at 0° C. while stirring is continued for approximately 1 hour. The solvent is then evaporated under vacuum to obtain a solid compound. The solid is then separated by filtration, and washed with EtOH. Following this procedure the following compound was prepared:

N-[2-(2-furyl)-8-methyl-8H-pyrazolo[4,3-e][1,2,4]triazolo[1,5-c]pyrimidin-5-yl]-N'-pyridin-4-ylurea hydrochloride (Compound 107). M.P. >300° C.; soluble in water.

Example 21

Evaluation of the Biological Activity of the Compounds

Several of the compounds described above have been tested for their affinity at rat $A_1$ and $A_{2A}$ and human $A_3$ receptors using the following assays.

Rat $A_1$ and $A_{2A}$ Adenosine Receptor Binding Assay

Male Wistar rats (200–250 g) were decapitated and the whole brain and striatum dissected on ice. The tissues were disrupted in a polytron homogenizer at a setting of 5 for 30 s in 25 volumes of 50 mM Tris HCl, pH 7.4, containing 10 mM MgCl$_2$. The homogenate was centrifuged at 48,000 for 10 min, and the pellet was resuspended in the same buffer containing 2 IU/mL adenosine deaminase. After 30 min incubation at 37° C., the membranes were centrifuged and pellets were stored at −80° C. Prior to freezing, an aliquot of homogenate was removed for protein assay with bovine albumin as reference standard. Binding assays were performed on rat brain and striatum membranes respectively, in the presence of 10 mM MgCl$_2$ at 25° C. All buffer solutions were adjusted to maintain a constant pH of 7.4.

Displacement experiments were performed in 500 μL of Tris HCl buffer containing 1 nM of the selective adenosine $A_1$ receptor ligand [$^3$H]CHA (N$^6$-cyclohexyladenosine) and membranes of rat brain (150–200 μg- of protein/assay).

Displacement experiments were performed in 500 μL of Tris HCl buffer containing 10 mM MgCl$_2$, 0.2 nM of the selective adenosine $A_{2A}$ receptor ligand [$^3$H]SCH58261 (5-amino-7-(2-(phenyl)ethyl)-2-(2-furyl)-pyrazolo[4,3-e]-1,2,4-triazolo[1,5-c]pyrimidine) and membranes of rat striatum (80–100 μg of protein/assay). To determine IC$_{50}$ values (where IC$_{50}$ is the inhibitor concentration displacing 50% of labeled ligand) the test compound was added in triplicate to binding assay samples at a minimum of six different concentrations. Separation of bound from free radio ligand was performed by rapid filtration through Whatman GF/B filters which were washed three times with ice-cold buffer. Filter bound radioactivity was measured by scintillation spectrometry after addition of 5 mL of Aquassure. Non specific binding was defined as binding in the presence of 10 μM R-PIA (N-(phenylisopropyl)adenosine) and 10 μM NECA (5'-(N-ethylcarboxamido) adenosine), respectively, and was always 10% of the total binding. Incubation time ranged from 150 min. at 0° C. to 75 min at 30° C. according to the results of previous time-course experiments. Ki values were calculated from the Cheng-Prusoff equation. All binding data were analyzed using the nonlinear regression curve-fitting computer program LIGAND.

Human Cloned $A_3$ Adenosine Receptor Binding Assays

An aliquot of membranes (8 mu of protein/mL) from HEK-293 cells transfected with the human recombinant $A_3$ adenosine receptor was used for binding assays. FIG. 1 shows a typical saturation of [$^{125}$I]AB-MECA (N$^6$-(4-amino-3-iodobenzyl)-5'-(N-methylcarbamoyl)adenosine) to HEK-293 cells. Inhibition experiments were carried out in duplicate in a final volume of 100 μL in test tub containing 0.3 nM [$^{125}$I]AB-MECA, 50 nM Tris HCL buffer, 10 mM MgCl$_2$, pH 7.4, 20 μL of diluted membranes (12.4 mg of protein/mL), and at least 6–8 different concentrations of typical adenosine receptor antagonists. Non-specific binding was defined in the presence of 50 μM R-PIA and was about 30% of total binding. Incubation time was 60 min at 37° C., according to the results of previous time-course experiments. Bound and free radioactivity was separated by filtering the assay mixture through Whatman GF/B glass-fiber filters using a Brandel cell harvester.

Results and Discussion

Compounds 34–59 were tested in radio ligand binding assays for affinity at rat brain $A_1$, $A_{2A}$ and human $A_3$ receptors, and the results are summarized in Table 1. Similarly, other compounds were tested in radio ligand binding assays for affinity at human $A_1$, $A_{2A}$, $A_{2B}$ and $A_3$ receptors, and the results are summarized in Table 2.

The data demonstrate that compounds lacking bulky (compounds 38, 40 and 41) groups at $N^5$ position show great affinity for $A_{2A}$ adenosine receptors with low selectivity vs. $A_1$ and low affinity at human adenosine $A_3$ receptor subtype, and that compounds with a substituted phenyl carbamoyl chain at the $N_5$ position possess affinity in nanomolar range at h$A_3$ receptor subtype with different degrees of selectivity vs. $A_1$ and $A_{2A}$ receptor subtype. In particular, the 4-methoxyphenylcarbamoyl moiety (Compounds 51, 55 and 57) confer higher affinity, of about three order of magnitude, than the 3-chlorophenylcarbamoyl moiety (Compounds 50, 54 and 56).

The introduction, at the $N^8$ position, of chains with different steric characteristics permits the design of derivatives with high potency at human $A_3$ adenosine receptor and better selectivity vs. $A_1$ and $A_{2A}$ receptor subtypes.

FIG. 1 shows a saturation curve of [$^{125}$I]AB-MECA to adenosine $A_3$ receptor and the linearity of the Scatchard plot in the inset is indicative, in our experimental conditions, of the presence of a single class of binding sites with KD value of 0.9±0.01 nM and Bmax value of 62±1 fmol/mg protein (n=3).

Figure 2:
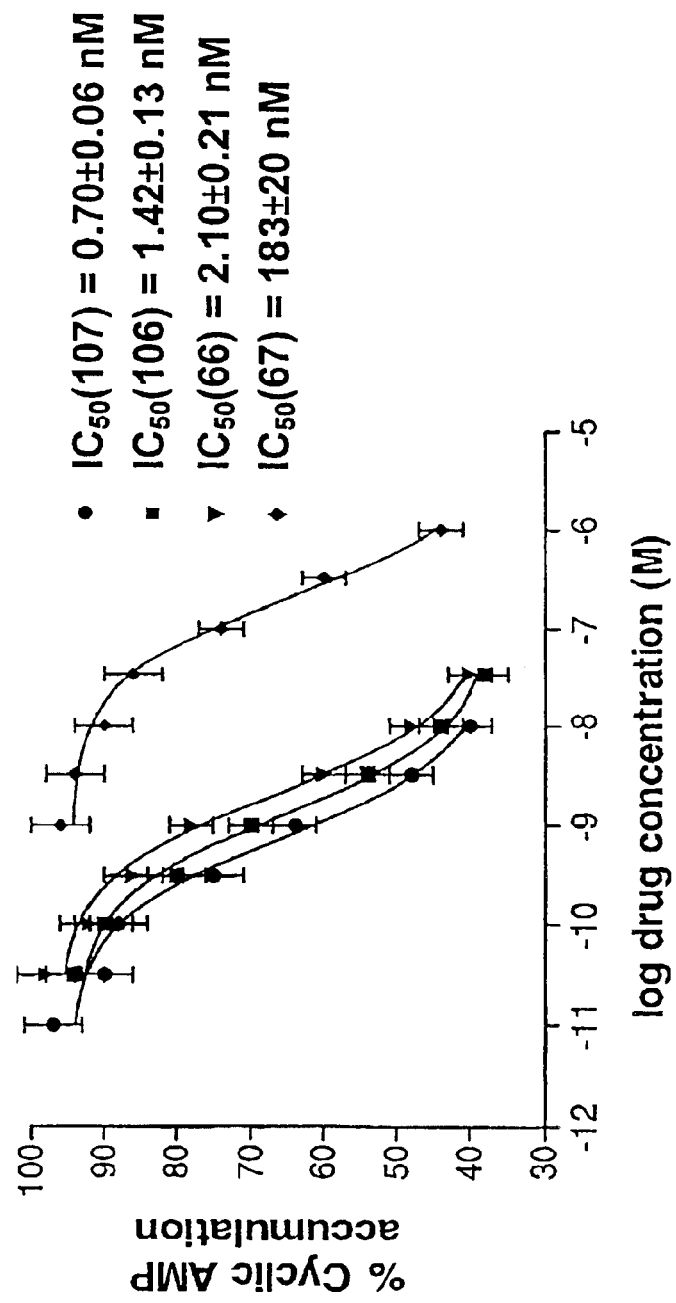
FIG. 2 is a graph showing the capability of compounds 66, 67, 106 and 107 to block C1-IB-MECA induced inhibition of cAMP production.

FIG. 2 shows the capability of compounds 66, 67, 106 and 107 to block C1-IB-MECA induced inhibition of cAMP production. It is seen that the potency of adenosine $A_3$ antagonism is comparable among Compounds 66, 106 and 107, while potency is 2 orders of magnitude less for Compound 67.

TABLE 1

Binding affinity at rA$_1$, rA$_{2A}$ and hA$_3$ adenosine receptors of compounds 34–59

| Compound | R$^2$ | R | rA$_1$ (K$_i$, nM) | rA$_{2A}$ (K$_i$, nM) | hA$_3$ (K$_i$, nM) | rA$_1$/hA$_3$ | rA$_{2A}$/hA$_3$ |
|---|---|---|---|---|---|---|---|
|  | MRS 1220* |  | 305 ± 51 | 52 ± 8.8 | 0.65 ± 0.25 | 470 | 80 |
| 34 | CH$_3$ | H | 313 (286–342) | 30.65 (28.62–32.82) | 557 (489–636) | 0.56 | 0.05 |
| 43 | CH$_3$ | 4-MeO—Ph—NHCO | <10,000 | >10,000 | 0.10 (0.09–0.11) | >100,000 | >100,000 |
| 42 | CH$_3$ | 3-Cl—Ph—NHCO | 5,045 (4,566–5,579) | >10,000 | 0.22 (0.20–0.25) | 22,931 | >45,454 |
| 35 | CH$_3$CH$_2$ | H | 95.09 (86.76–104.22) | 11.15 (9.84–12.63) | 3,579 (3,376–3,793) | 0.03 | 0.003 |
| 45 | CH$_3$CH$_2$ | 4-MeO—Ph—NHCO | >10,000 | >10,000 | 0.28 (0.25–0.32) | >35,714 | >35,714 |
| 44 | CH$_3$CH$_2$ | 3-Cl—Ph—NHCO | 2,699 (2,521–2,889) | 2,799 (2,621–2,989) | 2.09 (1.9–2.31) | 1,291 | 1,339 |
| 36 | CH$_3$CH$_2$CH$_2$ | H | 139 (107–181) | 20.23 (16.14–25.36) | 613 (582–646) | 0.22 | 0.03 |
| 47 | CH$_3$CH$_2$—CH$_2$ | 4-MeO—Ph—NHCO | >10,000 | 1,993 (1,658–2,397) | 0.29 (0.27–0.32) | >34,482 | 6,872 |
| 46 | CH$_3$CH$_2$—CH$_2$ | 3-Cl—Ph—NHCO | 1,582 (1,447–1,730) | <10,000 | 0.49 (0.47–0.52) | 3,228 | >20,408 |
| 37 | CH$_3$CH$_2$CH$_2$—CH$_2$ | H | 26.30 (23.66–29.24) | 4.20 (3.84–4.58) | 1,109 (981–1,254) | 0.02 | 0.003 |
| 49 | CH$_3$CH$_2$CH$_2$—CH$_2$ | 4-MeO—Ph—NHCO | 2,098 (1,923–2,290) | 649 (563–747) | 0.30 (0.26–0.34) | 6,993 | 2,163 |
| 48 | CH$_3$CH$_2$CH$_2$—CH$_2$ | 3-Cl—Ph—NHCO | 1,515 (1,382–1,661) | 498 (414–599) | 0.75 (0.65–0.86) | 2,020 | 664 |
| 38 | (CH$_3$)$_2$CH—CH$_2$—CH$_2$— | H | 8.09 (7.46–8.78) | 1.20 (1.03–1.40) | 1,163 (1,024–1,320) | 0.007 | 0.001 |
| 51 | (CH$_3$)$_2$CH—CH$_2$—CH$_2$— | 4-MeO—Ph—NHCO | 476 (432–525) | 376 (332–426) | 29.57 (26.94–32.46) | 16 | 13 |
| 50 | (CH$_3$)$_2$CH—CH$_2$—CH$_2$— | 3-Cl—Ph—NHCO | 1,650 (1,560–1,744) | 1,197 (1,027–1,396) | 81.10 (68.45–96.09) | 20 | 15 |
| 58 | (CH$_3$)$_2$CH—CH$_2$—CH$_2$— | Ph—CH$_2$CO | 373 (330–422) | 323 (280–372) | 81.10 (68.45–96.09) | 4.6 | 4 |
| 39 | (CH$_3$)$_2$C=CH—CH$_2$— | H | 10.08 (8.63–11.76) | 1.45 (1.36–1.54) | 887 (761–1034) | 0.01 | 0.001 |
| 53 | (CH$_3$)$_2$C=CH—CH$_2$— | 4-MeO—Ph—NHCO | 5,296 (4,826–5,811) | >10,000 | 29.57 (26.94–32.46) | 179 | >338 |
| 52 | (CH$_3$)$_2$C=CH—CH$_2$— | 3-Cl—Ph—NHCO | 3,744 (3,312–4,233) | 1,453 (1,363–1,549) | 147 (122–178) | 25.4 | 9.8 |
| 40 | Ph—CH$_2$—CH$_2$ | H | 2.16 (1.9–2.47) | 0.70 (0.53–0.91) | 2,785 (2,463–3,149) | 0.0007 | 0.0002 |
| 55 | Ph—CH$_2$—CH$_2$ | 4-MeO—Ph—NHCO | 1,282 (1,148–1,432) | 1,398 (1,225–1,594) | 1.47 (1.22–1.78) | 872 | 951 |
| 54 | Ph—CH$_2$—CH$_2$ | 3-Cl—Ph—NHCO | 1,049 (961–1,145) | 1,698 (1,524–1,892) | 13.28 (10.87–16.23) | 79 | 128 |
| 41 | Ph—CH$_2$—CH$_2$—CH$_2$ | H | 11.13 (9.34–13.27) | 0.59 (0.44–0.81) | 2,666 (2,533–2,805) | 0.004 | 0.0002 |
| 57 | Ph—CH$_2$—CH$_2$—CH$_2$ | 4-MeO—Ph—NHCO | 1,514 (1,332–1,721) | >10,000 | 19.81 (17.61–22.27) | 76.4 | >504 |
| 56 | Ph—CH$_2$—CH$_2$—CH$_2$ | 3-Cl—Ph—NHCO | >10,000 | 3,200 (3,025–3,385) | 42.65 (39.92–45.57) | >234 | 75 |
| 59 | Ph—CH$_2$—CH$_2$—CH$_2$ | Ph—CH$_2$CO | 345 (313–379) | 400 (365–438) | 121 (102–143) | 2.8 | 3.3 |

* values taken from Kim et al., J. Med. Chem., 39:4142–4148 (1996).

TABLE 2

Binding affinity at hA$_1$, hA$_{2A}$, hA$_{2B}$ and hA$_3$ adenosine receptors of compounds 101–109

| Cpd. | R$^2$ | R | hA$_1$ (K$_i$, nM) | hA$_{2A}$ (K$_i$, nM) | hA$_{2B}$ (K$_i$, nM) | hA$_3$ (K$_i$, nM) | hA$_1$/hA$_3$ | hA$_{2A}$/hA$_3$ | hA$_{2B}$/hA$_3$ |
|---|---|---|---|---|---|---|---|---|---|
| 101 | CH$_3$ | 4-N(C$_2$H$_5$)$_2$—Ph—NHCO | 580 (479–571) | 523 (479–571) | 350 (298–409) | 27 (21–34) | 21.5 | 19.4 | 13.0 |
| 102 | CH$_3$ | HCl × 4-N(C$_2$H$_5$)$_2$—Ph—NHCO | 680 (552–839) | 593 (539–652) | 276 (233–327) | 19 (14–26) | 35.8 | 31.2 | 14.5 |
| 103 | CH$_3$ | HCl × 4-N(CH$_3$)$_2$—Ph—NHCO | >10,000 | >10,000 | 609 (547–678) | 15 (9–24) | 667 | 667 | 40.6 |
| 104 | CH$_3$ | Mor-4-Ph—NHCO | 726 (681–774) | 1398 (1225–1594) | >10,000 | 2.47 (1.70–3.58) | 294 | 566 | 4050 |

TABLE 2-continued

Binding affinity at $hA_1$, $hA_{2A}$, $hA_{2B}$ and $hA_3$ adenosine receptors of compounds 101–109

| Cpd. | $R^2$ | R | $hA_1$ ($K_i$, nM) | $hA_{2A}$ ($K_i$, nM) | $hA_{2B}$ ($K_i$, nM) | $hA_3$ ($K_i$, nM) | $hA_1/hA_3$ | $hA_{2A}/hA_3$ | $hA_{2B}/hA_3$ |
|---|---|---|---|---|---|---|---|---|---|
| 105 | $CH_3$ | 4-CH3—Pip-$SO_2$—Ph—NHCO | >1,000 | >1,000 | >1,000 | 29 (22–40) | 34.5 | 34.5 | 34.5 |
| 106 | $CH_3$ | Pyr—NHCO | 250 (226–276) | 60 (43–84) | 200 (175–228) | 0.04 (0.02–0.06) | 6250 | 1500 | 5000 |
| 107 | $CH_3$ | HCl × Pyr—NHCO | 350 (334–367) | 100 (87–115) | 250 (241–259) | 0.01 (0.01–0.03) | 35000 | 10000 | 25000 |
| 108 | $nC_3H_7$ | 4-MeO—Ph—NHCO | 1197 | 141 | | 0.29 | 4150 | 486 | |
| 109 | $C_2H_5$ | 4-MeO—Ph—NHCO | 1026 | 1045 | | 0.28 | 3660 | 3730 | |

The data demonstrates that small chain ($C_{1-3}$) substituents at the 8-position of the 5-[[substituted phenyl)amino]carbonyl]amino-8-(ar) alkyl-2-(2-furyl)-pyrazolo[4,3-e] 1,2,4-triazolo[1,5-c]pyrimidine compounds described herein, in particular, methyl, ethyl and propyl groups, are preferred over larger chains such as pentyl and hexyl groups. In particular, Compounds 45 and 47, the 8-methyl, 8-ethyl and 8-propyl, 5-(4-methoxyphenyl) substituted compounds showed the high affinity and selectivity.

The methyl, ethyl and propyl chains can be substituted with phenyl or substituted phenyl groups and still show rather high affinity and selectivity for the $A_3$ receptor subtype, but the affinity is reduced by a factor of between 10 and 100. However, the compound with a β-phenylethyl chain at $N^8$ and 4-MeO-phenylcarbamoyl chain at the $N^5$ position (compound 55) showed a relatively good value in terms of affinity and selectivity ($K_ihA_3$=1.47 nM, $rA_1/hA_3$= 872, $rA_{2A}/hA_3$=951).

Even with the relatively large pentyl groups present in compounds 50 and 51, the compounds show a relatively high affinity for the $A_3$ receptor subtype (81.10 and 29.57 nm, respectively), although the selectivity falls by a factor of about 10 to 100.

Previous studies demonstrated that the affinity of 5-amino-8-(ar) alkyl-2-(2-furyl)-pyrazolo[4,3-e] 1,2,4-triazolo[1,5-c]pyrimidine compounds for the adenosine $A_2$ receptor subtype tended to increase with the size of the group at the 8 position. It appears that the opposite trend is true for affinity of the compounds described herein for the $A_3$ receptor subtype. $C_{1-3}$ substituents appear to represent the ideal steric and lipophilic characteristics for interaction with the $A_3$ receptor subtype.

Example 22

Binding Experiments with a Radiolabeled Compound

A series of binding experiments were performed on various tumor cell lines, using 0.5 nM [$^{125}$I]-ABMECA, with unspecific binding determined in the presence of 50 μM R-PIA or 200 μM NECA, on cell membranes of the cell lines. Specific binding was determined by substracting unspecific binding from total binding. The cell lines were the HL 60, NB4, SKN-MC, SKN-Be2C, SKN-SH and JURKAT cell lines. The results of the binding experiments are shown below in Table 3.

TABLE 3

| Cell Lines | Total Binding | Unspecific Binding | Specific Binding (cpm) | Percent Specific Binding |
|---|---|---|---|---|
| HL60 | 3484 | 2791 | 693 | 20 |
| NB4 | 3377 | 2740 | 637 | 19 |
| SKN-MC | 7528 | 6220 | 1308 | 17 |
| SKN-Be2C | 6000 | 4585 | 1415 | 24 |
| SKN-SH | 2671 | 2580 | 91 | 3 |
| JURKAT | 7599 | 4753 | 2846 | 38 |

Figure 3:
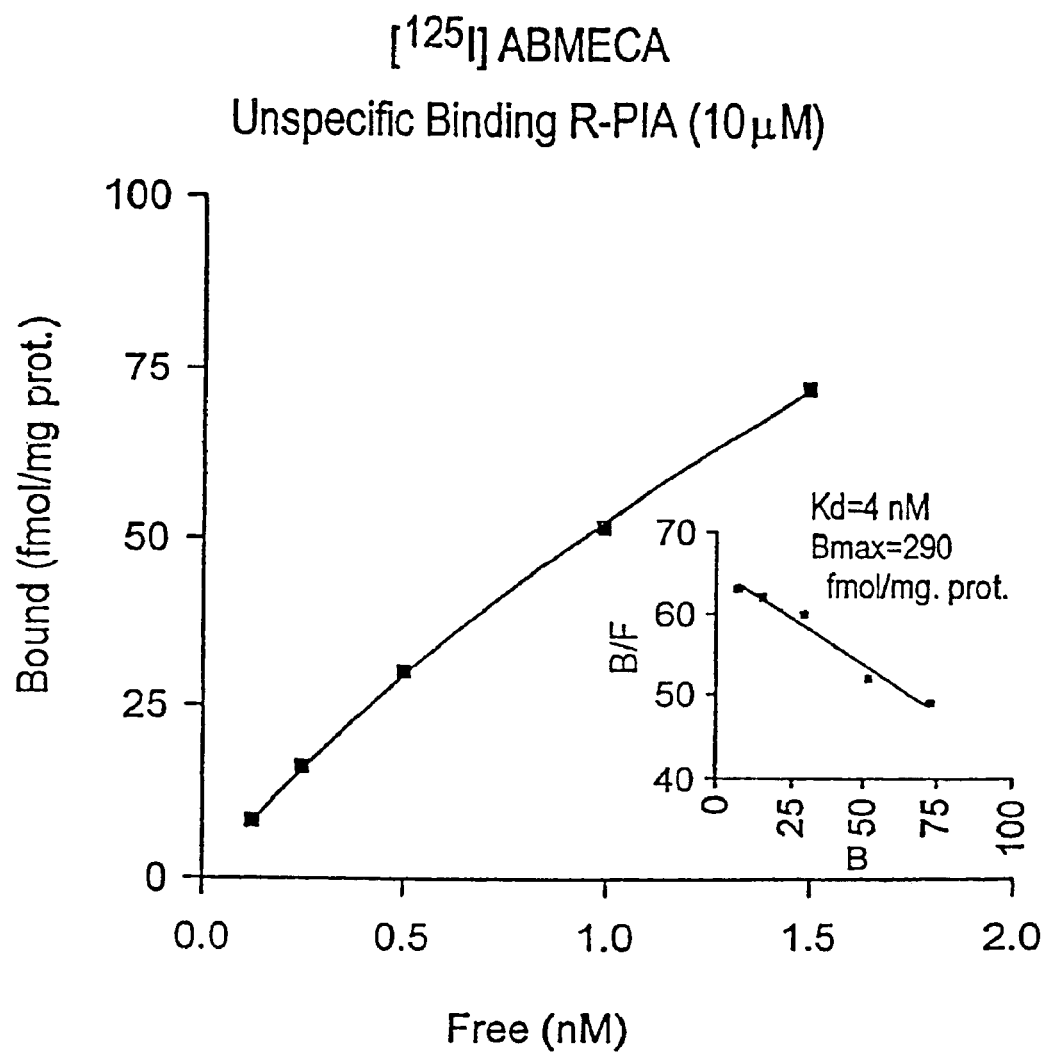
FIG. 3 is a graph showing the saturation of $[^{125}I]$AB-MECA binding (fmol/mg protein) to human $A_3$ receptors expressed in the JURKAT cell line versus the molar concentration of $[^{125}I]$AB-MECA. As shown in the Figure, the density of $A_3$ receptor detected was approximately 300 fmol/mg protein in Jurkat cell membranes using $[^{125}I]$AB-MECA.
Figure 4:
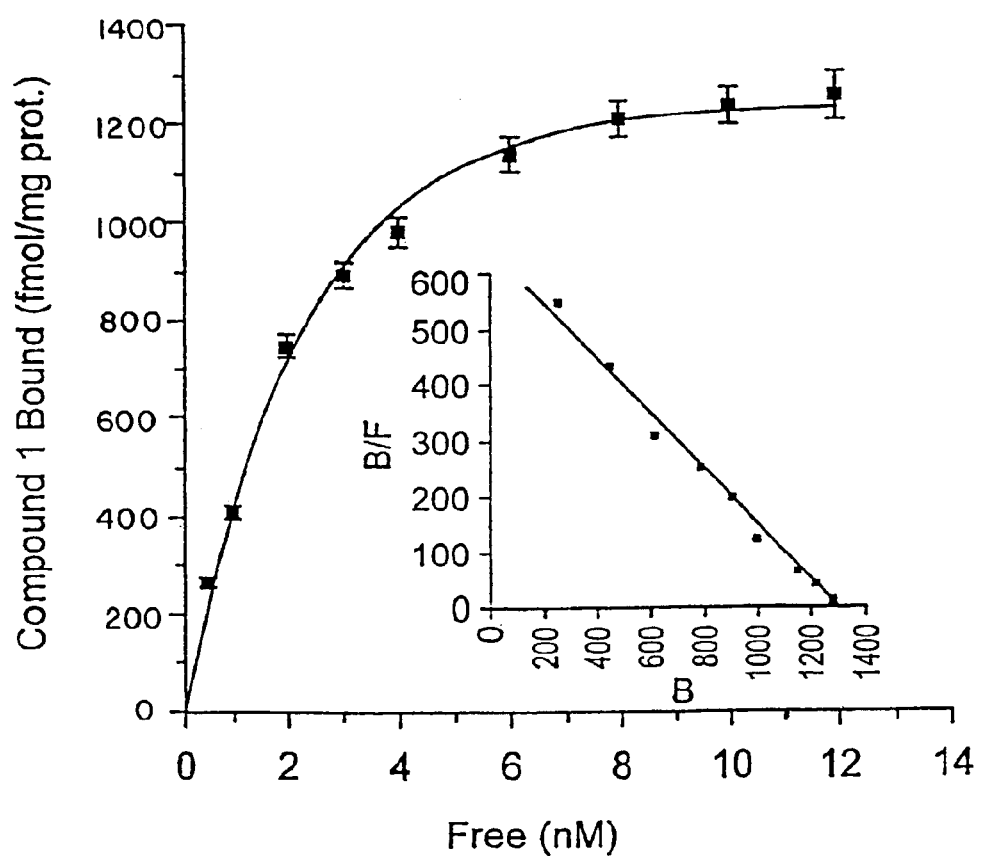
FIG. 4 and FIG. 5 are graphs showing the saturation of the binding of a tritiated analogue of compound 47-5-[[(4-methoxyphenyl)amino]carbonyl]amino-8-propyl-2-(2-furyl)-pyrazolo[4,3-e] 1,2,4-triazolo[1,5-c]pyrimidine (Compound 108) (fmol/mg protein) to $A_3$ receptors expressed in the JURKAT cell line versus the molar concentration of compound 108. The data in these figures show the presence of adenosine $A_3$ receptors in human tumor cells in high densities. For example, approximately 1300 fmol/mg protein was detected in Jurkat cells and 650 fmol/mg protein was detected in HL60 cells. Therefore, compound 108 is a far more sensitive tool for detecting adenosine $A_3$ receptors than $[^{125}I]$AB-MECA. These findings have facilitated the determination of the presence of $A_3$ receptors in many human tumors.

The results are shown in graphical form in FIG. 3. Jurkat cell lines appeared to provide the best results of the cell lines tested. A saturation experiment was performed using Jurkat cell lines at 37° C., with a one hour incubation period, using [$^{125}$I]-ABMECA (0.125–1.5 nM), with nonspecific binding measured using RPIA (50 μM). The Kd (nM) was 4, and the Bmax (fmol/mg protein) was 290. The results are also shown in FIG. 4.

Another assay was performed to determine whether Al receptor were present. A displacement assay was performed at 0° C. for 150 minutes on Jurkat cells using [$^3$H] DPCPX, a specific $A_1$ antagonist (0.5 nM), with nonspecific binding determined using R-PIA (50 μM). The total binding was 13208, the nonspecific binding was 2997, and the specific binding was 10211 (77%). Accordingly, a significant amount of $A_1$ binding was observed.

Figure 5:
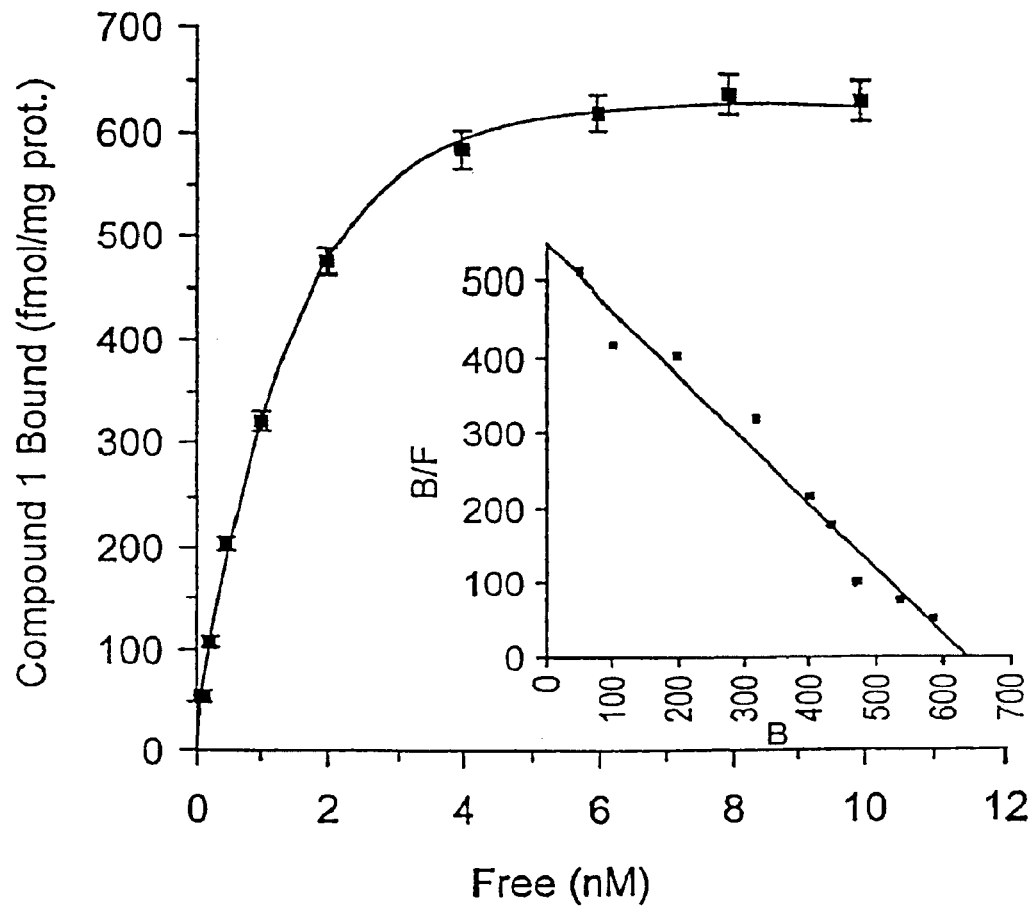

The following experiments described for the first time, the characterization of $A_3$ receptors in some human tumor cell lines such as HL60, a promyelocytic human leukaemia and Jurkat, a human T-cell leukaemia, by using the new selective antagonist (radioligand of Compound 108) described herein. In these studies, membranes (0.5 mg protein/ml) from Jurkat and HL60 cells were incubated with 10–12 different concentrations of compound 102 ranging from 0.2 to 15 nM and 0.1 to 10 nM for Jurkat and HL60 cells, respectively. FIG. 3 shows a saturation curve of compound 102 binding to adenosine $A_3$ receptors in Jurkat cell membranes and the linearity of the Scatchard plot in the inset is indicative of the presence fo a single class of binding sites with a Kd value of 1.9±0.2 nM and $B_{max}$ value of 1.30+0.03 pmol/mg protein (n=3). FIG. 5 shows a saturation curve of compound 102 binding to adenosine $A_3$ receptors in HL60 membranes and the linearity of the Scatchard plot in the inset is indicative of the presence of a single class of binding sites with a Kd value of 1.2±0.1 nM and Bmax value of 626±42 fmol/mg protein (n=3).

These results show that many cell lines contain relatively large numbers of adenosine receptors. Because compound 108 is known to bind $A_3$ receptors with a high affinity and

Example 23

Pharmaceutical Formulations (A) Transdermal System—for 1000 Patches

| Ingredients | Amount |
| --- | --- |
| Active compound | 100 g |
| Silicone fluid | 450 g |
| Colloidal silicon dioxide | 2 g |

(B) Oral Tablet—for 1000 Tablets

| Ingredients | Amount |
| --- | --- |
| Active compound | 50 g |
| Starch | 50 g |
| Magnesium Stearate | 5 g |

The active compound and the starch are granulated with water and dried. Magnesium stearate is added to the dried granules and the mixture is thoroughly blended. The blended mixture is compressed into tablets.

(C) Injection—for 1000, 1 mL Ampules

| Ingredients | Amount |
| --- | --- |
| Active compound | 10 g |
| Buffering Agents | q.s. |
| Propylene glycol | 400 mg |
| Water for injection | q.s. 1000 mL |

The active compound and buffering agents are dissolved in the propylene glycol at about 50° C. The water for injection is then added with stirring and the resulting solution is filtered, filled into ampules, sealed and sterilized by autoclaving.

(D) Continuous Injection—for 1000 mL

| Ingredients | Amount |
| --- | --- |
| Active compound | 10 g |
| Buffering agents | q.s. |
| Water for injection | q.s. 1000 mL |

Although the present invention has been described in terms of specific embodiments, various substitutions of materials and conditions can be made as will be known to those skilled in the art. For example, medicaments prepared from the compounds of the present invention may incorporate other excipients and color identifying means as well as be modified in accordance with desired potency and patient administration methods. Other variations will be apparent to those skilled in the art and are meant to be included herein. The scope of the invention is only to be limited by the following claims:

What is claimed is:

1. A compound of the following formula:

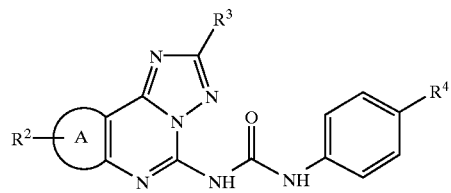

wherein:

A is imidazole, pyrazole, or triazole;

$R^2$ is hydrogen, alkyl, substituted alkyl, alkenyl, aralkyl, substituted aralkyl, heteroaryl, substituted heteroaryl or aryl;

$R^3$ is furan; and $R^4$ is hydrogen, alkyl, amino, substituted alkyl, alkyl substituted amino, alkyl di-substituted amino, alkenyl, aralkyl, substitute aralkyl, heteroaryl, substituted heteroaryl, heterocycle, aryl, substituted aryl, sulfonyl or substituted sulfonyl; and pharmaceutically acceptable salts thereof.

2. The compound of claim 1 wherein $R^2$ is selected from the group consisting of hydrogen, alkyl, alkenyl and aryl.

3. The compound of claim 1 wherein A is a triazolo ring.

4. The compound of claim 1 wherein A is a pyrazolo ring.

5. A compound of the following formula:

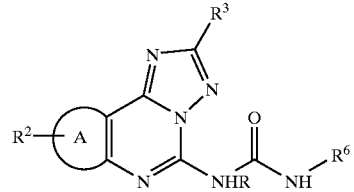

wherein:

A is imidazole, pyrazole, or triazole;

$R^2$ is hydrogen, alkyl, substituted alkyl, alkenyl, aralkyl, substituted aralkyl, heteroaryl, substituted heteroaryl or aryl;

$R^3$ is furan; and $R^6$ is heteroaryl or substituted heteroaryl; and pharmaceutically acceptable salts thereof.

6. The compound of claim 5 wherein $R^2$ is selected from the group consisting of hydrogen, alkyl, alkenyl and aryl.

7. The compound of claim 5 wherein A is a triazolo ring.

8. The compound of claim 5 wherein A is a pyrazolo ring.

* * * * *